(12) United States Patent
Kron et al.

(10) Patent No.: US 11,129,570 B2
(45) Date of Patent: Sep. 28, 2021

(54) DEVICES AND METHODS FOR TISSUE IMMOBILIZATION AND NON-INVASIVE LOWER URINARY TRACT ANALYSIS

(71) Applicant: BioFluid Technology, Inc., Bryn Mawr, PA (US)

(72) Inventors: Reuben E Kron, Bryn Mawr, PA (US); Stephen J Kron, Chicago, IL (US)

(73) Assignee: BioFluid Technology, Inc., Bryn Mawr, PA (US)

(*) Notice: Subject to any disclaimer, the term of this patent is extended or adjusted under 35 U.S.C. 154(b) by 483 days.

(21) Appl. No.: 16/104,316

(22) Filed: Aug. 17, 2018

(65) Prior Publication Data

US 2019/0000387 A1 Jan. 3, 2019

Related U.S. Application Data

(60) Continuation of application No. 15/589,107, filed on May 8, 2017, now Pat. No. 10,080,525, which is a continuation of application No. 14/996,373, filed on Jan. 15, 2016, now Pat. No. 9,675,295, which is a division of application No. 14/208,829, filed on Mar. 13, 2014, now Pat. No. 9,277,884.

(60) Provisional application No. 61/781,624, filed on Mar. 14, 2013.

(51) Int. Cl.
*A61B 5/00* (2006.01)
*A61B 5/20* (2006.01)

(52) U.S. Cl.
CPC ............ *A61B 5/6834* (2013.01); *A61B 5/205* (2013.01); *A61B 5/208* (2013.01)

(58) Field of Classification Search
CPC ........ A61B 5/205; A61B 5/208; A61B 5/6834
See application file for complete search history.

(56) References Cited

U.S. PATENT DOCUMENTS

| | | | |
|---|---|---|---|
| 4,380,997 A | 4/1983 | Leibo | |
| 4,589,280 A * | 5/1986 | Carter | A61B 5/201 600/573 |
| 4,683,748 A * | 8/1987 | Carter | A61B 5/201 600/573 |
| 4,696,672 A | 9/1987 | Mochizuki et al. | |
| 5,108,382 A | 4/1992 | Wright et al. | |
| 5,377,101 A | 12/1994 | Rollema | |
| 5,616,138 A | 4/1997 | Propp | |
| 5,807,278 A | 9/1998 | McRae | |
| 5,823,972 A | 10/1998 | McRae | |

(Continued)

FOREIGN PATENT DOCUMENTS

| | | |
|---|---|---|
| DE | 19619597 A1 | 11/1997 |
| WO | WO 2000-027285 A1 | 5/2000 |
| WO | WO 2003-024330 A2 | 3/2003 |

OTHER PUBLICATIONS

Phillip P. Smith, et al., Detrusor expulsive strength is preserved, but responsiveness to bladder filling and urinary sensitivity is diminished in the aging mouse, Mar. 2012, Am J Physiol Regul Integr Comp Physiol, (Year: 2012).*

(Continued)

*Primary Examiner* — Sean P Dougherty
(74) *Attorney, Agent, or Firm* — BakerHostetler

(57) ABSTRACT

Provided are devices and methods suitable for immobilizing tissue and for use in non-invasive methods of assessing lower urinary tract symptoms as well as in surgical application.

15 Claims, 59 Drawing Sheets

(56) References Cited

U.S. PATENT DOCUMENTS

| | | | |
|---|---|---|---|
| 6,311,339 B1* | 11/2001 | Kraus | A61F 5/451 |
| | | | 4/144.1 |
| 6,506,169 B2 | 1/2003 | Griffiths | |
| 6,805,662 B2 | 10/2004 | Shah et al. | |
| 8,690,790 B2* | 4/2014 | Addington | A61B 5/202 |
| | | | 600/561 |
| 9,277,884 B2 | 3/2016 | Kron et al. | |
| 9,675,295 B2 | 6/2017 | Korin et al. | |
| 2001/0020162 A1* | 9/2001 | Mosel | A61B 5/205 |
| | | | 604/544 |
| 2004/0260163 A1 | 12/2004 | Kron et al. | |
| 2008/0078771 A1* | 4/2008 | Tsukahara | B65D 81/3846 |
| | | | 220/592.2 |
| 2010/0049031 A1* | 2/2010 | Fruland | A61B 18/1492 |
| | | | 600/411 |
| 2013/0184679 A1 | 7/2013 | Ziebol et al. | |
| 2014/0275839 A1* | 9/2014 | Kron | A61B 5/6834 |
| | | | 600/301 |
| 2014/0378918 A1 | 12/2014 | Dong | |
| 2016/0022194 A1 | 1/2016 | Kron et al. | |
| 2016/0051176 A1 | 2/2016 | Ramos et al. | |

OTHER PUBLICATIONS

Gommer et al., "Validity of a Non-invasive Determination of the Isovolumetric Bladder Pressure During Voiding in Men with LUTS," Neurology and Urodynamics, 1999, 18, 477-486.

Pel et al., "Non-invasive Measurement of Bladder Pressure Using an External Catheter," Neurology and Urodynamics, 1999, 18, 455-475.

Rikken et al., "Repeat non-invasive bladder pressure measurements with an external catheter," The Journal of Urology, Aug. 1999, 162, 474-479.

Sullivan et al., "Penile Urethral Compression—Release Maneuver as an Non-invasive Screening Test for Diagnosing Prostatic Obstruction," Neurology and Urodynamics, 2000, 19, 657-669.

\* cited by examiner

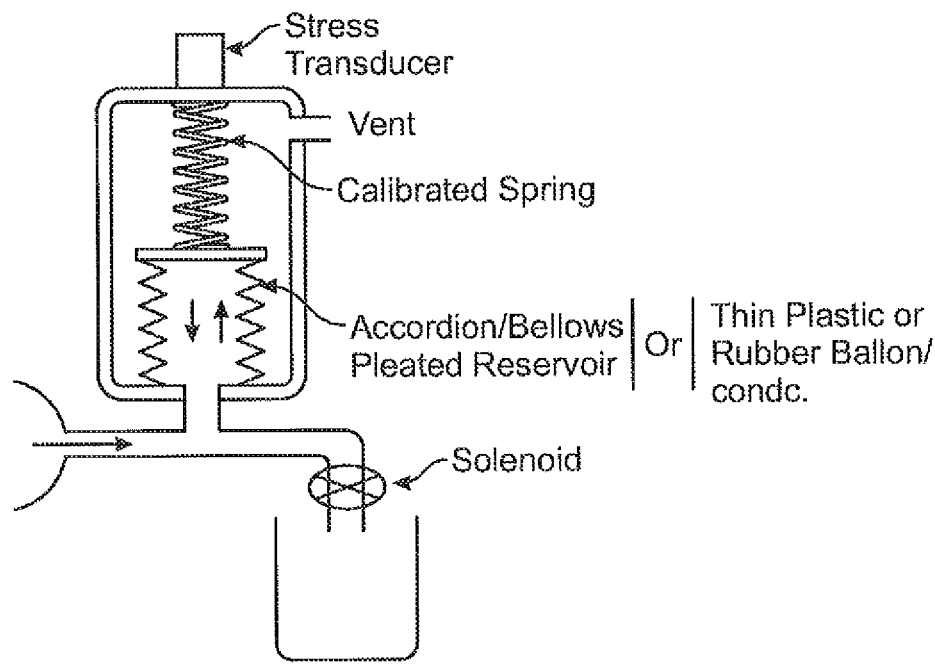
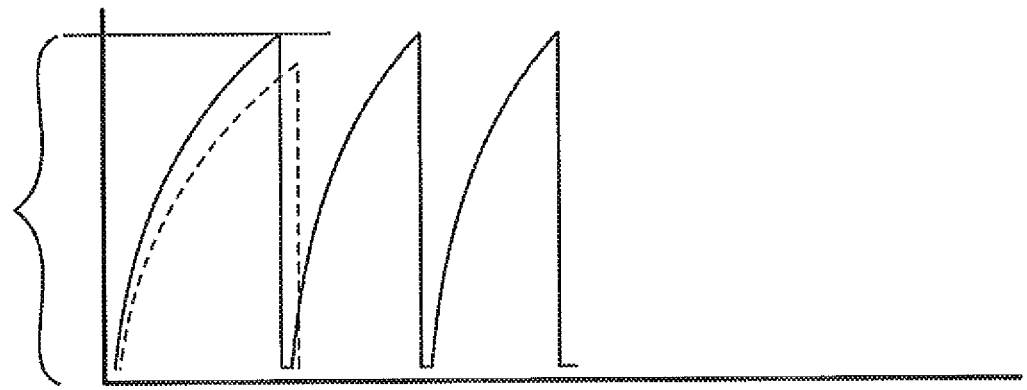
Need Equation for Diabatic Heating Effect on Air Pressure
(Based on Time Constant @ Given Rate of Press↑)
FIG. 10

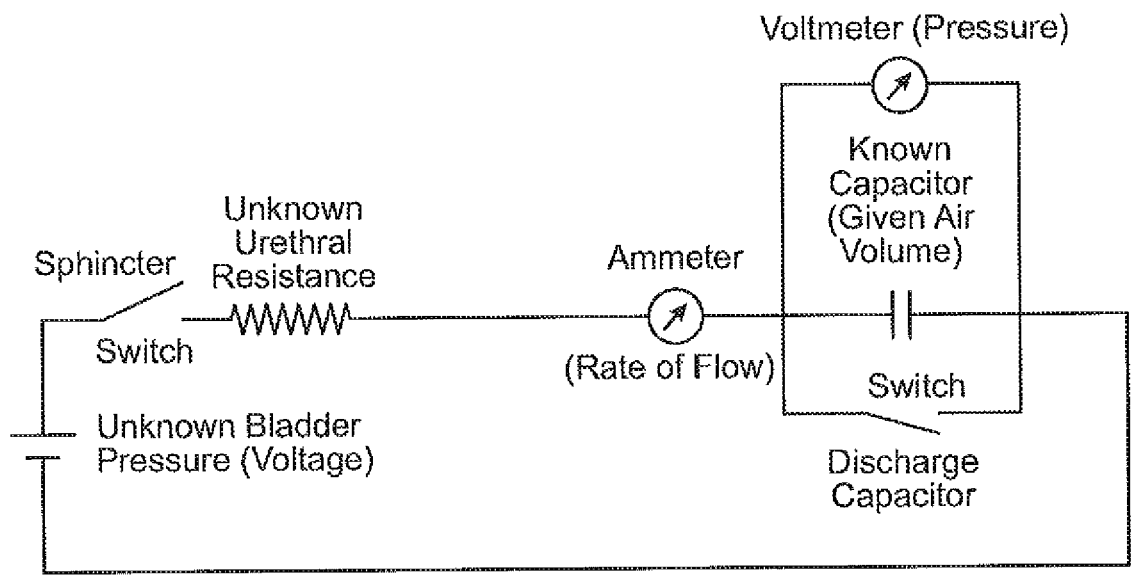
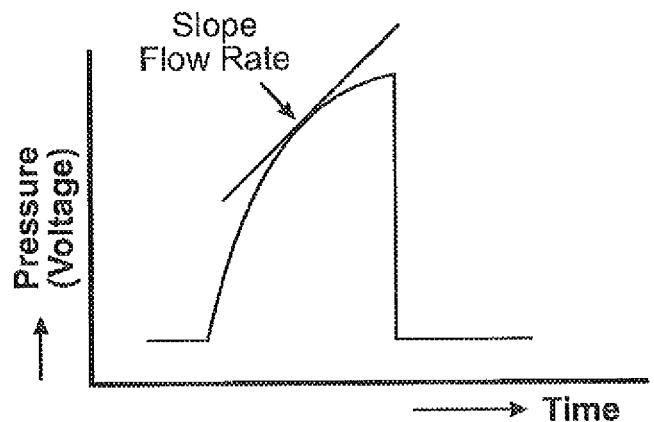
FIG. 17

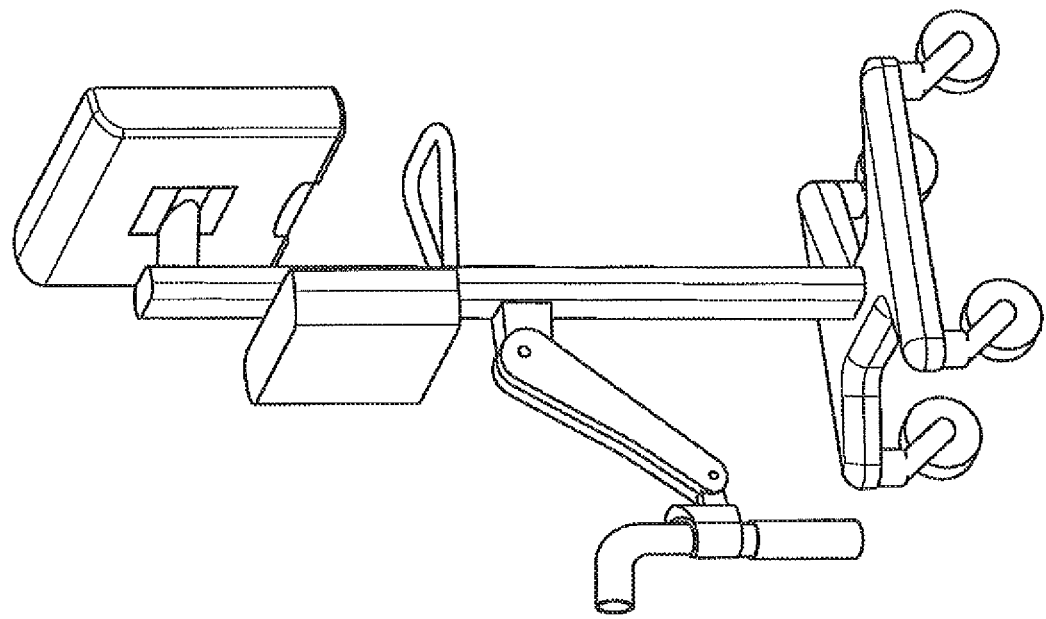
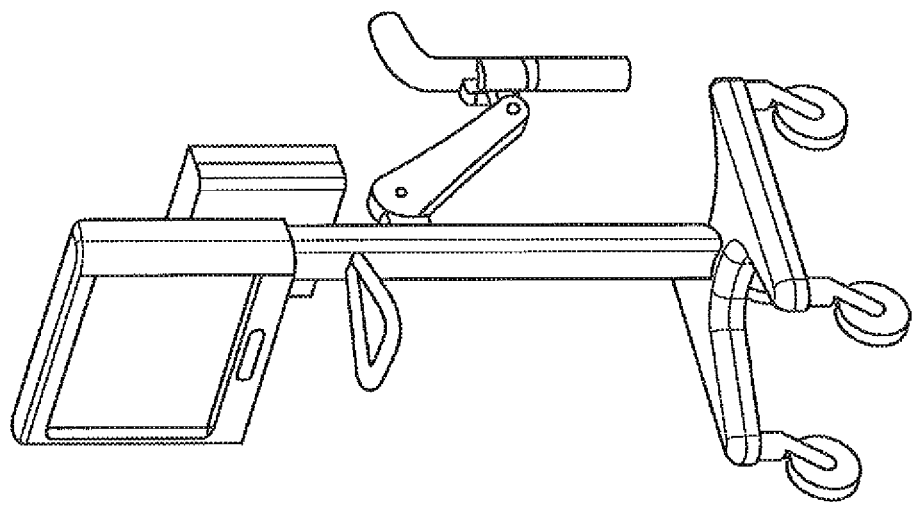
FIG. 30

System Configuration Panel

*Acquisition Parameters*

| | |
|---|---|
| 100 | Sampling Rate (S/s) |
| 60.00 | Maximum Pressure (mm Hg) |
| 0.25 | Solenoid Valve Open Time (s) |
| RSE | Terminal Configuration |
| 1.00 | No Change Timeout (s) |
| 5.00 | No Change Tolerance (%) |
| 5.00 | No Change Minimum (mm Hg) |

*Analysis Parameters*

| | |
|---|---|
| 5.00 | DAQ Filter (Hz)  ON |
| 0.00 | Effective Zero Pressure (mm Hg) |
| 1.00 | Maximum Curve Error (MSE) |
| 50 | Minimum Number of Points |
| 760.00 | Atmospheric Pressure (mm Hg) |
| 500.00 | Initial Air Volume (ml) |

LOAD  SAVE  RETURN

*FIG. 42*

Acquisition Parameters

- *Sampling Rate (S/s)*
  - The number of samples per second recorded during data acquisition.
- *Maximum Pressure (mmHg)*
  - The maximum pressure value that is reached before triggering the solenoid valve venting process during data acquisition.
- *Solenoid Valve Open Time (s)*
  - Number of seconds to open the solenoid valve during the venting process.
- *Terminal Configuration*
  - DAQ hardware wiring consideration.
- *No Change Timeout (s)*
  - Number of seconds to consider a timeout if all points within this timeframe are within the no change tolerance. A timeout then triggers the venting process.
- *No Change Tolerance (%)*
  - Threshold for considering a "no change." If the first and last points in the timeout window are within the tolerance percentage of the average of all the points in the window, then the venting process is triggered.
- *No Change Minimum (mm Hg)*
  - This is the minimum pressure required to trigger a "no change" event. By setting a minimum, it will prevent unwanted triggers at baseline pressure before the patient begins to urinate.

Figure 43

Analysis Parameters

- *DAQ Filter (Hz)*
  - Frequency value for performing a $2^{nd}$ order low-pass Butterworth filter before the analysis process. This frequency is filtered out to prevent physical artifacts during the data acquisition process.
- *Effective Zero Pressure (mm Hg)*
  - Given baseline value to be adjusted for during the analysis process. This value will shift the entire data set positive or negative to adjust for the baseline value.
- *Maximum Curve Error (MSE)*
  - The maximum mean squared error value for each curve in the set to be accepted and included in the total number of curves.
- *Minimum Number of Points*
  - The minimum number of points in a curve to be considered significant enough to be fit to a curve.
- *Atmospheric Pressure (mm Hg)*
  - The atmospheric pressure during a given test, which is accounted for during the analysis process to determine changes in volume based on changes in pressure using the ideal gas law.
- *Initial Air Volume (ml)*
  - The initial amount of air in the disposable, which is used during the analysis process to determine changes in volume based on changes in pressure using the ideal gas law.

Figure 44

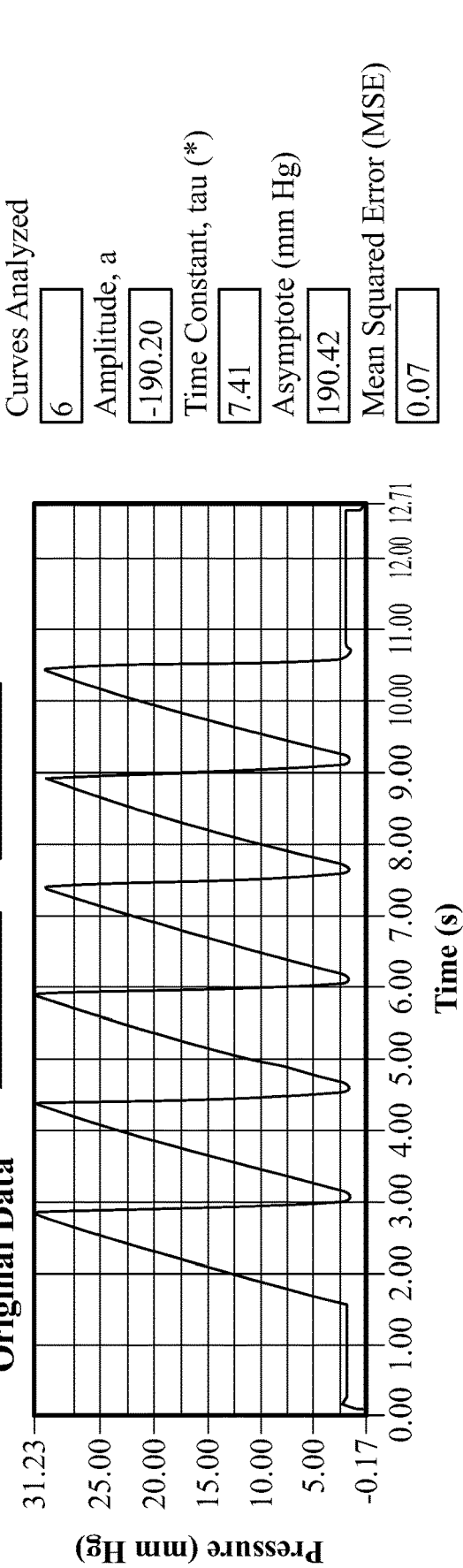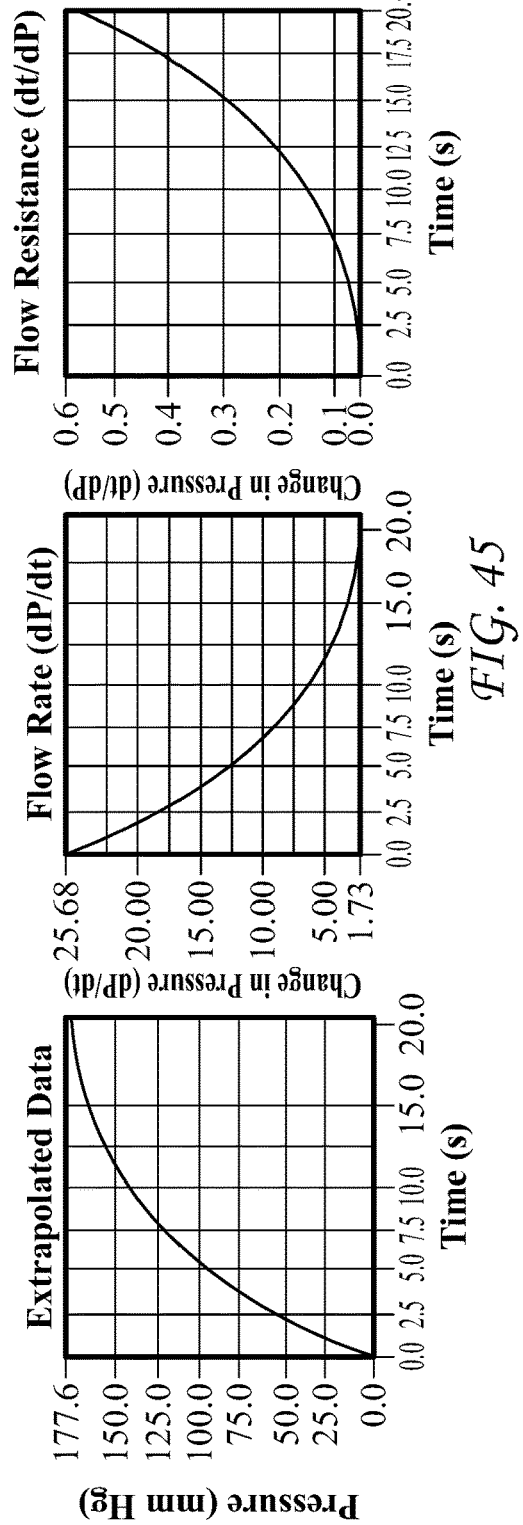
FIG. 45

DEVICES AND METHODS FOR TISSUE IMMOBILIZATION AND NON-INVASIVE LOWER URINARY TRACT ANALYSIS

RELATED APPLICATION

The present application is a continuation of now-allowed U.S. patent application Ser. No. 15/589,107, "Devices And Methods For Tissue Immobilization And Non-Invasive Lower Urinary Tract Analysis" (filed May 8, 2017), which is a continuation of U.S. Pat. No. 9,675,295 (U.S. patent application Ser. No. 14/996,373), "Devices And Methods For Tissue Immobilization And For Non-Invasive Urinary Tract Analysis" (filed Jan. 15, 2016), which application is a divisional of U.S. Pat. No. 9,277,884 (U.S. patent application Ser. No. 14/208,829), "Devices And Methods For Tissue Immobilization And For Non-Invasive Urinary Tract Analysis" (filed Mar. 13, 2014), which claims priority to U.S. Patent Application No. 61/781,624, "Devices And Methods For Tissue Immobilization And For Non-Invasive Urinary Tract Analysis" (filed Mar. 14, 2013). The present application claims priority to and the benefit of the foregoing applications, all of which applications are incorporated herein by reference in their entireties for any and all purposes.

GOVERNMENT RIGHTS

This invention was made with government support under Internal Revenue Service Qualifying Therapeutic Discovery Program ("QTDP") grant entitled "Non-invasive Urethrocystometer." The government has certain rights in the invention.

TECHNICAL FIELD

The present disclosure relates to the field of uroflowmetry, to the field of urodynamics, and to the field of medical devices.

BACKGROUND

Lower Urinary Tract Symptoms (LUTS) such as urinary frequency, urgency, nocturia, and diminished or interrupted urine flow (sometimes termed "weak stream") are suggestive of urethral obstruction caused by Benign Prostatic Hyperplasia (BPH). Other lower urinary tract disorders (e.g., bladder dysfunction), however, may present with the same symptoms. Unfortunately, the non-invasive diagnostic tests recommended by the American Urological Association (AUA), including the patient self-report scale (e.g., the AUA symptom index) and simple office uroflowmeters that measure flow rate during urination are unable to accurately determine the source of LUTS, especially whether the symptoms are caused by blockage of the urethra due to BPH, or from bladder weakness or some other lower urinary tract condition. A depiction of the lower urinary tract is provided in FIG. 58 attached hereto.

The causes of LUTS are not self-evident. Either a weak bladder (e.g., neurologic damage) or urethral obstruction (e.g., BPH) can cause "weak stream." Statistically, in men obstruction is twice as likely as poor bladder pressure, so if a trial on medication is not effective, diagnostic/therapeutic prostate surgery is performed. Surgery helps 2 out of 3 patients. However, about 1 in 3 is not helped, and overall about 1 in 20 has some significant side effect from the procedure. Many dollars are spent each year on unneeded prostate procedures and also on the cost of managing adverse effects of the unnecessary surgery.

Some procedures, such as urodynamic studies, can diagnose bladder dysfunction, but are not recommended by the AUA because they are invasive (they involve placement of catheters in the urethra and bladder), and therefore are associated with a significant rate of trauma, infection and other complications. Further, these invasive urodynamic procedures require complex equipment and skilled personnel, and are expensive and uncomfortable for the patient, and cannot be conveniently repeated to confirm abnormal findings or to evaluate response to treatment.

By age 65 many men have enlarged prostates and eventually about one third undergo prostate surgery, mostly for management of symptoms thought to be caused by urethral blockage secondary to BPH, otherwise known as bladder outlet obstruction (BOO). But after surgery many men continue to experience the same LUTS plus additional problems (such as erectile dysfunction and loss of sphincter control secondary to surgical injury). Although more than $3 billion is spent each year in the U.S. for prostate surgery (mostly for BPH), one in three surgical procedures for BPH does not result in relief of LUTS because the urinary tract symptoms initially attributed to BPH were caused by factors other than urethral obstruction.

The expense and risk of existing invasive urodynamic methods make it impractical to perform pre- and post-operative studies to identify bladder dysfunction and objectively measure response to treatment. Although uroflowmetry is presently considered a suitable noninvasive test for detecting lower urinary tract dysfunction, the test does not determine the cause of the dysfunction or specify a "cutoff" flow value that can be used to determine what therapy is appropriate.

In one prospective blind study of uroflowmetry on patients undergoing prostate surgery for LUTS, those patients with peak flow rates above 15 ml/s had significantly less symptom relief from prostate surgery, suggesting that in patients with flow rates above 15 ml/s it is unlikely that obstruction due to BPH is the source of the LUTS. The findings indicate that for many patients urinary tract symptoms are not due to urethral obstruction, but instead involve dysfunction of the bladder. Other studies have shown that uroflowmetry results were not helpful in diagnosing obstruction due to BPH. Thus, the focus on uroflowmetry places an emphasis on a single non-invasive test of questionable diagnostic specificity. Also, nearly all commercially available urodynamic tests that measure bladder function are invasive, and current invasive urodynamic studies also have a poor risk to benefit quotient due to cost and potential complications. Existing non-invasive techniques to measure isovolumetric (i.e., maximum or asymptotic) bladder pressure during urination—such as an inflatable cuff attached to the penis—are inaccurate, painful and also difficult to use in a consistent manner. Accordingly, there is a long-felt need for an accurate, simple, safe, painless, low-cost, and non-invasive technology to determine the source of lower urinary tract symptoms.

SUMMARY

In meeting these long-felt needs, the present disclosure provides, inter alia, components. These components suitably comprise a vacuum chamber having an entry opening configured to engage with a subject's anatomy proximate to a subject's urethra, the vacuum chamber having an outlet port configured to engage with a vacuum source; a urethral engagement conduit extending into the vacuum chamber, the urethral engagement conduit having a proximal opening configured to engage a subject's anatomy proximate to the subject's urethra, the entry opening of the vacuum chamber and the proximal opening of the urethral engagement conduit defining a gap therebetween, the gap being configured so as to enable passage of the subject's anatomy proximate to the urethra through the gap and into the vacuum chamber upon application of sufficient vacuum, the component being configured to give rise to a leak-proof mechanical seal under vacuum between the proximal opening and the anatomy proximate to a urethra upon application of sufficient vacuum; and the component further comprising a receptacle in fluid communication with the urethral engagement conduit (e.g., the distal opening of the urethral engagement conduit), the receptacle further comprising a receptacle aperture in some embodiments. Because the disclosed technology is non-invasive, it avoids the need for uncomfortable devices that are used in existing urological studies, including anal probes, penile cuffs, and the like.

Also provided are systems, the systems suitably comprising a receptacle, a component configured to effect mechanical, leak-proof fluid communication between a subject's urethra and the receptacle so as to give rise to a flow circuit; the component comprising a vacuum chamber having an entry opening adapted to engage with a subject's anatomy proximate to the subject's urethra. The system may be configured to, under application of sufficient vacuum to the vacuum chamber, effect fluid communication between the subject's urethra and the receptacle, and the system may include a sensor configured to measure a pressure within the receptacle.

Also provided are methods, comprising applying sufficient vacuum to a vacuum chamber so as to effect passage of a subject's anatomy into the vacuum chamber through a gap between an opening in the vacuum chamber and an opening of a urethral engagement conduit, the vacuum being applied so as to effect leak-tight fluid communication between the subject's urethra and a receptacle; and measuring, as a function of time during urine excretion, a pressure within the receptacle.

Additional provided are components, comprising a vacuum chamber, the vacuum chamber comprising a tap or other port adapted for application of vacuum, and the vacuum chamber defining at least one opening formed therein, the at least one opening being adapted to, upon application of sufficient vacuum, securably engage with tissue.

Also provided are methods, the methods comprising contacting a vacuum chamber comprising at least one tissue engagement aperture to a body tissue; and providing sufficient vacuum to the vacuum chamber so as to draw at least some of the body tissue into the vacuum chamber and so as to physically stabilize at least part of the tissue.

Further provided are components, comprising a vacuum chamber, the vacuum chamber comprising a tap adapted for application of vacuum, and the vacuum chamber defining at least one opening formed therein, the at least one opening being adapted to, upon application of sufficient vacuum, securably engage with tissue.

Also provided are methods, comprising contacting a vacuum chamber comprising at least one tissue engagement aperture to a body tissue; and applying sufficient vacuum to the vacuum chamber so as to draw at least some of the body tissue into the vacuum chamber and so as to physically stabilize at least part of the tissue.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale or proportion. In the drawings:

FIG. 10 depicts a mechanically-based pressure measurement system according to the present disclosure—a spring and/or air compression provide back-pressure;
FIG. 17 depicts a capacitance-based model of the urethrocystometer in which one may calculate flow-rate from slope of time-pressure curve, and flow resistance is calculated from inverse slope; Slope=Flow Rate and 1/Slope=Resistance.

FIG. 30 illustrates an exemplary system according to the present disclosure;

FIG. 39 through FIG. 45 provide an illustration of an exemplary flow for a urological assessment according to the present disclosure;

DETAILED DESCRIPTION OF ILLUSTRATIVE EMBODIMENTS

Figure 1:
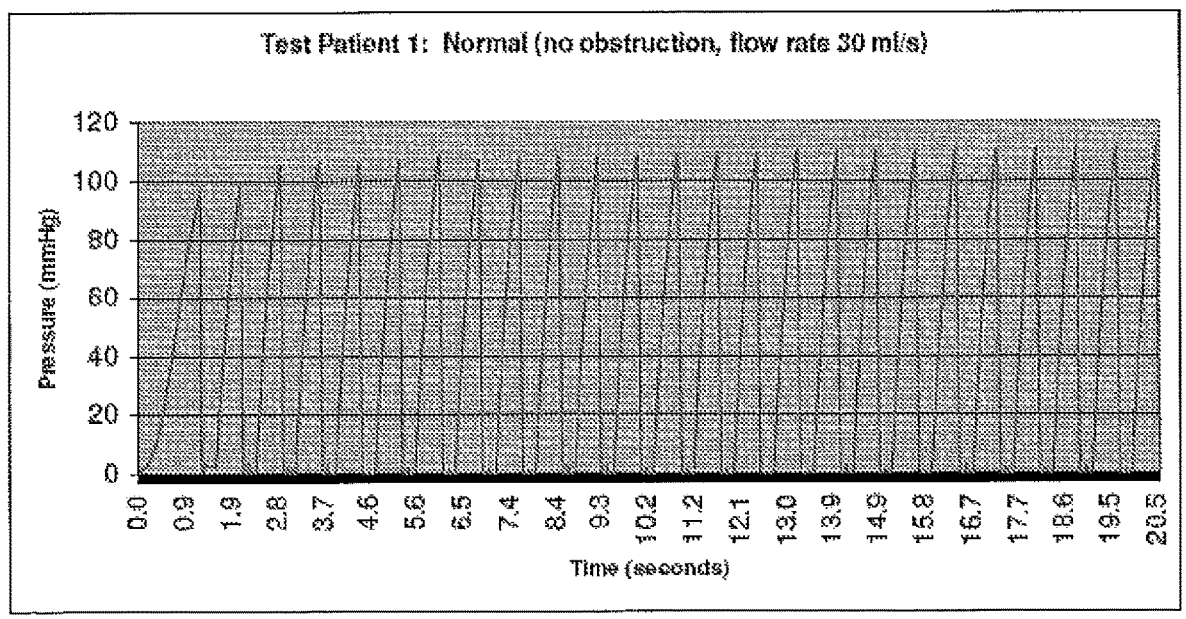
FIG. 1 provides a pressure vs. time plot for Test Patient 1.

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and all documents cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As described elsewhere herein, the present disclosure provides, inter alia, a non-steady state approach to analyzing fluid dynamics of complex flow systems. One may then use a computer controlled device for interrupting flow, and then the instantaneous response of the system variables (flow, resistance, compliance, and pressure) is measured as urine flow is repeatedly interrupted.

Components

The measurements are obtained by mating the patient's urethra to an instrument or system that comprises flow controlling and measuring (e.g., Flow and Pressure Measurement and Control; "FPMC") components by means of a connecting device, which may in some cases be termed a Urethra Engagement Device ("UED"). Analysis of the resulting time-varying pressures and flows yields values having clinical significance.

The UED (which may be referred to as a component and may, in some embodiments, also be disposable, semi-disposable or reusable) provides an interface between the test subject and other instrumentation. In males, the UED attaches to the end of the penis by suction, providing a completely leak-free seal. If the seal is not leak-proof (e.g., the component has not been properly aligned with respect to the urethra), the user may observe urine collecting in the vacuum chamber (which also serves as the urine trap). In such a case, the user may re-align the component relative to the urethra and repeat the testing.

Suction used to form the seal is suitably produced and controlled by a vacuum supply subsystem. In some embodiments, a UED may include concentric tubes suitably configured to grasp the glans penis. The inner tube serves as an extension of the urethra. The size and shape of the inner tube permit the urethral orifice to be fully encompassed and yet be free to open with minimal resistance to urine flow. The space between the tubes may be evacuated (via vacuum application) to a sub-atmospheric pressure. The glans penis may be coated with a lubricant (e.g., a water-based lubricant) to facilitate passage of glans tissue through the space between the tubes into the vacuum chamber where the tissue expands to physically hold the glans in place. Tube ends may be shaped to immobilize the glans penis, spread open the urethral orifice, and provide a leak-free seal once the vacuum is applied. As one example, the tube ends may be beveled, curved, angled, or otherwise shaped to more easily engage with the subject. The surfaces of the concentric tubes that engage with a subject are suitably smooth and made of transparent materials to facilitate accurate placement of the inner tube around the urethral orifice. A one-size UED fits most males. A suitably designed UED may be used to measure LUT function in females and males with hypospadius. The components are sized and shaped to accommodate anatomic differences. Children and animals may also be tested, as the disclosed technology is not limited to adult humans.

Figure 47:
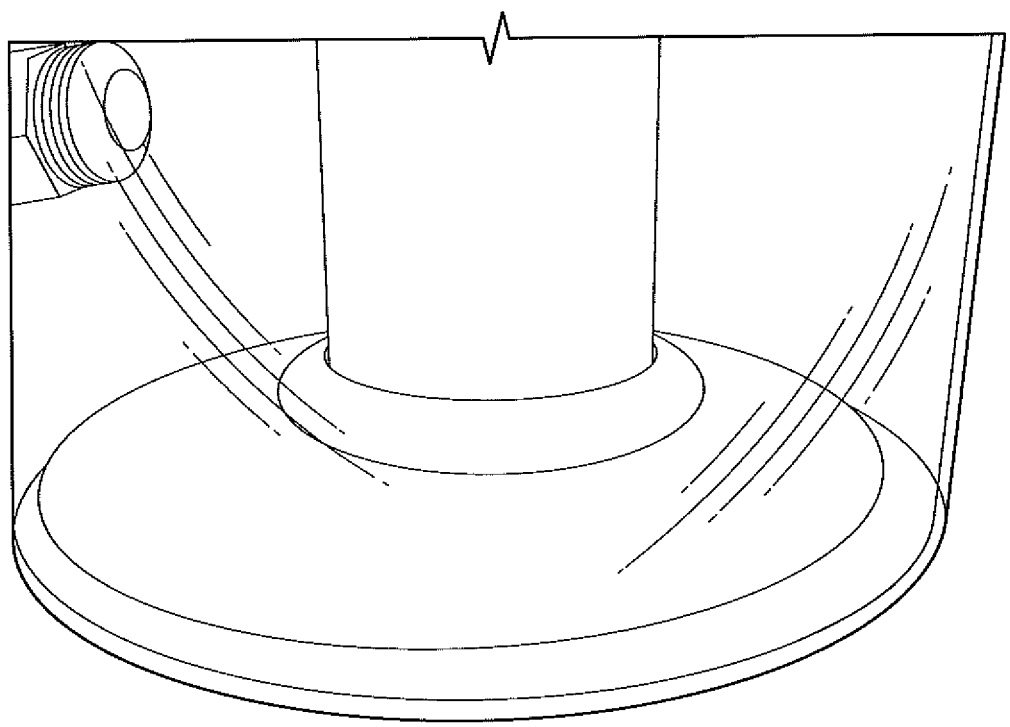
FIG. 47 provides an illustration of an exemplary component according to the present disclosure engaged with the glans of a subject.

As one example, a lubricant (e.g., K-Y™ jelly or other lubricant) is applied to the glans penis and the contacting surfaces of the UED. A vacuum is applied and the glans is centered in the device. The resulting mechanical connection is secure and leak free once a mechanical seal is achieved by drawing pen-urethral tissue through the opening of the vacuum chamber where the tissue may expand and may be physically trapped therein until the vacuum is relieved, as shown in FIG. 47. Therefore, the urine pressure at the urethral orifice may exceed the vacuum applied without also dislodging the device from the periurethral tissue. In this way, once the mechanical connection or seal is formed, one may reduce the vacuum. After mechanical connection is achieved, the vacuum need not necessarily be in excess of the maximum expected bladder pressure (e.g., about 150 mm Hg), and may suitably be less than the pressure likely to rupture capillaries in the glans and result in bruising. FDA approved vacuum constrictor devices used for treatment of male sexual impotence permit application to the penis of sub-atmospheric pressures up to 300 mm Hg. These pressures may be sustained for up to about 30 minutes without adverse consequences in otherwise normal males. The disclosed technology may perform a full data collection and analysis in only a few minutes. The disclosed technology requires only a few minutes to operate, as it requires only time to attach a UED to a subject and for the subject to at least partially empty their bladder through the UED.

It should be understood that in some embodiments, only some portion (e.g., the glans penis or even a portion of the glans penis) of a subject's anatomy is inserted within the device. This can improve patient comfort, as only a small or even minimal amount of tissue is inserted or otherwise engaged by the device.

Figure 6:
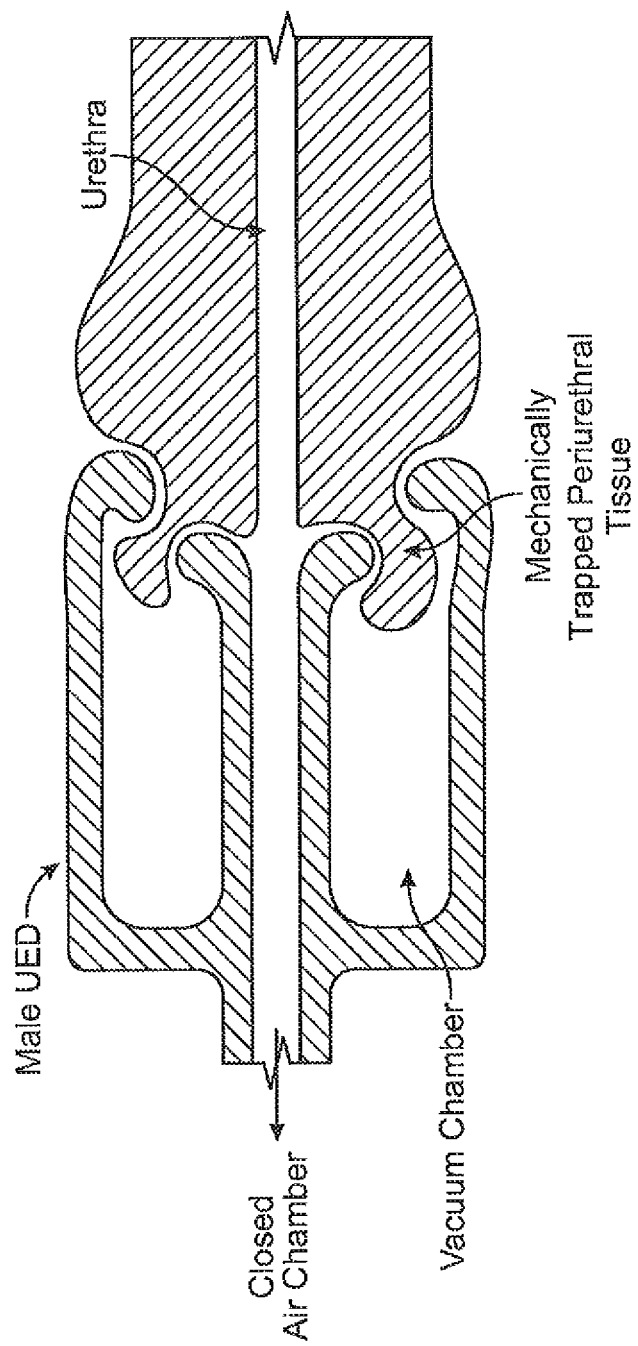
FIG. 6 depicts a urethral engagement device (UED) according to the present disclosure engaged with a glans penis (detail shown in upper region of figure)

The UED is a component (which may be disposable, partially disposable, or even reusable) of the disclosed technology. One exemplary UED is shown in FIG. 6. As shown in that figure, a UED may include a vacuum chamber (labeled) and a central urethral engagement conduit (not labeled). In operation, the UED is contacted to the anatomy proximate to or surrounding a patient's urethra so as to seat the entry of the vacuum chamber around the subject's urethra. A vacuum is applied by way of a port to the vacuum chamber. The vacuum is suitably applied so as to draw pen-urethral tissue into the vacuum chamber through the gap between the vacuum chamber and the urethral engagement conduit, as shown in the upper frame of FIG. 6. The pen-urethral tissue expands, thus creating a leak-proof, mechanical seal between the pen-urethral tissue and the device. The port that leads to the urine receiving chamber (closed air chamber) in the air venting UED serves the purposes of, e.g., (a) venting air through a solenoid valve, and (b) measuring pressure within the closed air chamber by means of a pressure sensor. Both (a) and (b) are directly connected to the port, and both the solenoid valve and the sensor are part of the FPMC system, the sensor providing the pressure data used by the FPMC to control the opening and closing of the solenoid valve, and to generate the pressure-time curves used to calculate the flow rate, the flow resistance, the compliance of the LUT, and the isovolumetric bladder pressure.

As shown in the figure, the proximal end (and opening) of the urethral engagement conduit is suitably disposed at a distance from the peri-urethral engagement opening of the vacuum chamber. The edges of these openings may feature lips, curls, and the like. As one example—such as that shown in FIG. 6—the edges may feature curls, lips, protrusions, or other features that engage expanded peri-urethral tissue so as to assist in seal formation. As described elsewhere herein, one (or both) of the urethral engagement conduit and the vacuum chamber may be capable of motion relative to the other. One (or both) of the urethral engagement conduit and the vacuum chamber may also include a deformable material, such as a silicone or other flexible material, such as a polymer. This may be done so as to facilitate engagement between the device and the subject. Although not shown in the figure, the opening into which the subject's tissue enters may be adjustable, as described elsewhere herein.

Figure 31:
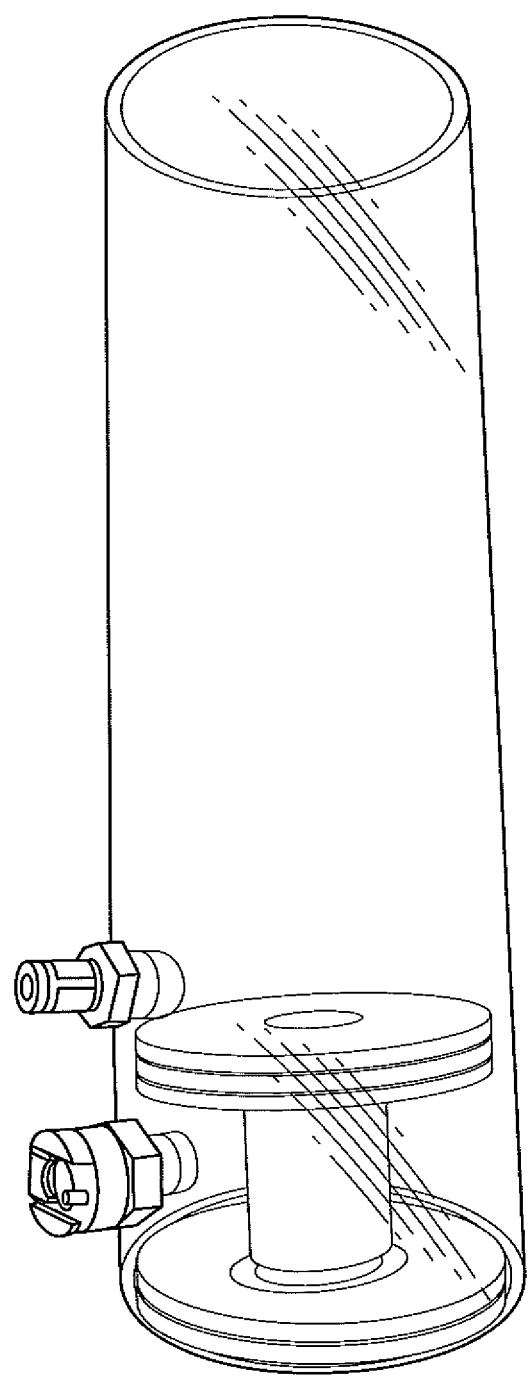
FIG. 31 provides an illustration of a component according to the present disclosure.
Figure 32:
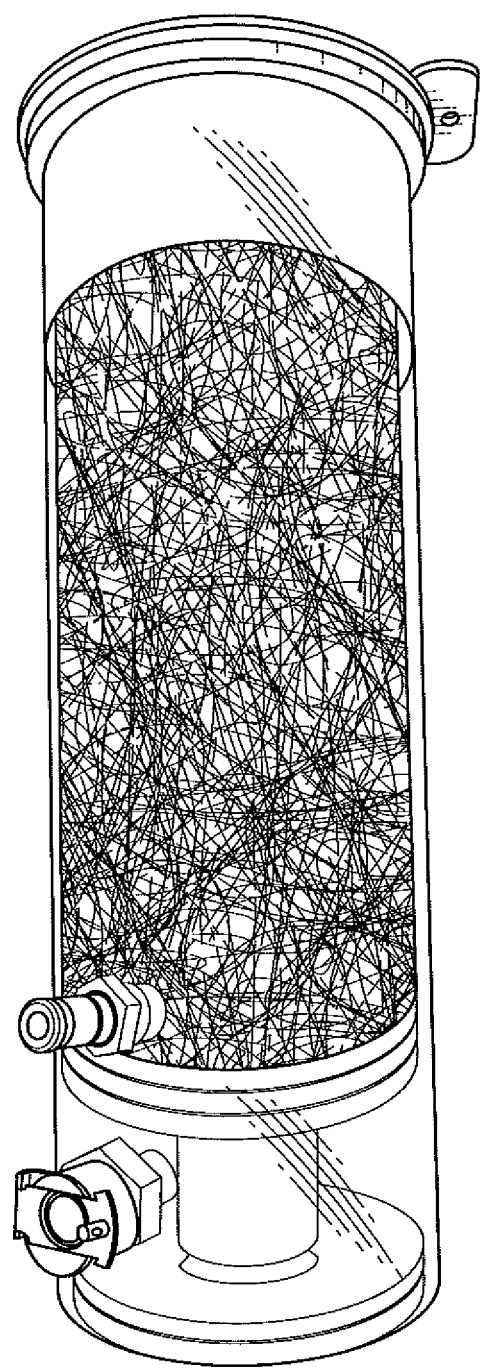
FIG. 32 provides an illustration of a component according to the present disclosure.
Figure 33:
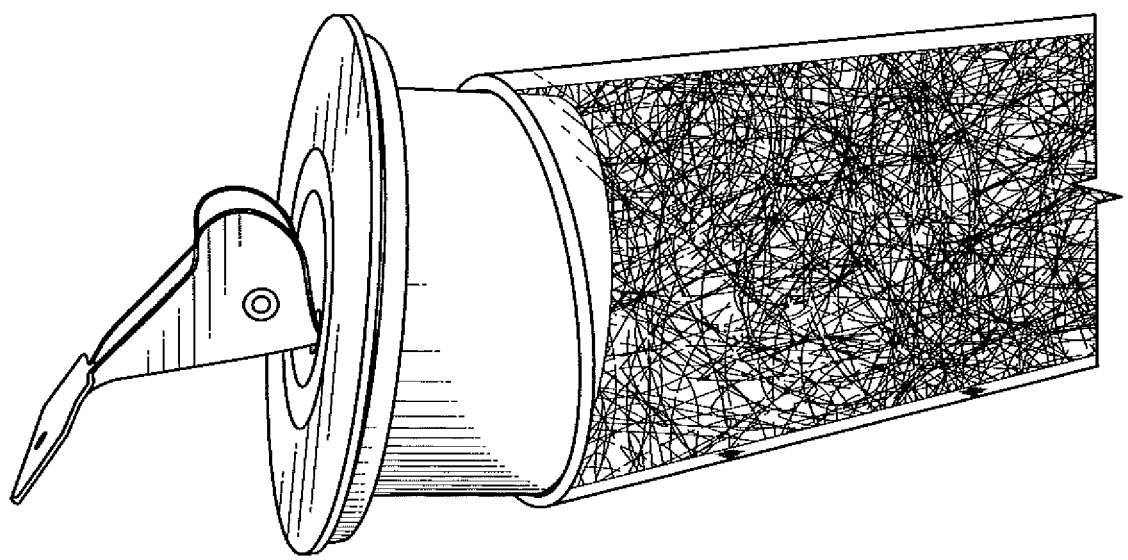
FIG. 33 provides an illustration of an exemplary closure of a component according to the present disclosure.
Figure 34:
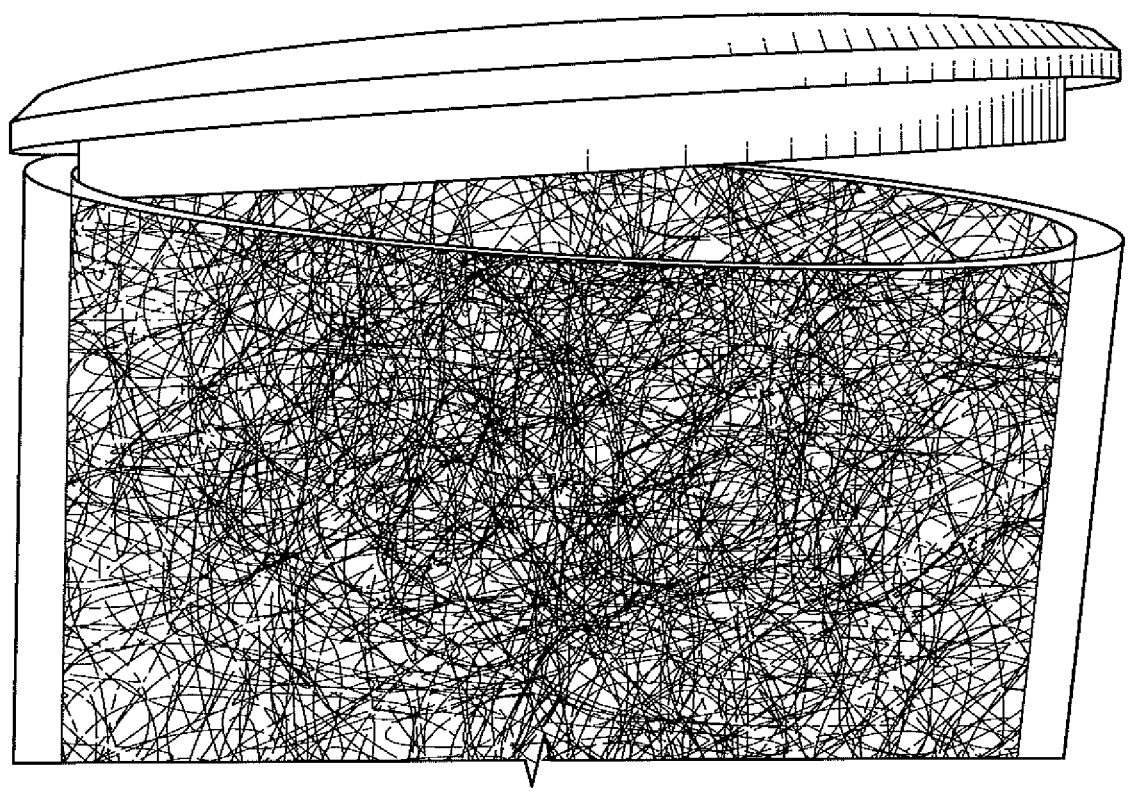
FIG. 34 provides an illustration of an exemplary end seal of a component according to the present disclosure.

Further detail is provided in FIGS. 31-36, which figures provide additional illustrations of components according to the present disclosure. FIG. 31 shows a component according to the present disclosure, including the annular space into which the glans may be drawn and the annular vacuum chamber (or urine trap) on which the vacuum is drawn and into which the user's anatomy may be extended, a vacuum port into the vacuum chamber of the component into which the glans is drawn, the chamber or receptacle into which urine is excreted, and a pressure sensor port in the urine receptacle. FIG. 32 shows the component of FIG. 31, with further illustration of the inclusion of a heat sink material, which can be steel wool or other materials. Glass (e.g., glass wool) and metals are considered especially suitable materials for this purpose. The end of the component may be sealed with a disposable closure, as shown at the right-hand side of the illustration. One such closure is shown in FIG. 33, which illustrates that the urine chamber may be closed with a rubber expansion plug-type seal. Other seals may be used, including polymeric materials, screw-in seals, press-fit seals, interference fit seals, bayonet-type seals, plugs, expander plugs (such as that shown in FIG. 33), and the like; suitable closures will be known to those of ordinary skill in the art. An alternative end seal is shown in FIG. 34, which figure illustrates a press-fit seal; the seal may be cemented into place to create a disposable UED..

Figure 35:
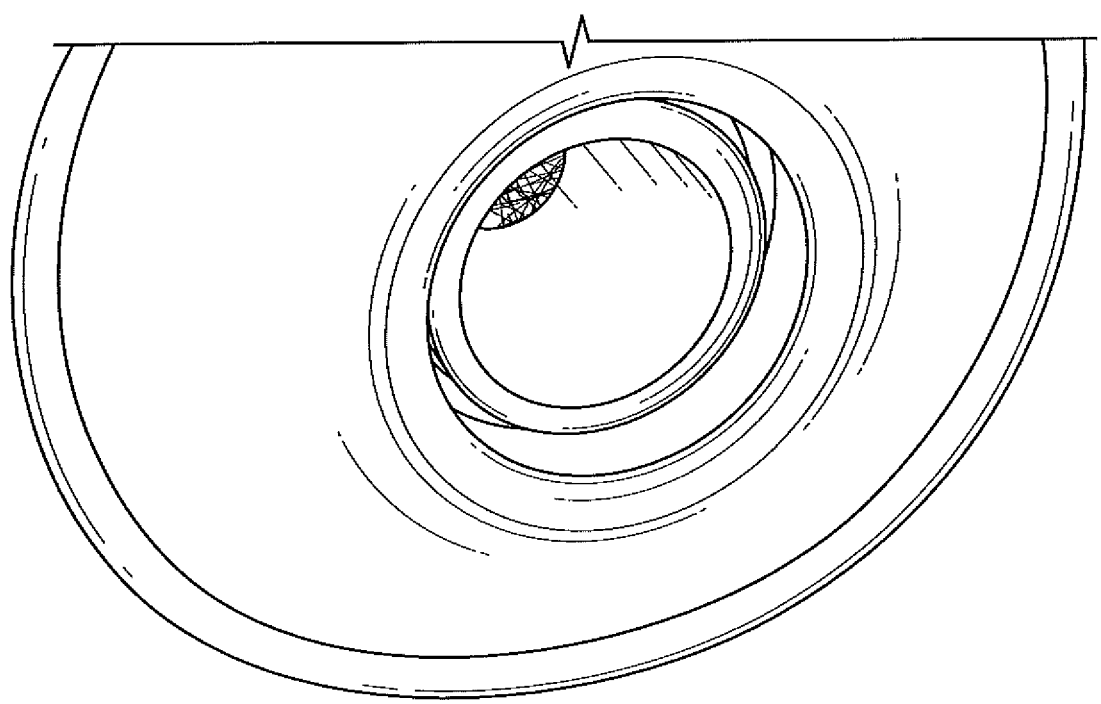
FIG. 35 provides an front-view illustration of a component according to the present disclosure.
Figure 36:
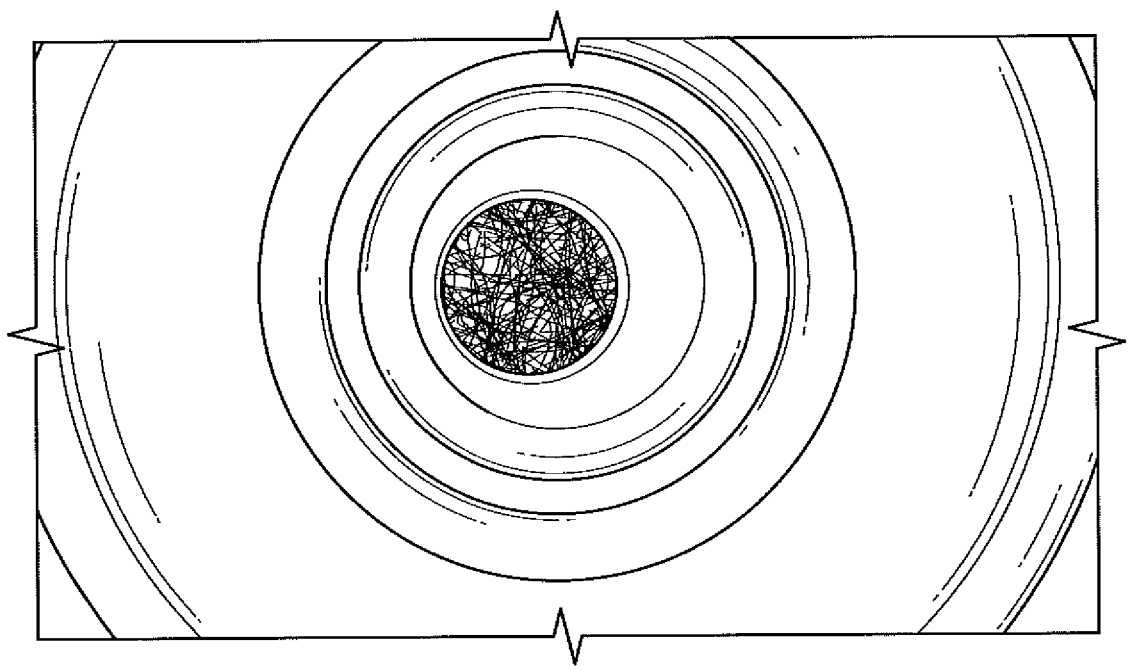
FIG. 36 provides an illustration of a glans tissue stabilizer according to the present disclosure.
Figure 37:
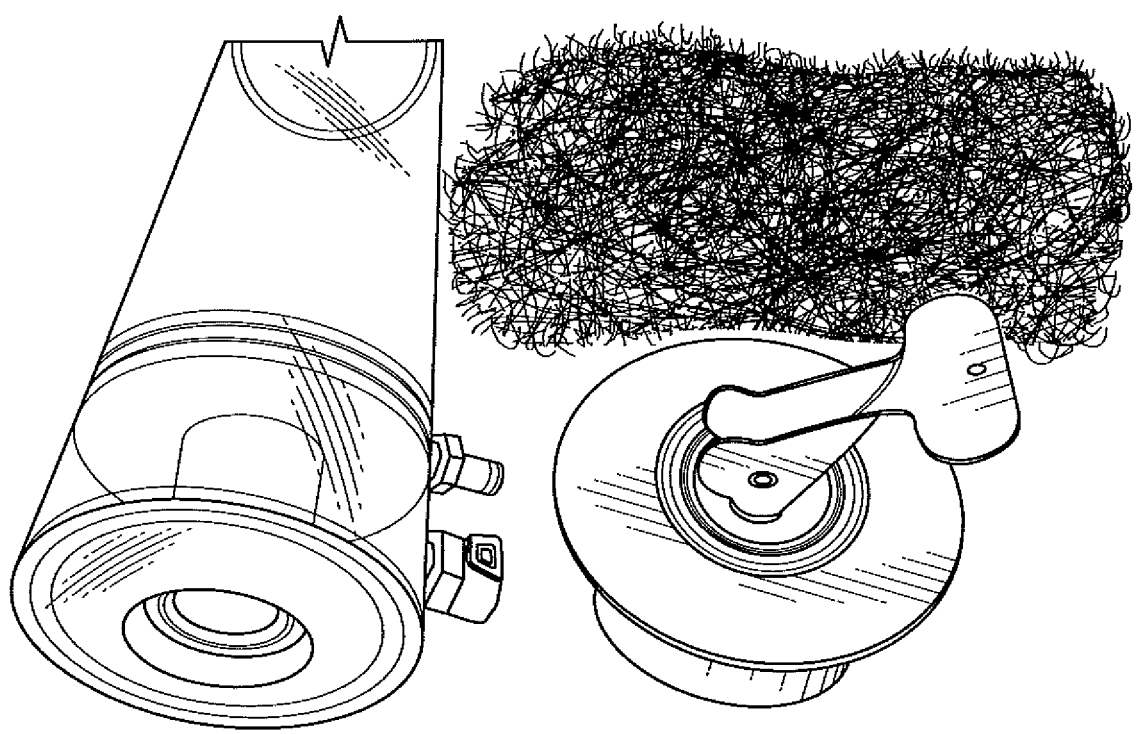
FIG. 37 provides an illustration of the various parts of a component according to the present disclosure.

FIG. 35 illustrates the subject-engagement end of a component according to the present disclosure. As shown in that figure, an annular space is formed between the urethral engagement conduit into which the user excretes urine and the proximal portion of the component, which may be a donut-shaped region against which the user's anatomy rests during use. A vacuum is applied to the vacuum chamber so as to draw the patient's anatomy (e.g., the glans) into and in some embodiments through the annular space so as to form a leak-proof seal. The vacuum may be applied such that the patient's anatomy is extended into the volume on which the vacuum is applied. FIG. 36 is an end-on view of a glans tissue stabilizer according to the present disclosure, again showing the annular space into which the user's anatomy is drawn and also the heat sink within the urine excretion chamber. FIG. 37 illustrates the various parts of a component, including the component, a heat sink material (metal wool), and an end closure used to seal the chamber into which urine is excreted.

Figure 8:
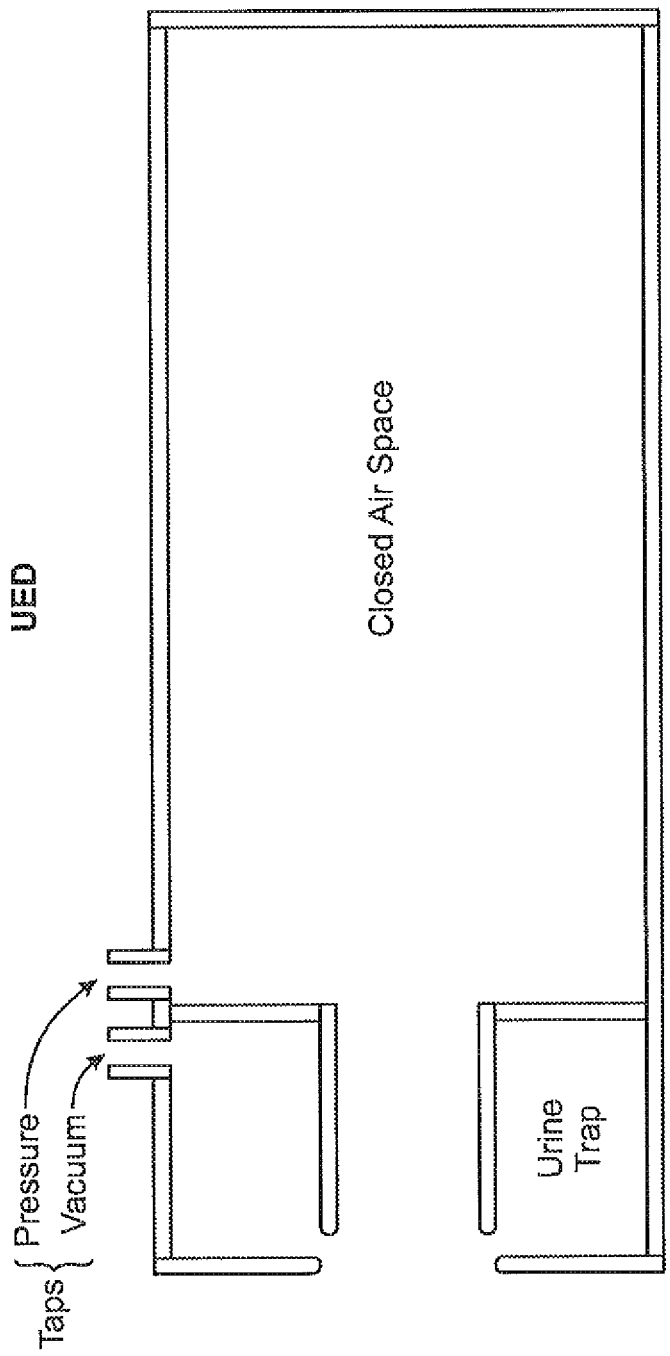
FIG. 8 depicts an exemplary UED (including receptacle and engagement region) according to the present disclosure (vacuum chamber designed to mechanically trap periurethral tissue and achieve water-tight seal)
Figure 46:
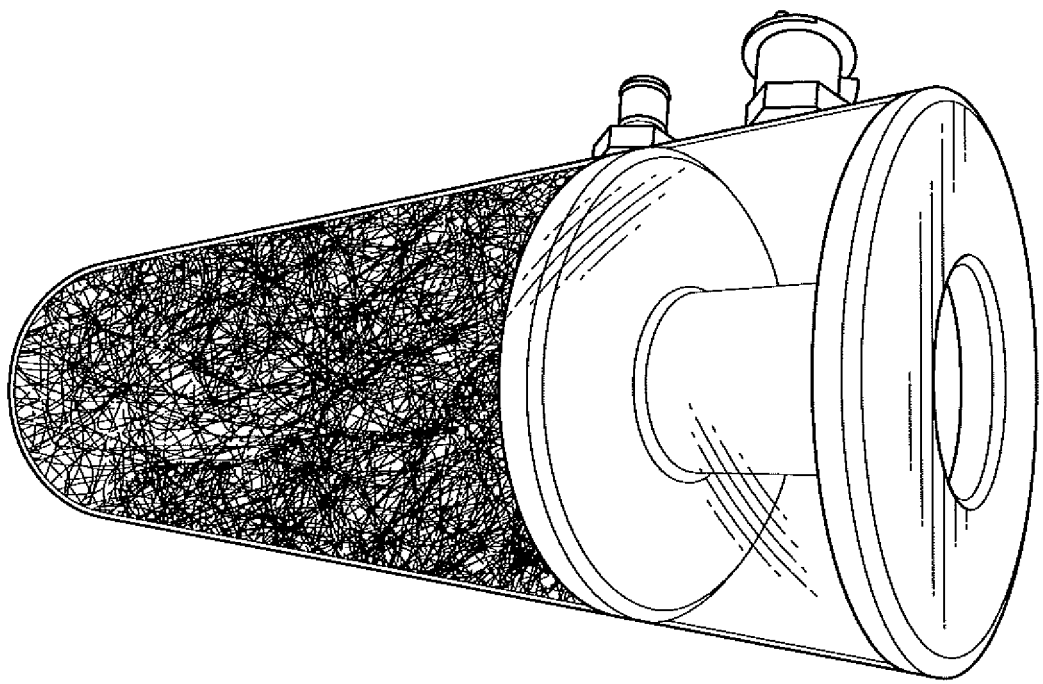
FIG. 46 provides an illustration of an exemplary component according to the present disclosure.

FIG. 46 and FIG. 47 illustrate an exemplary component in operation. FIG. 46 illustrates an alternative view of a disposable component according to the present disclosure, similar to the reusable component shown in FIG. 32. FIG. 47 shows that same disposable component engaged with a subject. As shown in FIG. 47, a portion of the subject's anatomy has been engaged by the device and is drawn (via vacuum application) through the annular space and into the vacuum chamber, thus forming a leak-proof seal between the subject and the device. The subject's urethra (not shown) is now sealably disposed within the urethral engagement conduit, thus placing the subject's urethra (and bladder) into fluid communication with the urine receptacle. As shown in other figures, there may be a heat sink disposed within the urine receptacle FIG. 8 illustrates an alternative component that includes both a UED section as well as a receptacle (labeled "closed air space") into which the subject excretes urine. As shown in the figure, the component includes a vacuum chamber (which may also be termed a "urine trap") and a urethral engagement conduit (not labeled), which conduit leads into the closed air space or urine receptacle. The vacuum chamber suitably includes a vacuum tap, which permits application of vacuum to the chamber. The closed air space also suitably features a pressure tap or other outlet that allows the user to monitor the pressure within the chamber. The pressure tap may also be used to vent air from the receptacle. Not shown—in FIG. 8—is an optional additional tap of the urine receptacle that in turn engages with a valve or other device that permits release or venting of urine or air from the urine receptacle, as described elsewhere herein. In some embodiments, the valve (which may be a solenoid valve or a disposable portion of a solenoid valve) is incorporated into the component. In other embodiments, the receptacle includes a tap or other opening that allows the receptacle to engage with a valve that is controlled by a device. The receptacle may also include a port that allows urine to be dumped or otherwise removed from the receptacle.

Figure 7:
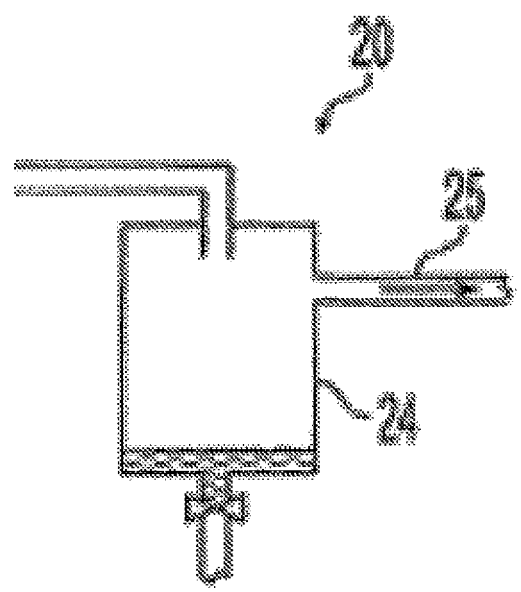
FIG. 7 depicts an exemplary urine receptacle (closed air chamber)

An alternative component is shown in FIG. 7. That component 20 includes a urine receptacle 24 that features a tap 25 that allows for measurement of the pressure within the receptacle 24. The component also includes a valve (bottom of image) that may be configured to release air, urine, or both from the receptacle. As shown in the figure, urine enters from top of chamber. The side-arm leads to a pressure sensor (e.g., a transducer) that triggers a valve at bottom of chamber to release the pressure (by dumping the urine) when a predetermined pressure level is reached (e.g., 80 mm Hg).

The valve then closes and another pressure-flow cycle occurs. These cycles are repeated until the bladder empties and urine flow ceases.

Figure 9:
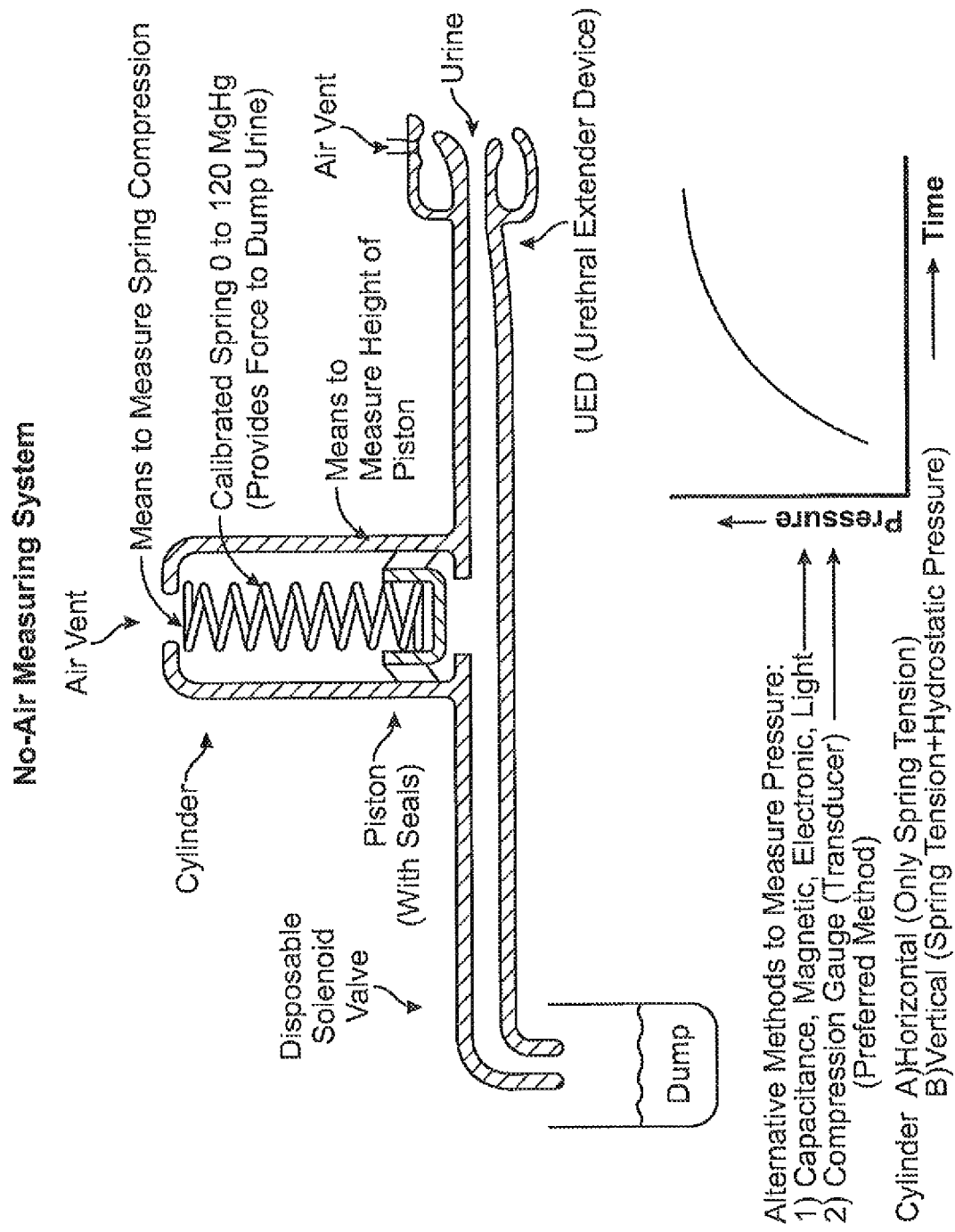
FIG. 9 depicts an exemplary pressure measurement system according to the present disclosure—a spring and/or hydrostatic pressure may be used to provide required back-pressure.

FIG. 9 presents another embodiment of the disclosed technology. On the right-hand side of the figure is a urethral engagement or extender device. Such devices are described elsewhere herein. The pictured device also includes a piston (center of figure) that is configured to measure the pressure within the urine receptacle. As shown, a spring may be used to measure the pressure within the urine receptacle. The device may be configured so as to measure the isovolumetric pressure of the bladder while the receptacle remains closed to the exterior environment during urine entry. The non-air-based pressure measuring system avoids temperature, atmospheric pressure and diabatic issues associated with air-based pressure measuring systems. Thus, FIG. 9 depicts an exemplary pressure measurement system with a fluid-based method to generate time-pressure curves to measure urine flow rate, flow resistance and isovolumetric bladder pressure during micturition.

Components will now be described in additional detail. In some embodiments, a component may comprise a vacuum chamber having an entry opening configured to engage with a subject's anatomy proximate to the subject's urethra, the vacuum chamber having an outlet port configured to engage with a vacuum source. The component may also include a urethral engagement conduit extending into the vacuum chamber, the urethral engagement conduit having a proximal opening configured to engage a subject's anatomy proximate to the subject's urethra, the entry opening of the vacuum chamber and the proximal opening of the urethral engagement conduit defining a gap therebetween, the gap being configured so as to enable passage of the subject's anatomy proximate to the urethra through the gap and into the vacuum chamber upon application of sufficient vacuum, the component being configured to give rise to a leak-proof mechanical seal under vacuum between the proximal opening and the anatomy proximate to a urethra upon application of sufficient vacuum. The component may also include a receptacle in fluid communication with the urethral engagement conduit, the receptacle further comprising a aperture (also termed "tap" in some cases). This aperture may be used to permit monitoring of the temperature, pressure, or both within the receptacle.

The aforementioned gap may comprise a distance (e.g., a radial distance) between an edge of the proximal opening of the urethral engagement conduit and an edge of the entry opening of the vacuum chamber, as shown in, e.g., FIG. 6. This distance is suitably less than about 50 cm, less than about 10 cm, less than about 5 cm, less than about 3 cm, or even less than 1 cm. The gap may also include a vertical distance between a plane of the proximal opening of the urethral engagement conduit and a plane of the entry opening of the vacuum chamber. As one non-limiting example, the proximal opening of the urethral engagement conduit may lie in a first plane, and the entry opening of the vacuum chamber may lie in a second plane. The two planes may be parallel to one another, although this is not a requirement. The vertical distance described above is suitably less than about 50 cm, less than about 5 cm, or less than about 3 cm, or even less than about 1 cm, e.g., 0.1, 0.5, or about 0.7 cm.

Figure 16:
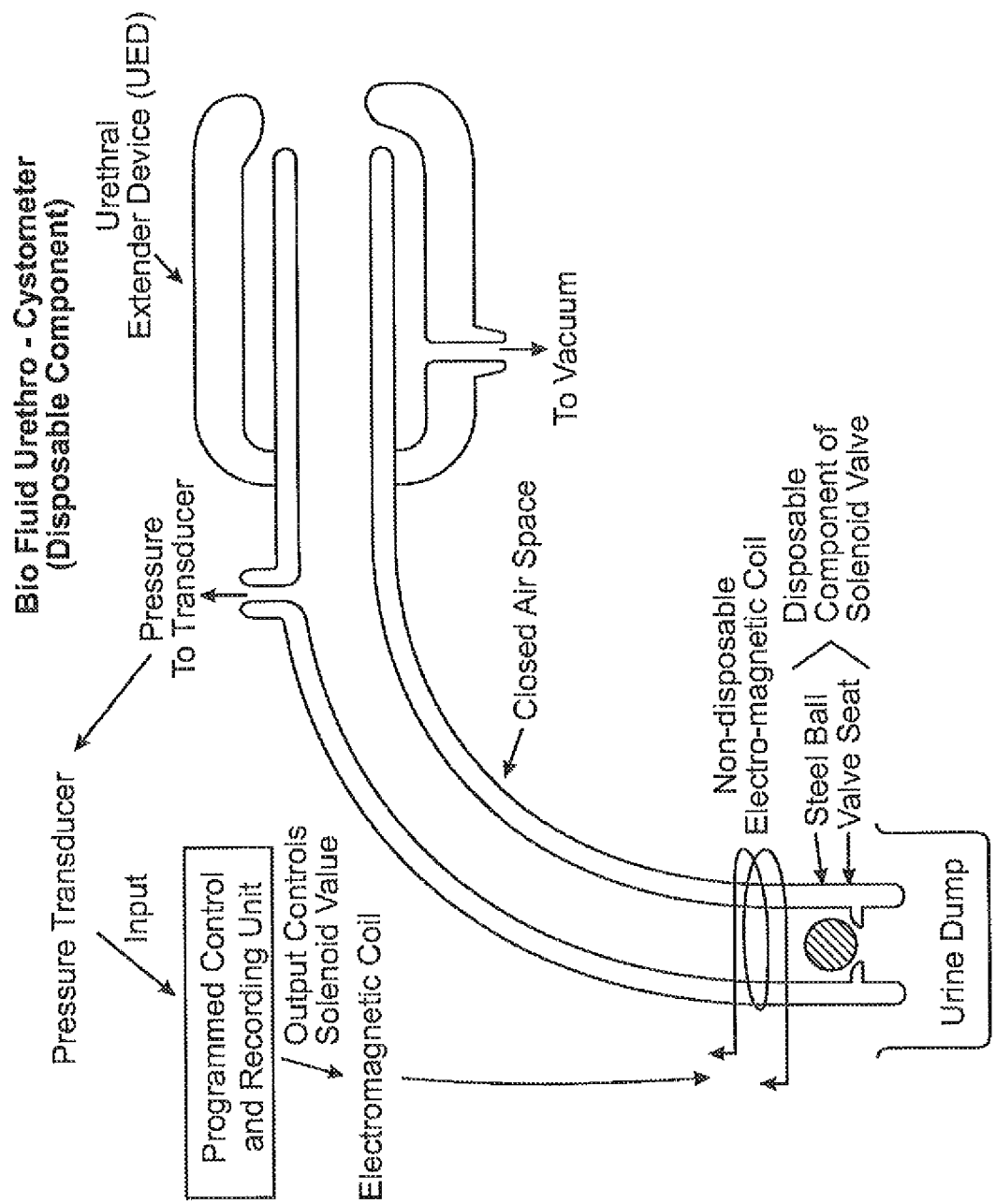
FIG. 16 depicts an alternative embodiment of the disclosed technology that vents urine and features a disposable solenoid valve.

Another exemplary component is shown in the lower right hand image of FIG. 16. As shown there, application of a vacuum draws periurethral tissue (in this case, the glans penis) into the gap between the urethral engagement conduit and the vacuum chamber, thus forming a leak-proof seal between the urethra and the urethral engagement conduit.

This seal in turn places the urethra into fluid communication with the receptacle. As shown in FIG. 16, the openings of the vacuum chamber and urethral engagement conduit may include lips, curls, and the like that may be adapted to maintain the tissue seal. The vacuum applied to the vacuum chamber is suitably less than 300 mm Hg (e.g., 200 mm Hg, 150 mm Hg, 100 mm Hg, 50 mm Hg, 25 mm Hg, and lower), although vacuums above 300 mm Hg may be used in some instances.

As FIG. 16 further shows (upper frame of figure), the urethral engagement region may be suitably connected to a vacuum source configured to apply the seal-forming vacuum. The vacuum source may be a pump or other device that connects to the component, but the component itself may also include the vacuum source. As one example, the component may include a squeeze bulb, a button, or other device configured to apply a vacuum to the vacuum chamber. The urethra is suitably in fluid communication with a receptacle (or "closed air space"), that is sealed to the external environment. A pressure sensor or other sensor is suitably in fluid communication with the interior of the receptacle so as to monitor the pressure within the receptacle. A valve (e.g., a solenoid valve as shown in FIG. 16) is suitably disposed so as to release urine, air, or both from the receptacle. The valve may be manually actuated or actuated in an automated fashion by a controller or other device, such as a computer.

In some embodiments, the proximal opening of the urethral engagement conduit and the entry opening of the vacuum chamber are characterized as being essentially concentric with one another. Openings may be circular in cross-section, but this is not a requirement, as an opening may be elliptical, polygonal, oblong, or otherwise non-circular in cross-section. The openings may overlap with one another, but it is not necessary that the entirety of one opening overlap with the entirety of the other opening, as the openings may be configured so that they are offset from one another. As one example, a component may be configured such that the entirety of the proximal opening of the urethral engagement conduit does not overlap with the entry opening of the vacuum chamber.

In some embodiments, the entry opening of the vacuum chamber defines a first cross-sectional dimension and the proximal opening of the urethral engagement conduit defines a second cross-sectional dimension. A cross-sectional dimension may be a diameter, a radius, a chord, a span, and the like. The first cross-sectional dimension may be in the range of between about 100% and about 500% of the second cross-sectional dimension. In some embodiments, the second cross-sectional dimension is greater than the first cross-sectional dimension by from 0.01% to about 500%. In some embodiments, the first and second cross-sectional dimensions are equal to one another.

The components are suitably constructed of rigid materials, such as polycarbonate, polystyrene, and other polymers. Although not required, at least one of the vacuum chamber or the urethral engagement conduit is suitably transparent or at least partially transparent. The transparency facilitates alignment of the component with the subject and also aids in visualizing the presence—or absence—of urine in the vacuum chamber, receptacle, or both.

The urethra may be aligned with the component in a variety of ways. One way to effect alignment is to apply an inked end of a tube having suitable proper dimensions to the tip of the penis to create a circular mark to center the component on the glans penis. A transparent component can facilitate this alignment. Alternatively, a component may feature a guide (integrated or removable), such as a funnel or other projection that places the urethra into proper register with the component. As described elsewhere herein, the disclosed technology is not limited to use on males, and may be used on females as well as animals.

The component may be formed as a single piece, but the component may also comprise an assembly of two or more pieces. It should also be understood that although a component may comprise a single material (e.g., a component made entirely from polycarbonate), a component may comprise two or more materials. As one example, the urethral engagement conduit might be formed from polyethylene, and the vacuum chamber might be formed from polycarbonate.

In some embodiments, at least one of the vacuum chamber and the urethral engagement conduit comprises a deformable material, such as a silicone, a polyurethane, and the like. A deformable material may assist in the component engaging with the subject.

The proximal opening of the urethral engagement conduit and the entry opening of the vacuum chamber may be fixed in position. Alternatively, at least one of the proximal opening of the urethral engagement conduit and the entry opening of the vacuum chamber is capable of motion relative to the other. The relative motion may be effected by advancing (e.g., sliding or screw-advancing) the proximal opening of the urethral engagement conduit relative to the entry opening of the vacuum chamber, by withdrawing the proximal opening of the urethral engagement conduit relative to the entry opening of the vacuum chamber, or both. At least one of the urethral engagement conduit and the vacuum chamber may be lockably mounted, i.e., may be mounted so that it can be moved and then fixed into position. In this way, the user may vary the size of the opening to the vacuum chamber through which the user's anatomy passes.

Figure 49:
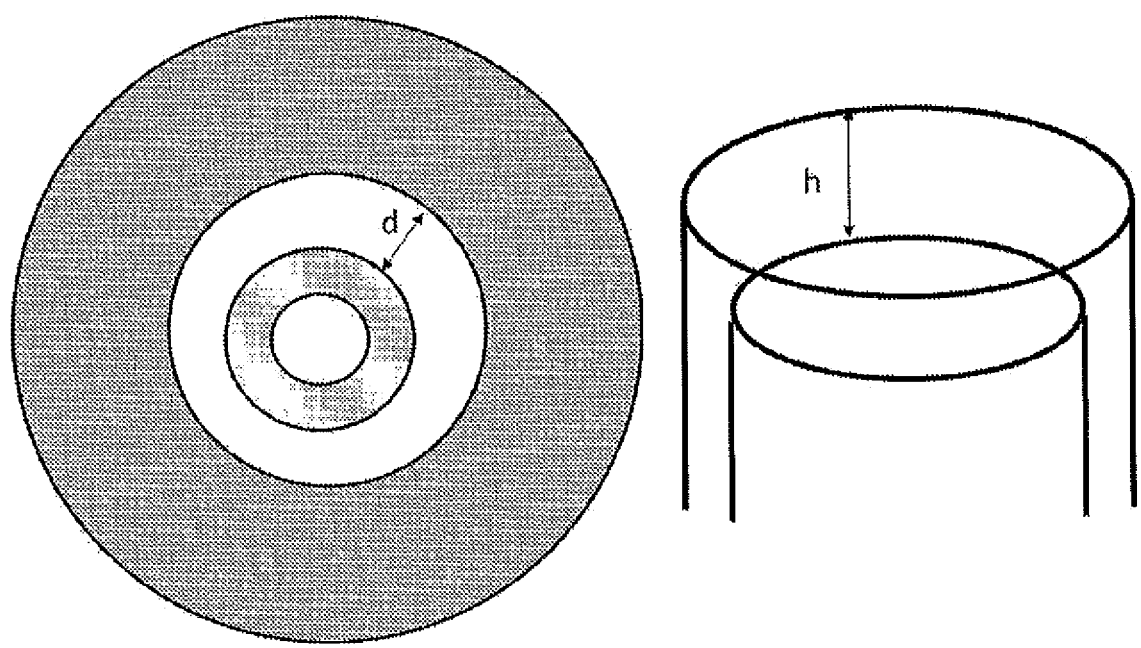
FIG. 49 depicts the portion of an exemplary component that engages with the subject's anatomy.

This is depicted in FIG. 49, which figure depicts an exemplary component according to the present disclosure. The left-hand image of the figure shows an end-on view of the component, with a distance d between the inner ring (i.e., the urethral engagement conduit, shown with dotted fill) and the outer ring, which is the portion of the component that is proximate to the user and against which the user's anatomy may rest (shown with solid fill). As shown in the image, there is a space between these two elements, and this space is the space into which a subject's anatomy is drawn into the vacuum chamber. The space may be annular as shown in FIG. 49, but annular spaces are not required, as the space may be oblong, slit-shaped, or some other configuration. It should also be understood that there may be one, two or more spaces defined between these elements. The separation d shown in FIG. 49 is the distance between the two elements, and may be in the range of from about 0.01 mm to about 1 cm, to about 5 cm, about 10 cm, or even about 50 cm, in some embodiments. Values of d between about 0.1 cm and about 2 cm are considered especially suitable, but are not essential.

FIG. 49 also shows—right-hand panel—a vertical separation h between the urethral engagement conduit (the lower of the two elements in the figure) and the proximate portion of the component. As described elsewhere herein, the distance h may be varied by relative motion of the urethral engagement conduit and the proximal portion of the component; this motion may be accomplished, for example, by advancing the urethral engagement conduit toward or away from the proximal portion of the component. The distance h may be in the range of from about 0.01 mm to about 1 cm, to about 5 cm, about 10 cm, or even about 50 cm, in some embodiments. Values of h between about 0.1 cm and about 2 cm are considered especially suitable, but are not essential.

Figure 48:
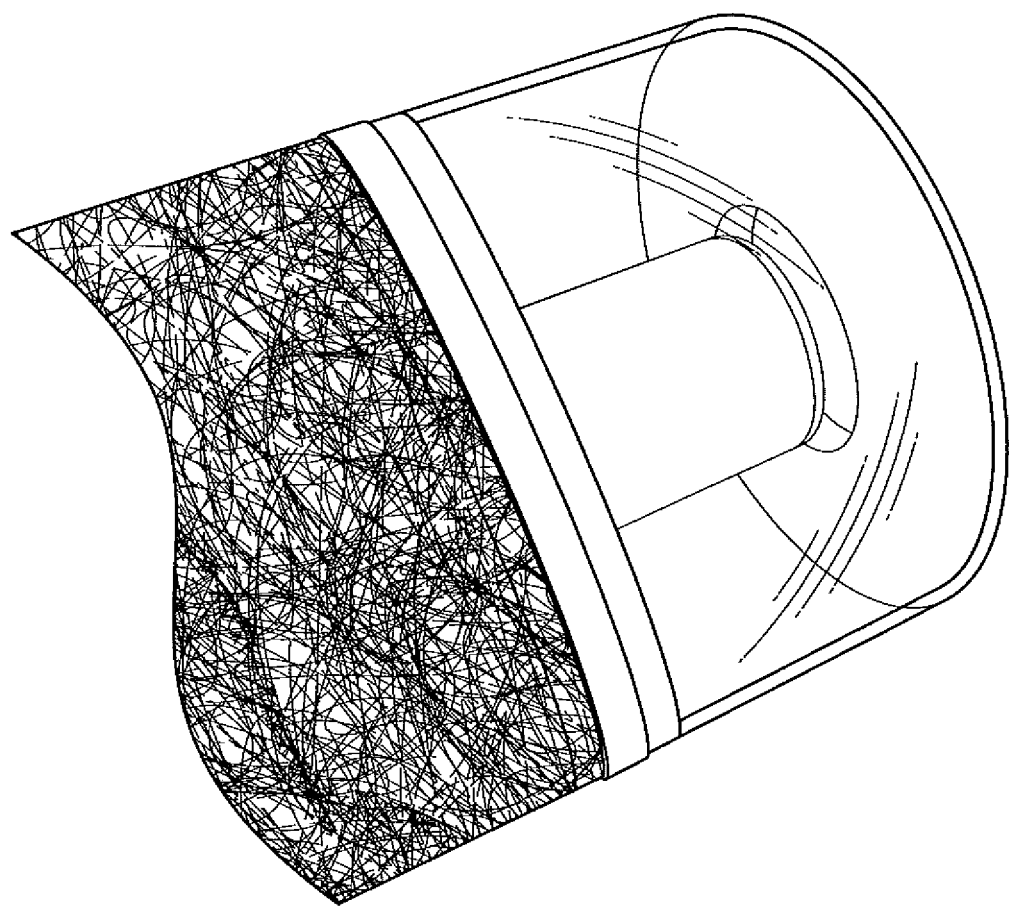
FIG. 48 illustrates a component according to the present disclosure.

In some exemplary embodiments, (e.g., FIG. 35 and FIG. 48), the opening into the vacuum chamber is donut-shaped in cross-section. As shown in the figure, the size of the opening may be changed by relative motion between the portion of the vacuum chamber against which the subject's anatomy rests and the proximal opening of the conduit.

The entry opening of the vacuum chamber suitably has a cross-sectional dimension (e.g., diameter) in the range of from about 0.1 cm to about 10 cm, about 50 cm, or from about 0.5 to about 5 cm, or even from about 1 cm to about 2 cm. The proximal opening of the urethral engagement conduit may have a cross-sectional dimension in the range of from about 0.1 cm to about 3 cm, or from about 0.5 cm to about 1 cm.

In certain embodiments, the entry opening of the vacuum chamber, the proximal opening of the urethral engagement conduit, or both, defines an adjustable cross-sectional dimension. A cross-sectional dimension may be adjusted by an iris-type opening, by an opening formed in a deformable material, and the like. A component may have a proximal portion (with an aperture) that is removable and that can be replaced with a proximal portion that has an aperture of different sizes.

The receptacle suitably has an interior volume in the range of from about 0.1 ml to about 100,000 ml, or from about 1 ml to about 1000 ml, or even from about 20 ml to about 500 ml.

The components may be designed so as to have a weight of less than about 10 kg, less than about 5 kg, less than 1 kg, or even less than 0.5 kg.

The component may be cylindrical in form, but this is not a requirement. The component may have an external cross-sectional dimension (length, width, diameter, radius) in the range of from about 1 cm to about 100 cm, or from about 10 cm to about 25 cm. Components sized to be handled by a single technician are considered especially suitable. The component may include a handle, ridges, or other surface feature configured to assist in handling the component.

A component may also include a heat-absorbing material, which material may be disposed in, on, or around the receptacle. Suitable heat-absorbing materials include metals (e.g., copper, brass, steel), glasses, and the like. Materials in "wool" or fibrous form—such as steel, copper or glass wool—are considered especially suitable for the disclosed components. The heat-absorbing material may be solid, but may also be a foam or otherwise include pores, voids, and the like. Liquid heat-absorbing materials are also considered suitable. Fibrous materials—such as glass wool—are especially suitable for use in the disclosed components. The heat absorbing material may also be disposed such that the material is in thermal communication with the interior of the receptacle. As one non-limiting example, the heat-absorbing material may be disposed on the outside of the receptacle. One or more conducting structures—e.g., a rivet—may be used to place the interior of the receptacle into thermal communication with the exterior of the receptacle or even with a heat-absorbing material that is exterior to the receptacle.

Components may, in some embodiments, include a valve that is configured to place the interior of the receptacle into fluid communication with an environment exterior to the interior of the receptacle. The valve may be disposed at the receptacle aperture. It should be understood that the receptacle aperture may be used to place the interior of the receptacle into fluid communication with a valve exterior to the receptacle or to a pressure sensor exterior to the receptacle. The valve may be a solenoid valve, a butterfly valve, or other type of valve. The valve may be manually actuated, but is also suitably actuated be an automated device. One such example is shown in FIG. 9, which shows a solenoid valve integrated into a component according to the present disclosure. The solenoid shown in FIG. 9 is shown for illustrative purposes only, as other kinds of valves (butterfly, ball, and the like) can be used.

Components may, as described elsewhere herein, also include a vacuum device in fluid communication with the outlet port of the vacuum chamber. Suitable vacuum devices include hand pumps, squeeze bulbs, motorized devices (e.g., vacuum pumps) and the like. The vacuum device is suitably manually-actuated, but may also be automated or even self-powered.

In some embodiments, the disclosed components include a pressure sensor capable of fluid communication with the interior of the receptacle, a temperature sensor capable of thermal communication with the interior of the receptacle, or both. In some embodiments, the pressure sensor, the temperature sensor, or both, is comprised in a transmitter device. As one such example, the transmitter device may be an RFID device or other device capable of transmitting data (e.g., pressure readings) from the component sensor to a receiver or other device. In this way, a component may collect temperature, pressure, or other information and then provide that information to a user.

Components according to the present disclosure may also include a compliant structure configured to deform in response to the presence of fluid in the receptacle. Such a structure may be a balloon, a spring-actuated structure, a deformable membrane, a column of fluid, or any combination thereof. FIG. 9 presents one such component. As shown in FIG. 9, a spring is in fluid communication with the interior of the receptacle, and increasing pressure in the receptacle acts to compress the spring. Compression of the spring may then be correlated to a pressure within the receptacle.

FIG. 10 presents another alternative embodiment. As shown in that figure, urine may enter (left side of figure) a receptacle. The receptacle may be kept closed (i.e., sealed) to the external environment (by keeping the valve at the right side of the figure) closed so as to effect urination into an closed system. As urine enters the component, the atmosphere inside the closed component exerts against the accordion-type reservoir, which in turn exerts against a spring. The spring (in a vented chamber) in turn compresses against a sensor, which in turn reports a value that represents the instantaneous pressure within the receptacle. Although the valve in this figure is configured to release urine from the receptacle, it should be understood that a valve may be positioned or otherwise configured (e.g., by placing the valve at the top or headspace of the receptacle) so as to release air from the receptacle. The disclosed components may use either an air or non-air based pressure measuring system. The use of an air-based system may benefit from compensation or control over temperature, atmospheric pressure and diabatic effects, although this is not a requirement.

Exemplary pressure vs. time curves are shown at the bottom of FIG. 10. As shown, each curve shows an increase in pressure within the component while the component is closed to the exterior environment, followed by a decrease in pressure to zero (i.e., atmospheric pressure) when urine, air, or both are released from the system by way of the valve being actuated. The valve then closes during urination to re-seal the receptacle against the exterior environment, and the pressure within the receptacle again rises. The cycle may then be repeated during urination.

As described elsewhere herein, the air, urine, or both may be released when the pressure within the receptacle reaches a maximum value. The maximum value will represent the maximum pressure achieved by the subject's urine flow, which also represents the maximum pressure the subject's bladder achieves. This maximum pressure may be determined by monitoring the pressure within the receptacle. Alternatively, the air, urine, or both may be released when the pressure within the receptacle reaches a predetermined value (e.g., 30 mm Hg) that may be less than the maximum. Although this is not a requirement, this approach has the advantage of reducing or eliminating potential discomfort experienced by the subject from painful stretching of the distal urethra which is not accustomed to exposure to high isovolumetric bladder pressures. Curve-fitting techniques and other methods of calculation (described elsewhere herein) can be used to calculate or estimate a maximum bladder pressure from a pressure vs. time curve (e.g., a curve gathered from permitting the subject to urinate into the receptacle and then releasing urine or air from the receptacle when the receptacle reaches some predetermined internal pressure e.g., 40 mm Hg) that does not include the maximum pressure. Also as shown in FIG. 10, a user may include a correction for diabatic effects in the pressure vs. time curves.

A component may also include a flow resistance device capable of fluid communication with the urethral engagement conduit. The component will have its own inherent flow resistance (e.g., by virtue of the air contained in the component), but may also include a further flow resistance device. Such a device may be a capillary, a membrane, or other flow resistor. The flow resistance device may have a variable flow resistance. As one such example, the flow resistance device may include a valve, obstruction, constriction, or other aspect that may be manipulated to as to vary the flow resistance of the device. In the case of the air filled receptacle (i.e., the UED closed air chamber) the resistance to urine flow into the UED is provided by the back-pressure created by the compliance of air (or other gas) under compression from the urine entering the closed chamber. This behavior is consistent with the gas laws. In the case of the urine venting UED the air volume within the air chamber at atmospheric pressure remains the same from one pressure-time curve to the next, so air compliance (and resistance to flow) remains the same throughout the test. However, with the air venting UED, the urine displaces a given volume of air from the closed air chamber with each pressure-time curve, and compliance of the remaining air at atmospheric pressure decreases (and resistance to flow increases) from one pressure-time curve to the next.

The present disclosure also contemplates that the component (e.g., the receptacle) may have a fluid or solid or gas disposed within. The fluid may be water, alcohol, artificial urine, an antiseptic, or other fluid. The fluid may be used to calibrate the UED, establish a vapor pressure, a humidity, or other condition within the component. The solid may be a heat sink (as described elsewhere) or a space occupying solid to change the volume of the closed air space or to calibrate the UED. The component may also include a conductive material that provides heat to the component. This may be in the form of a metallic band that surmounts at least a portion of the component, which metallic band may be heated so as to heat the component. A component may accordingly be adapted to be heated before use, e.g., to be heated to body temperature, as with a laboratory oven or other heating device. A component may even include a resistor (e.g., wire) configured to supply heat to the device. A component may also contain within (e.g., be pre-loaded with) a gas, such as water vapor, alcohol vapor, or other gases so as to provide a vapor pressure within the component.

Using induction heating with the steel wool heat sink will permit rapid, smooth and easily regulated heating of the closed air space within the disposable. The greater the mass of the heat sink, and the greater the voltage/current, the quicker the increase in temperature and the better the stability in temperature after the current is turned off A component may include a vacuum chamber that defines an interior volume in the range of from about 0.01 ml to about 100 ml, about 500 ml, or even about 1000 ml. It should be understood that a component may, in some embodiments, comprise a vacuum chamber without a urine receptacle. As one such example, a component might include an annular or doughnut-shaped vacuum chamber that itself has a circular opening. Such a component may be used to releasably attach to, for example, the surface of the beating heart to stabilize the operative field during coronary artery procedures. Alternatively, such a component may be used to releasably attach to tissue such as skin, blood vessels, cardiac tissue, or other forms of tissue, in a manner akin to stretching material across the frame of a tambourine. In this way, the component fixes and immobilizes tissue so as to stabilize that tissue within the patient and to enhance the ability of surgeons to operate on or around the stabilized tissue.

Figure 28:
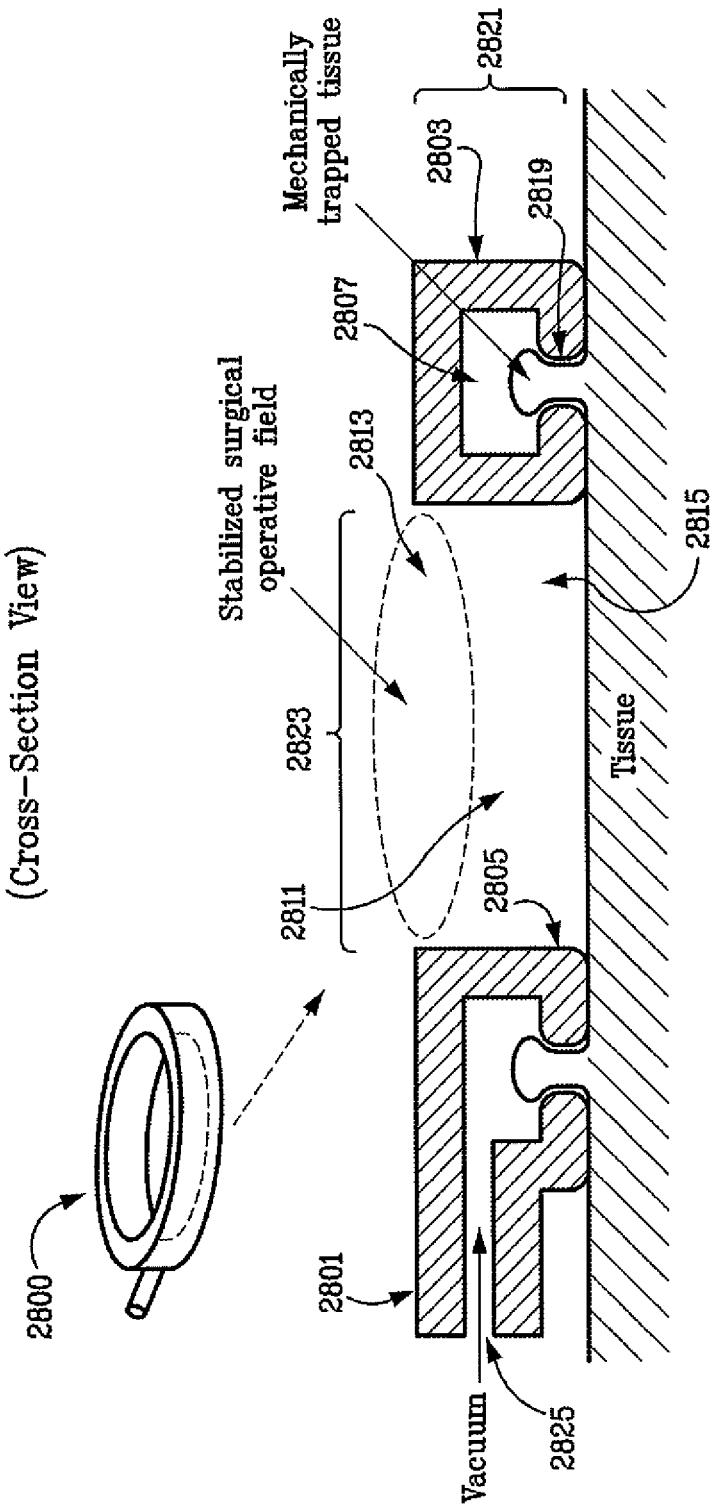
FIG. 28 illustrates a cross-section of a component stabilizing tissue in a surgical application.
Figure 54:
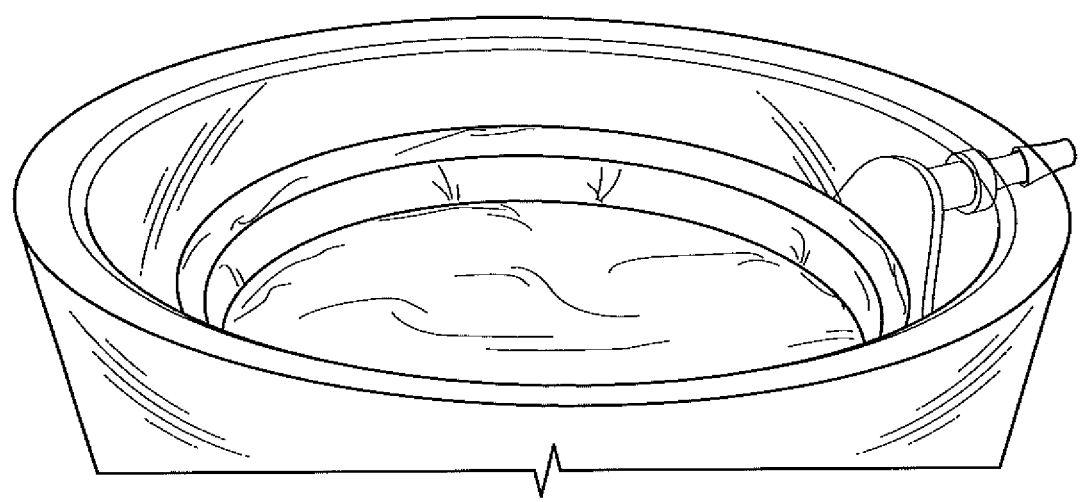
FIG. 54 illustrates a surgical stabilizer according to the present disclosure.

As shown in FIG. 28, a region of the tissue is stabilized by virtue of the tissue being drawn into the vacuum chamber. A component may be attached to a bracket or brace; in this way, when the component attaches to the heart or other tissue, it also acts to attach—and even immobilize—the heart or other tissue to the bracket or brace. The vacuum mechanically traps tissue, which trapping yields a mechanically stabilized region of the tissue that can be more easily (and safely) operated upon. Relieving the vacuum in turns allows the tissue to be released from the component. As described elsewhere herein, the stabilized region of tissue need not necessarily be round, as it may be square, triangular, oblong, or some other shape. An additional view is shown in FIG. 54. That figure shows a stabilizer engaged with the skin of a patient, showing the skin being drawn up into the annular vacuum chamber of the stabilizer, with additional skin being held in tension across the "hole" of the annular stabilizer device. The vacuum port is shown at the right-hand side of the image, showing a vacuum tube connected to the port of the device so as to provide a vacuum to the vacuum chamber of the stabilizer device. It should be understood that the annular device shown in FIG. 54 is exemplary only and does not limit the shape of the device, as devices may be square, oblong, or some other shape.

The component may be sized so that it defines a cross-sectional dimension (or even a maximum cross-sectional dimension) of from about 0.01 cm to about 50 cm, or less than 10 cm, less than 5 cm, or even less than 2 cm. For example, the component may have a diameter (defined by the inner diameter of the inner ring of the device) of about 3 cm and a height of about 0.5 cm. The component may be configured and sized to as to be insertable into a patient by way of an incision or even a so-called keyhole incision. The component may also comprise a deformable material so that at least a portion of the component may be compacted or otherwise folded to ease insertion into a patient and to ease transit within the patient to the desired location. The component may include a deformable material and a rigid material, in some embodiments. A device may be configured so that it expands or otherwise opens once inserted into a patient. In some embodiments, a component may be fabricated of subcomponents that are connected or otherwise assembled with one another once they are placed within a subject. A component may be constructed so it takes on a curved or other shape within a patient, as needed. The devices may be constructed such that their shape, curvature, or other characteristic may be adjusted while the device is inside of a patient; i.e., be adapted to the operative field in terms of curvature and shape. The component may also be connected to a flexible or rigid conduit or other connection that provides the vacuum to the component once the component has been inserted into the patient. The component may also be connected to another component, device, or connection that holds the component in place. Once the component is positioned, the user may apply a vacuum (suitably less than about 300 mm Hg, 100 mm Hg, 50 mm Hg, 10 mm Hg, or even less than about 5 mm Hg) so as to affix the component to the tissue of interest. The vacuum connection may define a cross-sectional dimension (e.g., diameter, radius) in the range of from about 0.01 mm to about 10 mm or even about 50 mm. The component may also be positioned so as to—when vacuum is applied—seal or otherwise clamp off a blood vessel or other structure. It should be again understood that the opening of the vacuum chamber may be circular, but may also be of another shape, such as square, oblong, elliptical, or other shape.

Figure 26:
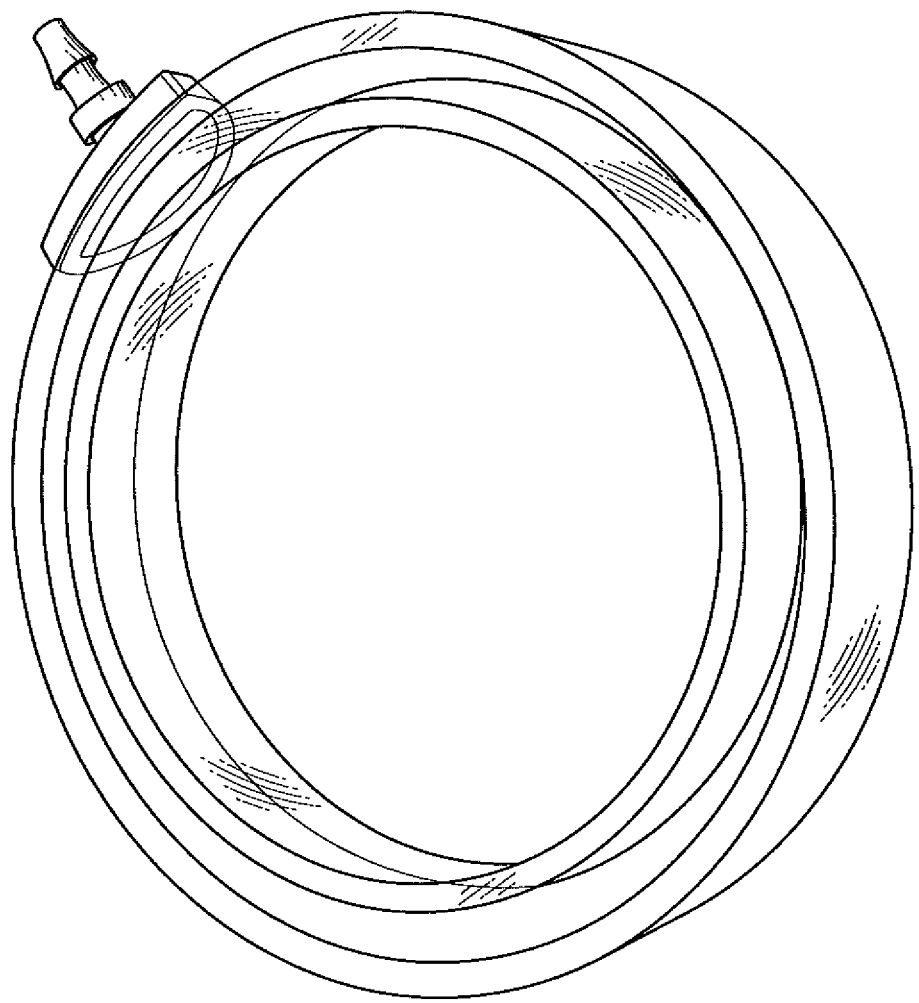
FIG. 26 illustrates an exemplary component suitable for stabilizing tissue in surgical applications.
Figure 27:
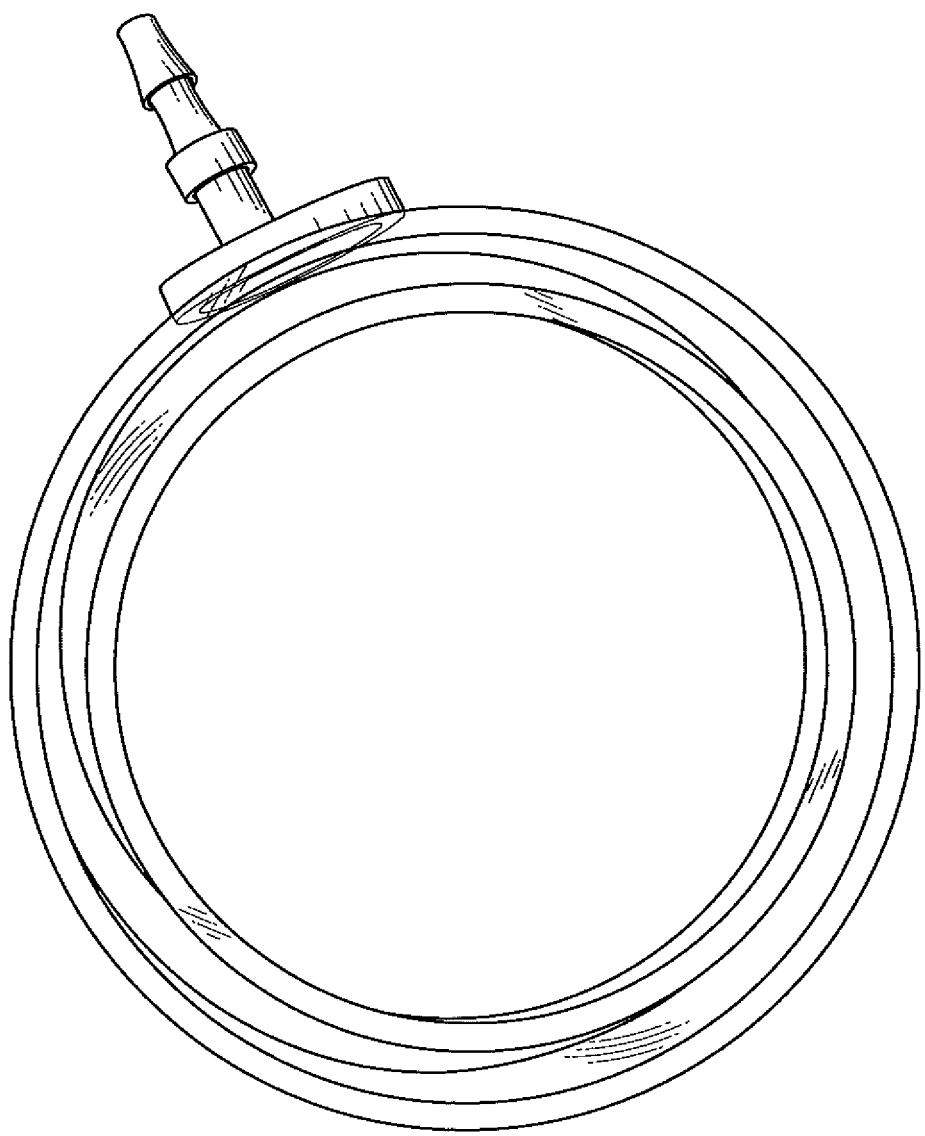
FIG. 27 illustrates an exemplary component suitable for stabilizing tissue in surgical applications.
Figure 29:
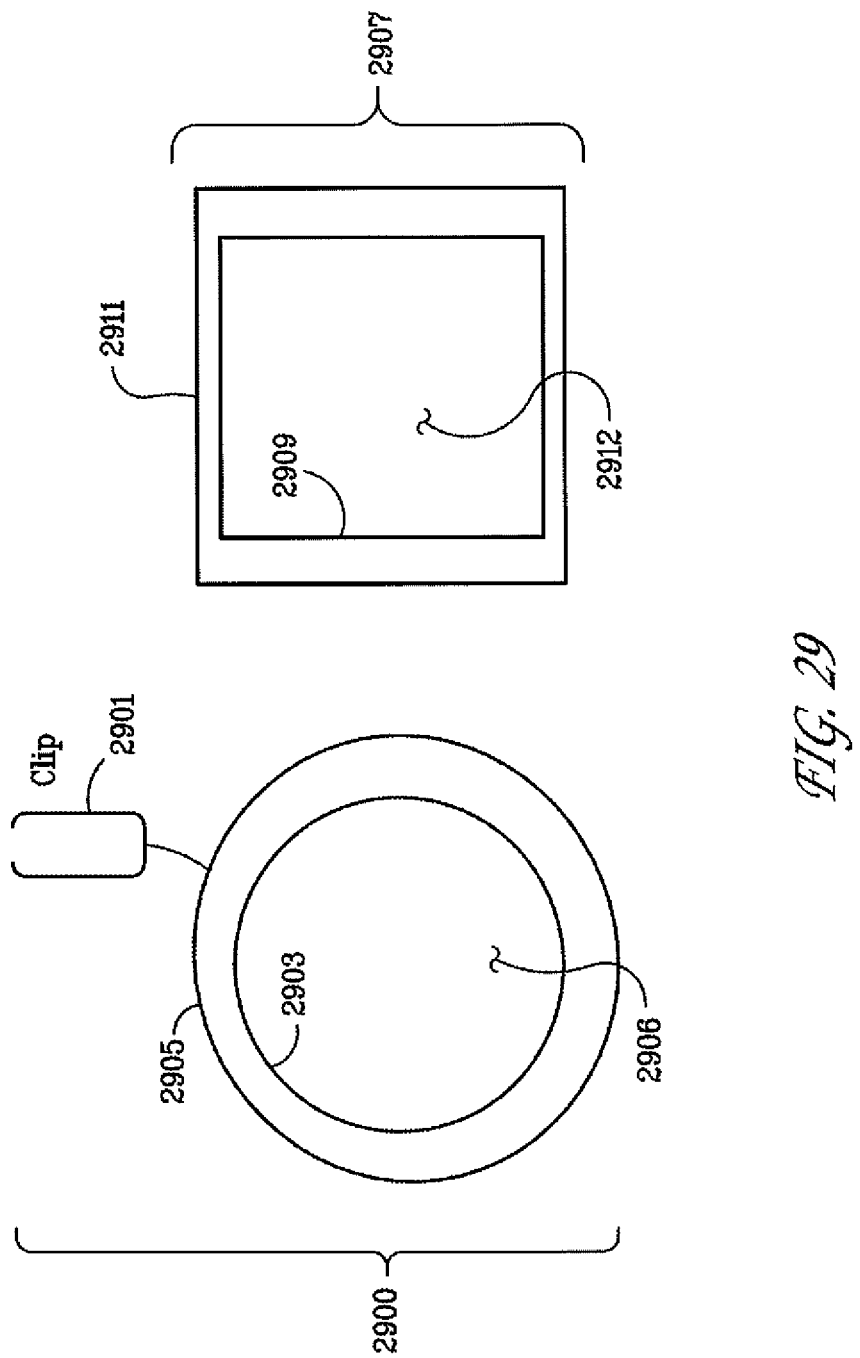
FIG. 29 illustrates various configurations for components used in surgical applications.

Exemplary devices (not necessarily to scale) are shown in FIG. 26 and FIG. 27. As shown in those figures, a component may be annular in shape. A tap (outlet) is formed in the device so as to connect the vacuum chamber to a vacuum source. The devices shown in these figures have an annular gap into which the tissue is drawn. An annular gap is not a requirement, as the gap may be slots (e.g., opposed slots), a square, a triangle, and the like, as shown in FIG. 29. The device may even include only a single gap or slot into which tissue is drawn.

The component may include a first opening to the vacuum chamber and a second opening to a tissue aperture; as described above, the tissue is suspended and fixated across the tissue aperture. The first opening may have a cross-sectional dimension in the range of from about 0.1 cm to about 10 cm or even about 20 cm. The second opening may have a cross-sectional dimension in the range of from about 0.1 cm to about 10 cm or even about 20 cm. The first opening is suitably larger than the second opening, although the two openings may be of the same size. As described elsewhere herein, the component may define a gap between the two openings, which gaps are described elsewhere herein.

These disclosed components have application in, e.g., cardiac surgery. The heart-lung machine permits temporary paralysis of the heart muscle and provides a relatively blood-free operative field, thereby facilitating the surgical repair of coronary vessels, valves and congenital cardiac defects. However, there are draw backs to the heart-lung machine, mostly related to adverse effects on the CNS. Alternative methods include mechanically immobilizing the beating heart. When heart surgery is performed without using the heart-lung machine there are fewer intra-operative complications and less post-operative morbidity. A number of mechanical devices have been developed to immobilize the portion of the heart undergoing surgery. These large and complicated devices require the chest to be opened as in heart-lung procedures, and they squeeze the heart, resulting in muscle damage and reduced cardiac output.

Computerized methods have been developed to permit keyhole surgery on the beating heart. The surgeon sits at a console, observing the patient's heart on his video screen while manipulating the surgical instruments by remote control. The computer moves the instruments in sync with the heart movements so the surgeon can operate as if the heart was not beating. The use of key-hole surgery further reduces post-operative complications and recovery time, but the technology is complicated and fraught with danger. An improved method for immobilizing the heart that would also facilitate key-hole surgery is to be desired.

Figure 38:
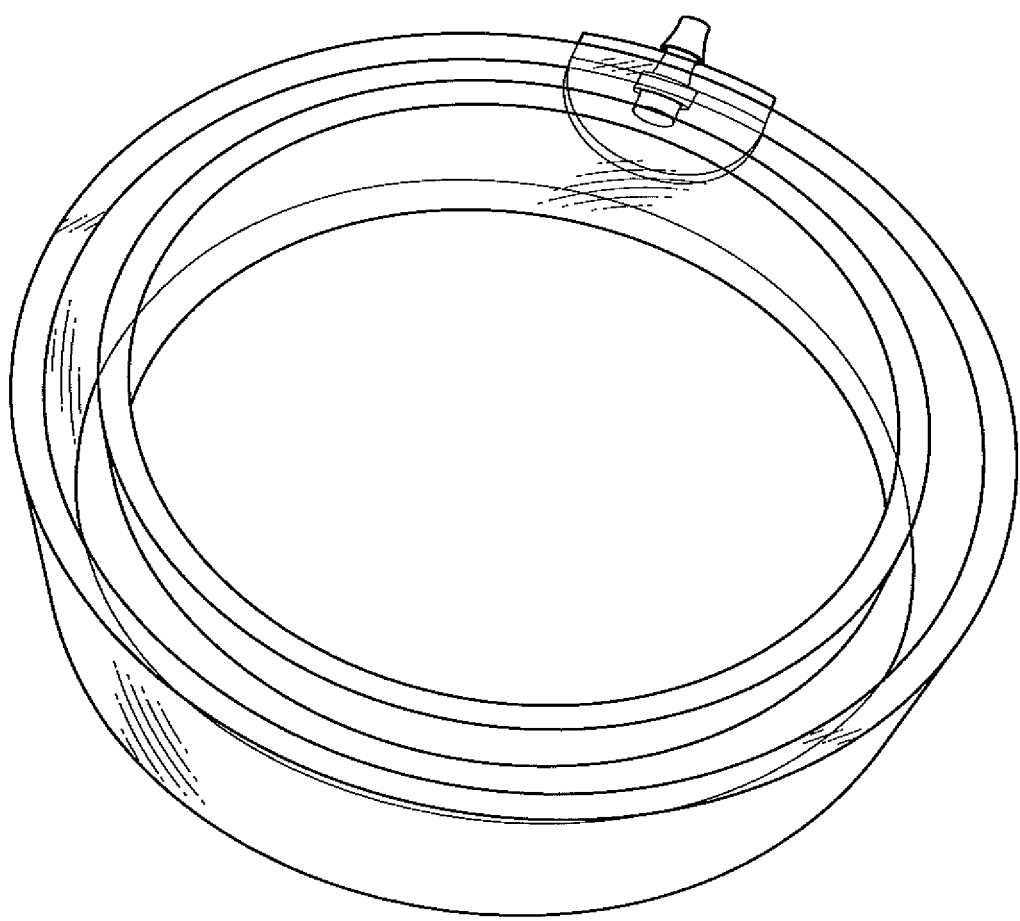
FIG. 38 provides an illustration of a surgical tissue stabilizer according to the present disclosure.

The disclosed components address this problem by enabling mechanical fixation of the area of the heart to be operated upon, but without compromising cardiac output or traumatizing the heart muscle. The device can be used in either open chest or key-hole procedures. This technology method will result in fewer CNS complications (e.g., embolism and stroke) than found with the heart-lung machine. It also facilitates microsurgical vascular and valvular repair procedures by physically immobilizing the beating heart without compromising cardiac output or traumatizing the heart muscle. An additional image is shown in FIG. 38, which figure illustrates an exemplary tissue stabilizer. As shown in the figure, such a stabilizer may include an inner ring and an outer ring that define a space therebetween. A vacuum port is then used to apply a vacuum to the space therebetween so as to draw the subject's tissue into that space and to stabilize the tissue circumscribed by that space. The exemplary component shown here is circular in configuration, but other shapes—e.g., any polygon, oval, and the like—may be used as well. In one exemplary embodiment, the component may be toroidal in configuration, as shown in FIG. 38. The tissue-engaging edges of the component may be curved, beveled, or squared, depending on the needs of the user. As explained elsewhere herein, the component may include one or more flexible regions so as to facilitate deployment of the component on the subject. If needed, multiple devices may be applied to an organ, such as a beating heart, to stabilize the organ as well as the local tissue.

In addition, a component may include an extension configured to reduce blood flow when the component is engaged with a subject. Such an extension may be a clip, a bar, a spring, or other similar structure that may reduce blood flow (e.g., by at least partially closing off a blood vessel) in the region nearby to the device. As one non-limiting example, the component may include a clip that closes off a blood vessel that is upstream or otherwise nearby to the component when the component is deployed in the patient. The extension may thus be used to reduce or eliminate blood flow at or around the tissue being stabilized.

Systems

Figure 58:
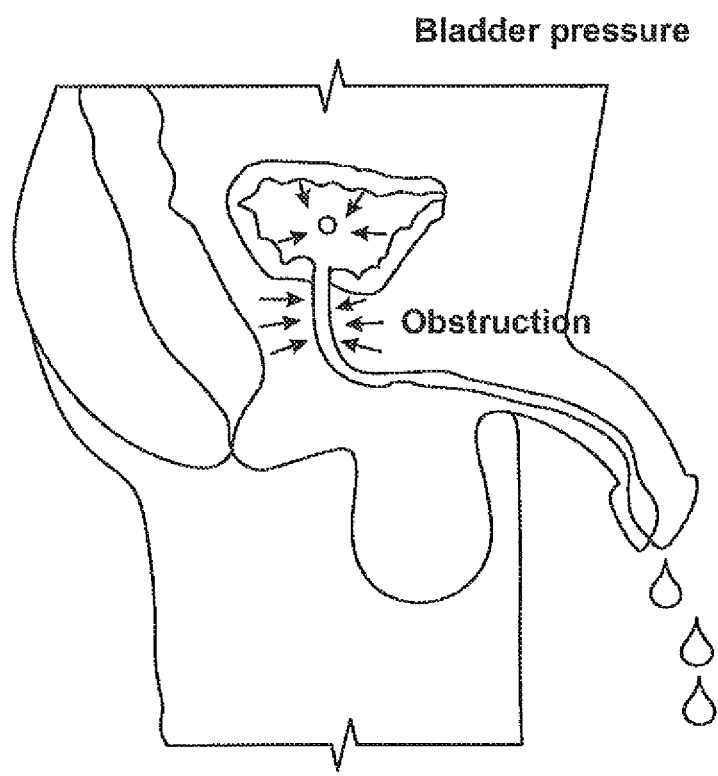
FIG. 58 provides a depiction of the lower urinary tract.

The present disclosure provides systems. The systems may include, e.g., an apparatus (e.g., an instrument) for flow and pressure measurement and control, which may be termed the Flow and Pressure Measurement and Control (FPMC) system. An FPMC may include systems for controlling and measuring instantaneous urine flow rate (uroflowmetry) and bladder isovolumetric pressure (urodynamics). The apparatus is controlled by, and the output recorded by, a subsystem consisting of a computer with appropriate system control and data acquisition hardware and software. At the conclusion of each test, the computer performs a data analysis and parameter calculation program, which solves flow model equations to provide readout of contribution of urethral obstruction (e.g., bladder outlet obstruction due to BPH)) and bladder weakness to the observed urinary tract dysfunction. As described elsewhere herein, FIG. 58 provides a depiction of the lower urinary tract and of the bladder- and obstruction-related causes of LUTS.

Figure 39:
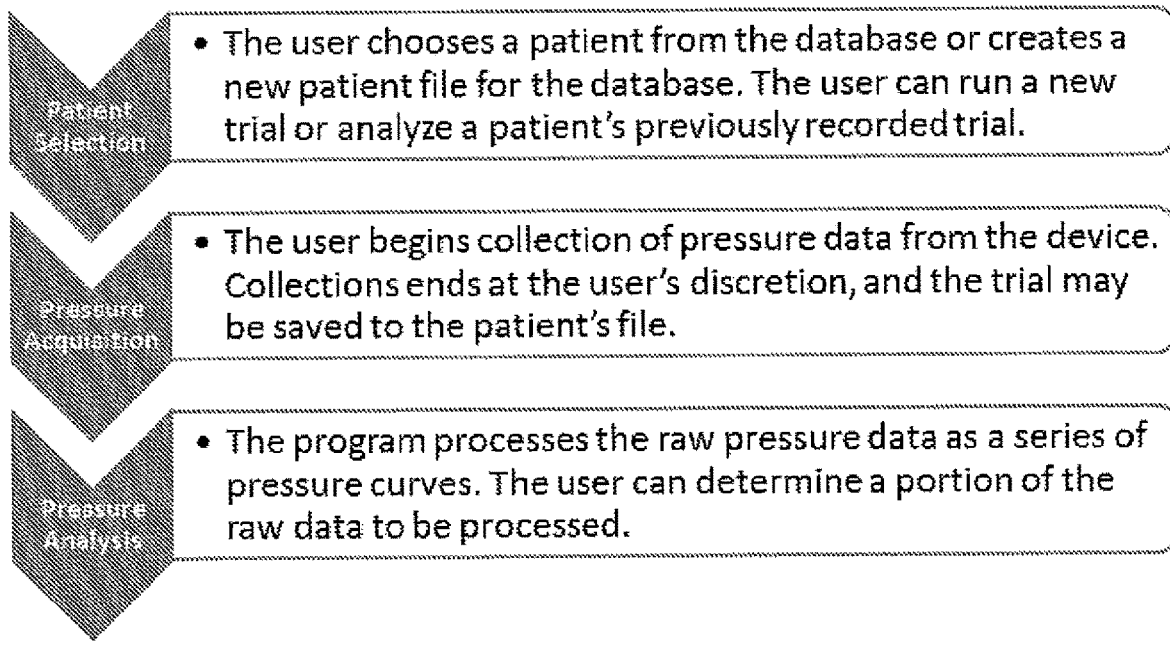
Figure 40:
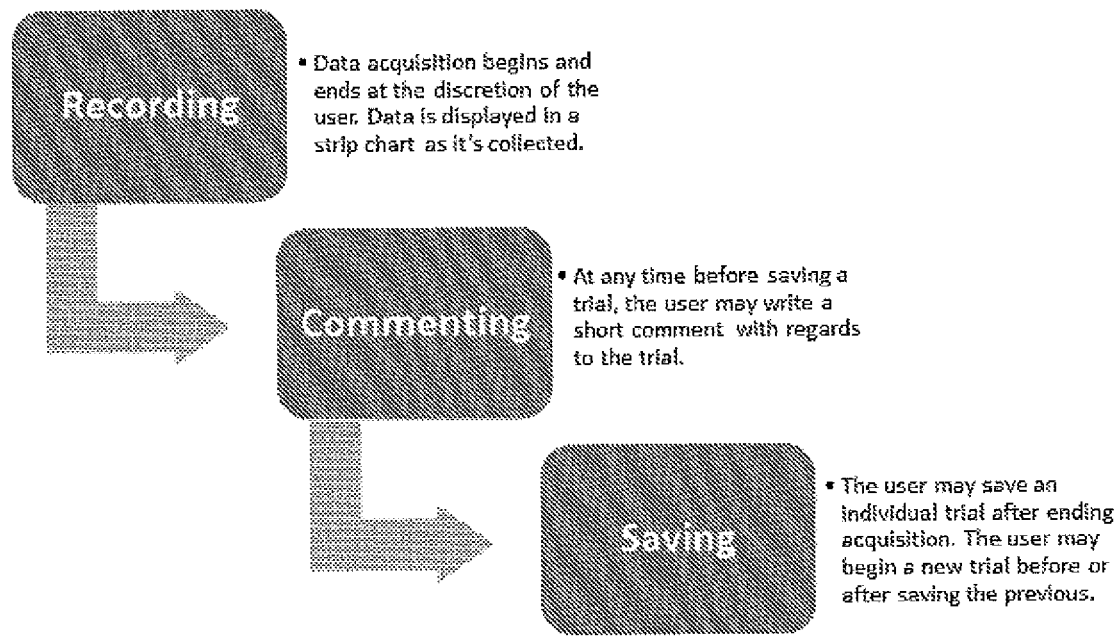

FIGS. 39-45 depict exemplary operation of an FPMC system. FIG. 39 provides an exemplary flow of information. In that figure, a user may (1) choose a patient from the database or creates a new patient file for the database. The user can run a new trial or analyze a patient's previously recorded trial; (2) begin collection of pressure data from the device. Collections ends at the user's discretion, and the trial may be saved to the patient's file; and (3) process the raw pressure data as a series of pressure curves. The user can determine a portion of the raw data to be processed. FIG. 40 depicts an exemplary information-flow for pressure, showing how a user may record, comment, and save the data.

Figure 41:
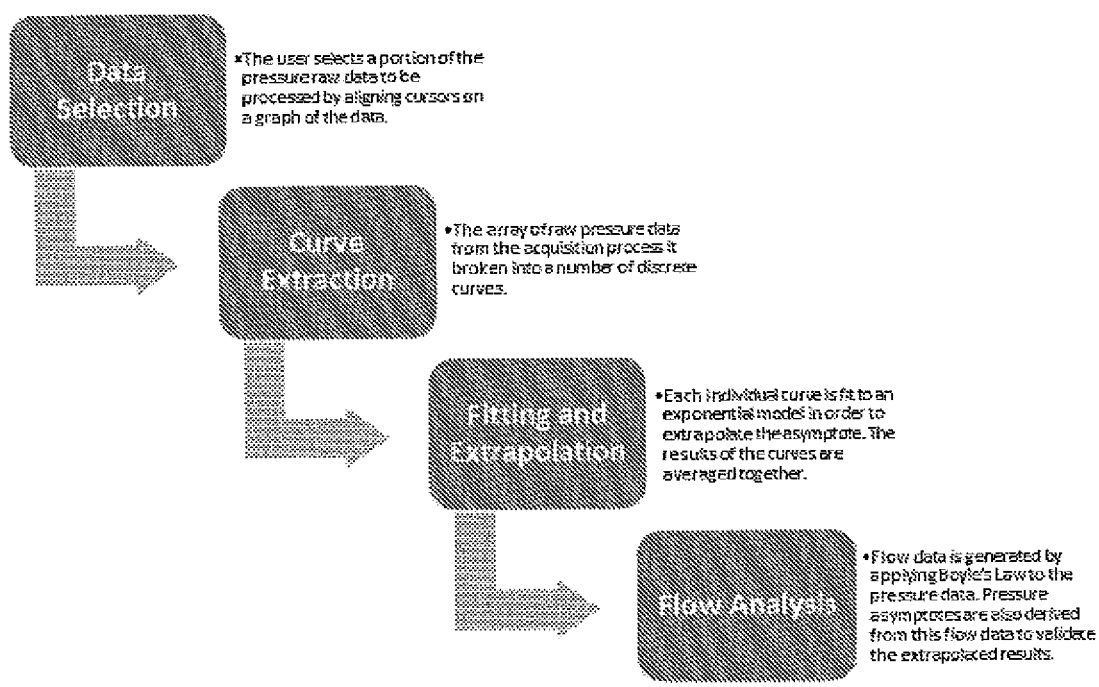

FIG. 41 depicts an exemplary pressure analysis process. In that exemplary figure, a user may (1) perform data selection; (2) curve extraction; (3) fitting and extrapolation, and (4) flow analysis. FIG. 42 depicts an exemplary system configuration panel interface, in which a user may set parameters for the acquisition and analysis processes. As depicted in FIG. 43, a user may set a number of acquisition parameters, including sampling rate, maximum pressure, solenoid valve open time, terminal configuration, timeout, tolerance, and minimum pressure parameters.

FIG. 44 depicts a variety of analysis parameters; some exemplary parameters include DAQ filter parameters, effective zero pressure, curve error tolerance, number of data points, atmospheric pressure, and initial air volume. It should be understood that this listing of parameters is illustrative only and is not restrictive or limiting. A user may use some, all, or even none of these parameters.

Figure 45:
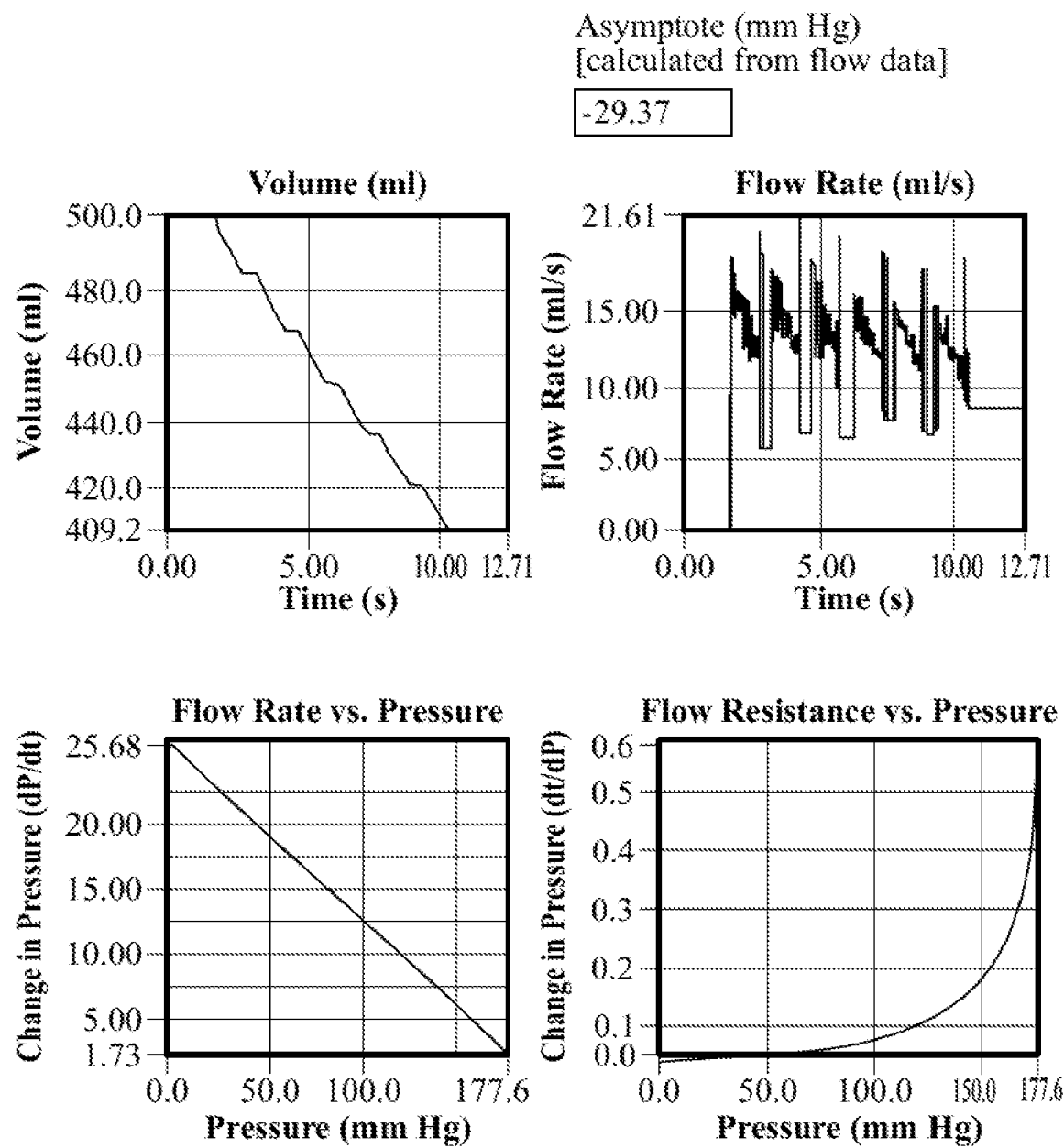

FIG. 45 shows a variety of exemplary curves obtained from an exemplary system according to the present disclosure. As shown, a user may crop raw data to be processed. After processing each pressure curve and averaging the results, the following is plotted: Extrapolated Curve, Flow Rate (dp/dt), Flow Resistance (dt/dp), Flow Rate vs. Pressure, and Flow Resistance vs. Pressure. By applying Boyle's Law to the pressure data, both Volume (ml) and Flow Rate (ml/s) are calculated and plotted to verify the extrapolated results.

Figure 50:
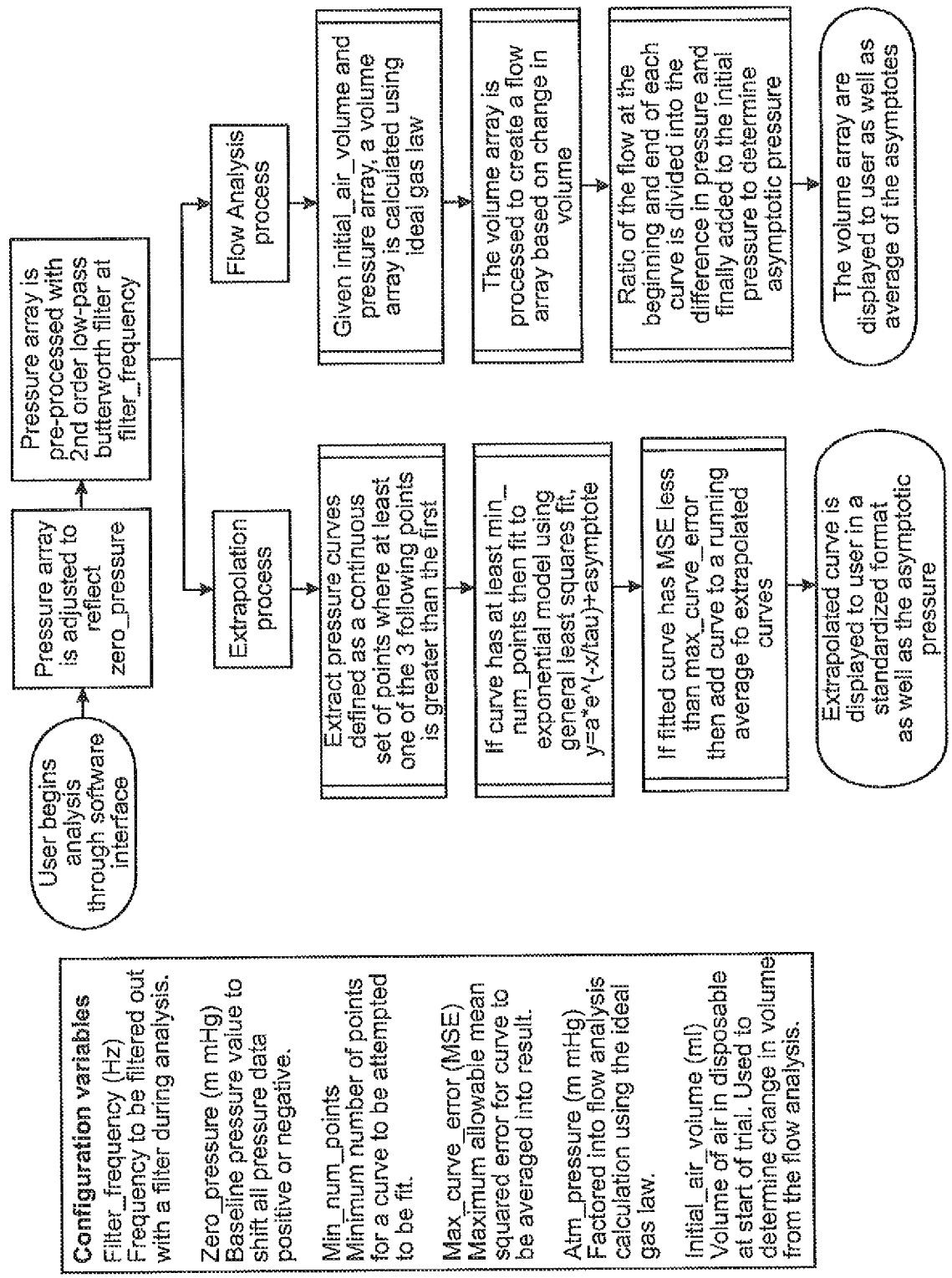
FIG. 50 provides an information flowchart for a system according to the present disclosure.

FIG. 50 provides an exemplary information flow for an exemplary system. As shown, a variety of variables (shown on the "Configuration Variables" panel of the figure) may be considered in the system. As shown, a pressure sensor or pressure array may be adjusted to reflect zero pressure, and a pressure array may be preprocessed with a low-pass filter. The system may engage in an extrapolation process, in which data points are analyzed and then fit to an exponential (or other) model, which may be accomplished using a least-squares analysis. The system may also perform flow analysis processes, as shown in the figure. Curves and values of interest (e.g., asymptotic bladder pressure) may be displayed to the user.

Figure 51:
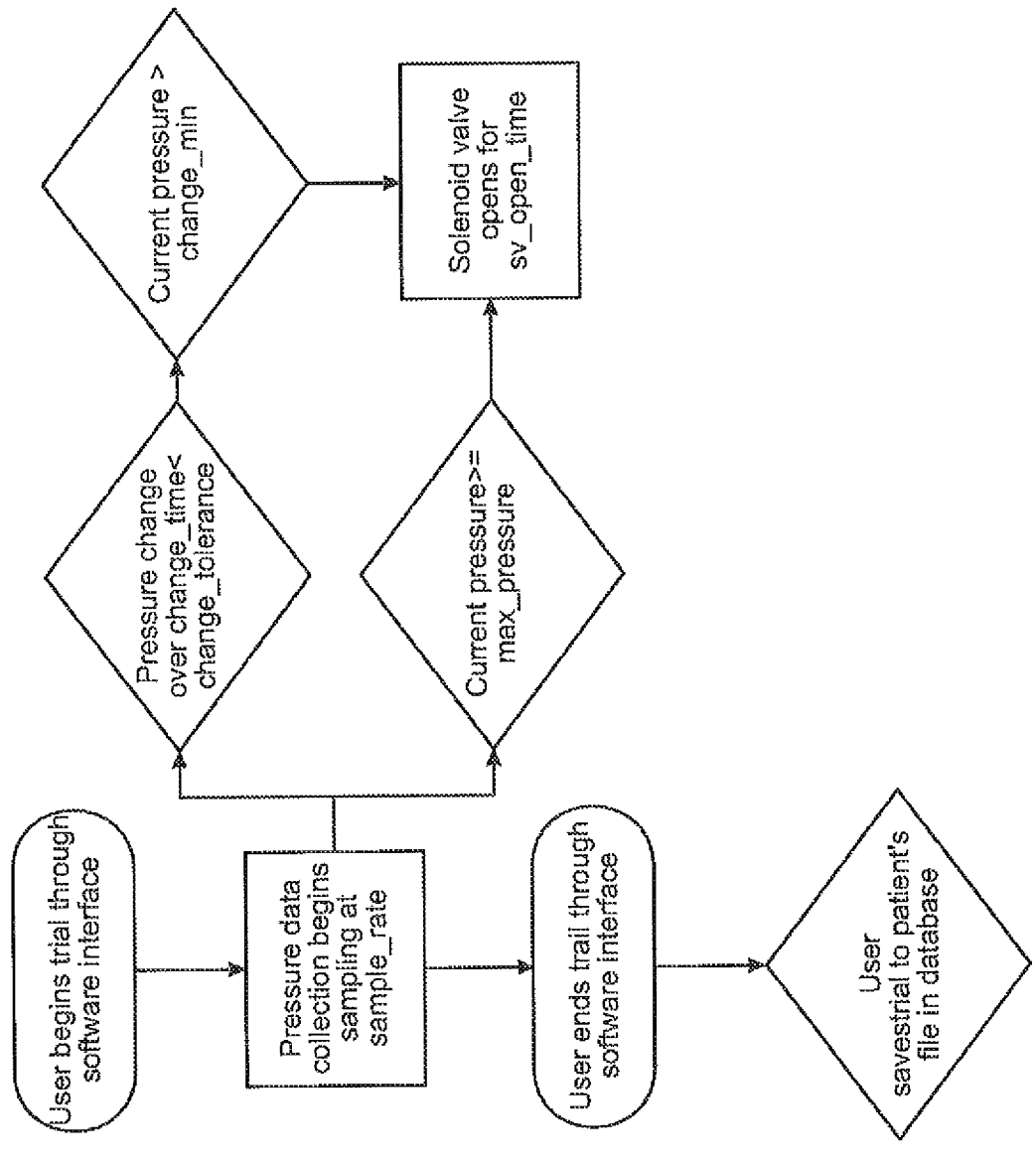
FIG. 51 provides a further information flowchart for a system according to the present disclosure.

FIG. 51 provides an exemplary DAQ (data acquisition) information flowchart. As shown in the "Configuration Variables" panel, a number of variables may be considered by the process. A user may begin sampling data, with the system collecting pressure data as a function of time and also managing the opening of a solenoid (or other) valve as needed to vent the interior of the urine receptacle. The trial data may be saved to a patient's file in a database.

Systems may, as described elsewhere herein, include a receptacle, a component configured to effect mechanical, leak-proof fluid communication between a subject's urethra and the receptacle so as to give rise to a flow circuit; the component comprising a vacuum chamber having an entry opening adapted to engage with a subject's anatomy proximate to the subject's urethra, the system being configured to, under application of sufficient vacuum to the vacuum chamber, effect fluid communication between the subject's urethra and the receptacle; and a sensor configured to measure a pressure within the receptacle.

Suitable components are described elsewhere herein; components according to the present disclosure are suitable for use in the disclosed systems. A component suitably includes a urethral engagement conduit having a proximal opening.

Systems are suitably configured to effect, under application of sufficient vacuum, passage of the anatomy proximate to the urethra into the vacuum chamber through a gap between the entry opening of the vacuum chamber and the proximal opening of urethral engagement conduit. The component suitably comprises the receptacle, although this is not a requirement, as the receptacle may reside in a device with which the component engages.

The system suitably includes a vacuum source, which vacuum source may be in fluid communication with the vacuum chamber. Suitable vacuum sources include pumps, squeeze bulbs, and the like.

A system also suitably includes a release device that is adapted to release urine, air, or both from the receptacle. The release device may be, e.g., a solenoid valve, a butterfly valve, a ball valve, and the like. The release device may engage with the component. For example, this may be by way of an aperture, tap, or other connection to the receptacle. As described elsewhere herein, the release device may be comprised in the component. A system also suitable includes a device configured to controllably actuate the release device. As one example, the system may include a servo, a magnet, solenoid coil, or other aspect that acts to actuate the release device. The system is suitably configured to controllably actuate the release device.

In some embodiments, the system includes a component (which may be disposable) that engages with a subject and then also engages with an analysis/control device. The component, as described elsewhere herein, may include a urethral engagement region, a urine receptacle, or both. In other embodiments, however, at least one of the urethral engagement region and receptacle are part of an analysis/control device. In these embodiments, the user may clean out (e.g., sterilize) the urethral engagement region and/or receptacle between patients. Alternatively, the system may comprise a disposable urethral engagement region, a disposable receptacle, or both.

Figure 55:
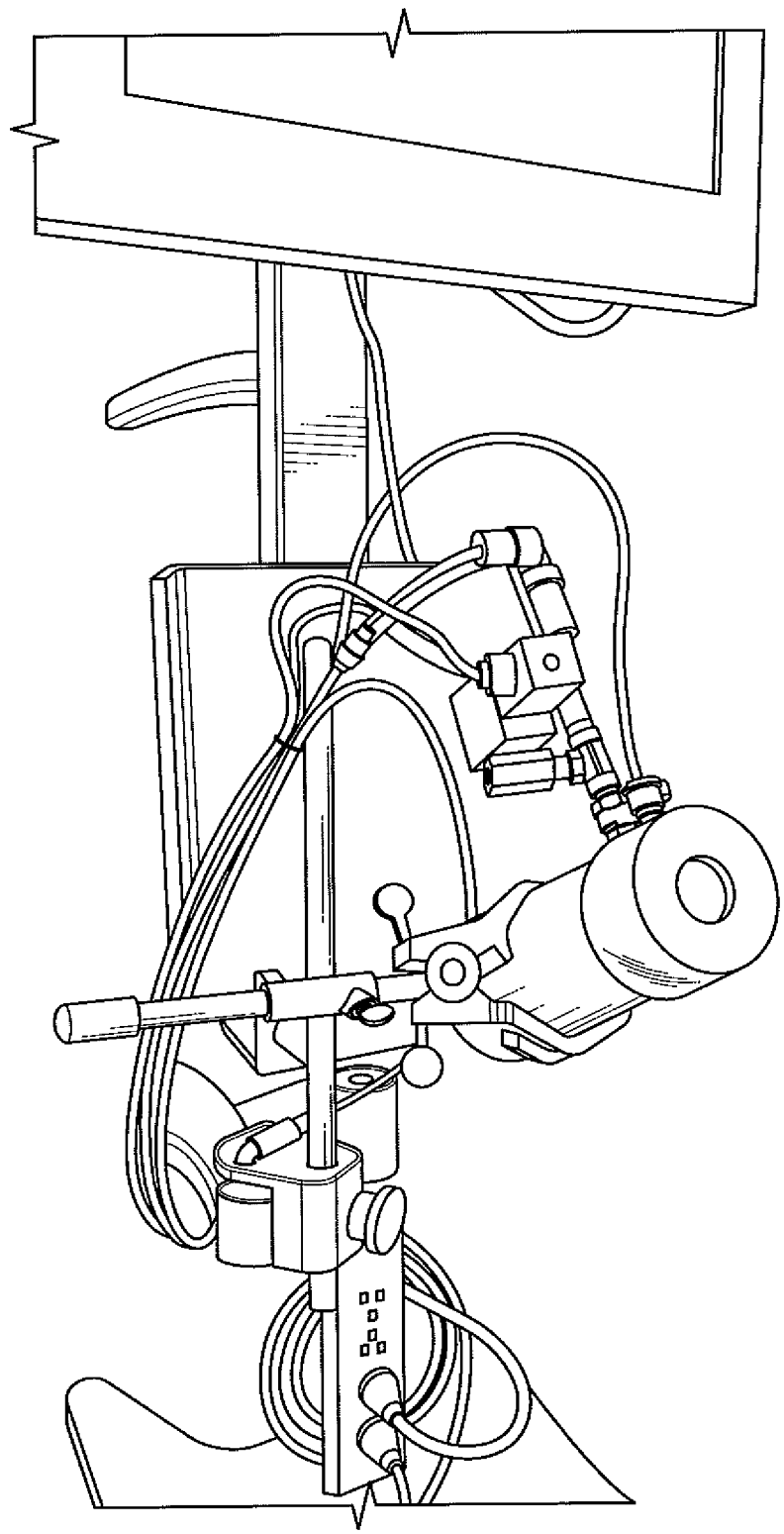
FIG. 55 illustrates a system and component according to the present disclosure.

An exemplary system is shown in FIG. 55. That figure shows a component having a vacuum chamber connected via a tube to a source of vacuum. The component also includes a receptacle (into which a subject may excrete urine). The receptacle includes a port that places the interior of the receptacle into fluid communication with the environment exterior to the receptacle. In this instance, the port is connected to a pressure sensor that may monitor the pressure within the receptacle. The port is also connected to a valve that may release pressure from the interior of the receptacle.

Figure 56:
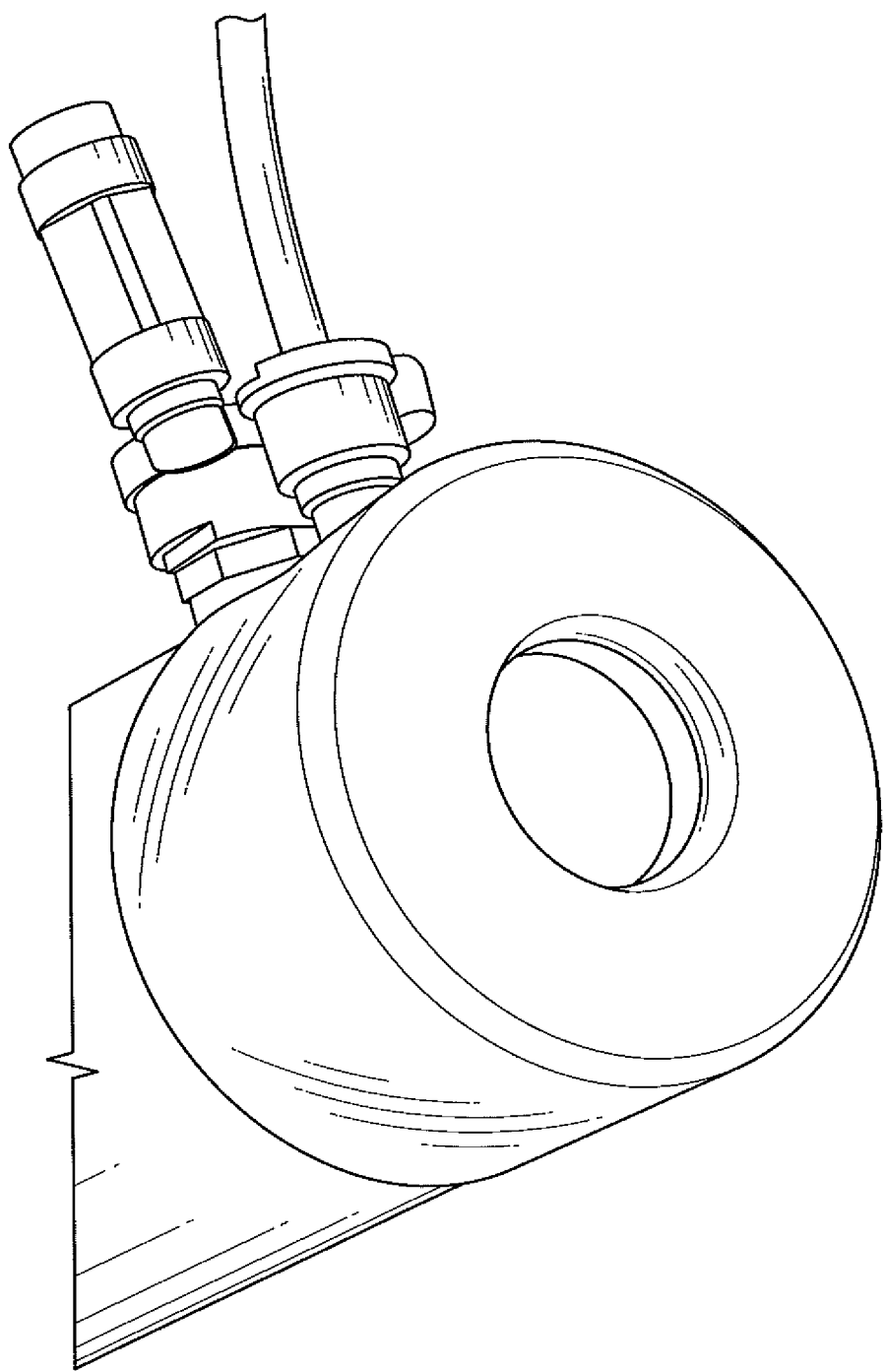
FIG. 56 illustrates a component according to the present disclosure, with a close-in view of the vacuum chamber and urethral engagement conduit.

FIG. 56 provides a close-in view of the component of the system in FIG. 55. The component in FIG. 56 includes a vacuum chamber and a port to the vacuum chamber; the port is connected to a tube that supplies a vacuum to the chamber. The component also includes —as described elsewhere herein—a receptacle. The receptacle includes a port that places the interior of the receptacle into fluid communication with the environment exterior to the receptacle. As shown, the port is connected to additional tubing, which tubing places the port into fluid communication with additional elements.

Figure 57:
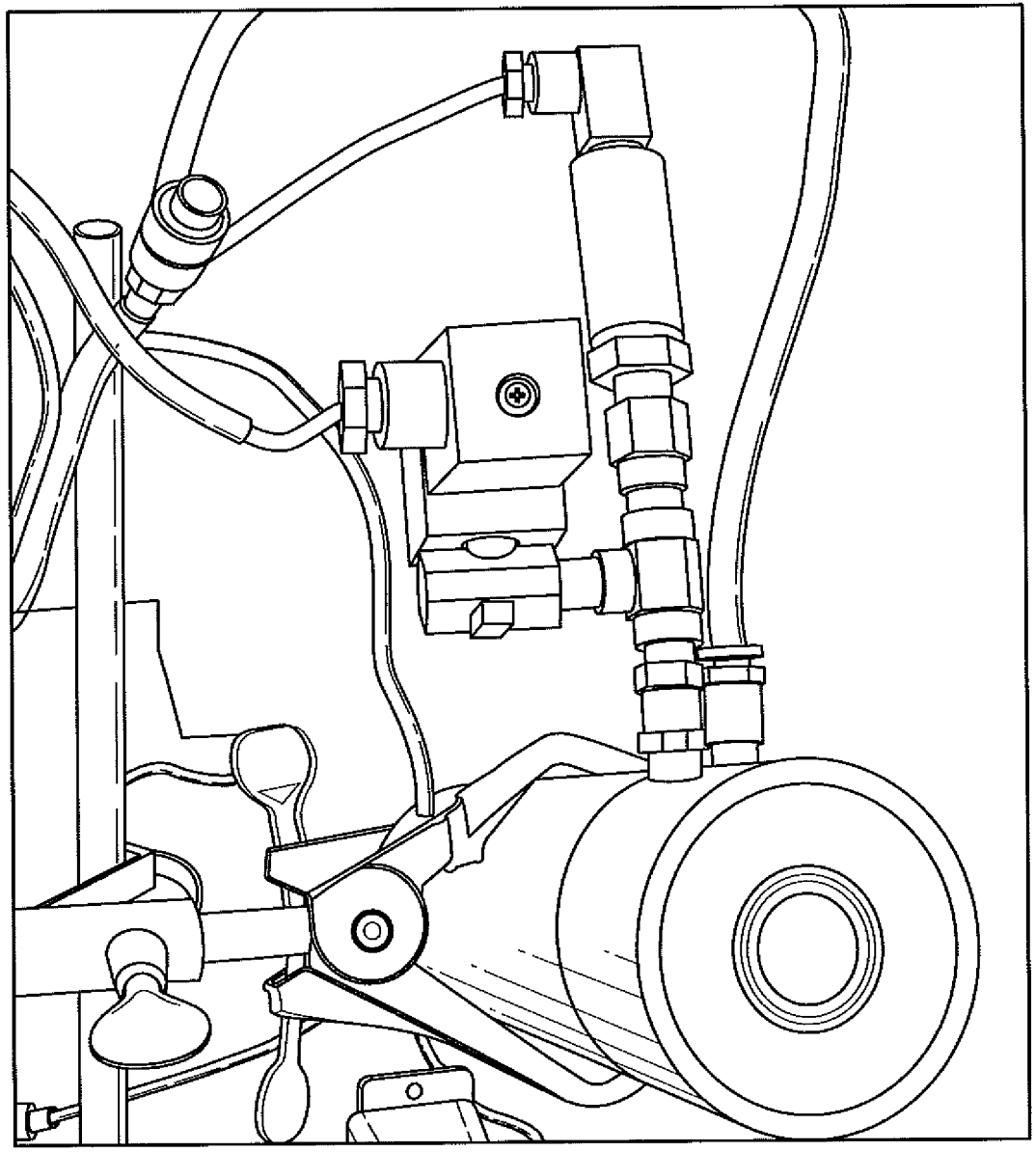
FIG. 57 provides an alternative illustration of the system of FIG. 55.

FIG. 57 presents the system of FIG. 55 in an alternative view. As shown in this figure, the port of the vacuum chamber is connected to a vacuum tube that supplies vacuum to the chamber. The receptacle port is connected to a pressure sensor and a release valve. The sensor provides receptacle pressure information to the system, and the system may be configured to control the release valve.

Systems may also include a device configured to measure or estimate a volume of urine excreted by a subject into the receptacle. Such a device may be a scale (that weighs urine excreted into the component). Alternatively, the system may be configured to measure the slope of a pressure vs. time curve, from which the system may calculate the flow rate of urine excreted into the receptacle.

The disclosed systems also suitably include a device configured to measure a pressure within the receptacle. Such a device may be a pressure sensor, a spring, a balloon, a column of fluid, and the like, any of which may be used to measure a pressure within the receptacle.

Figure 20:
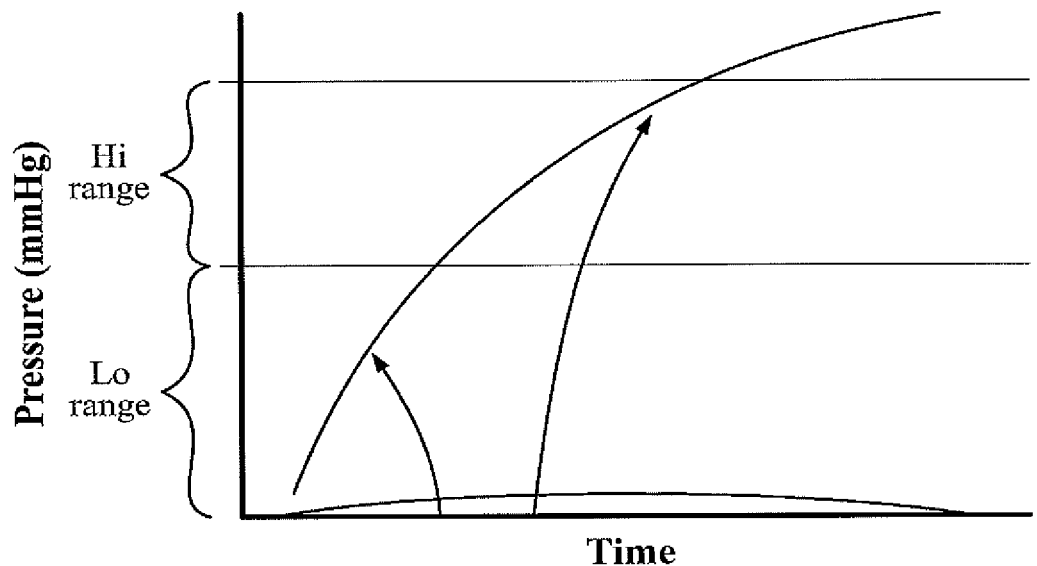
FIG. 20 depicts an exemplary, non-limiting model to estimate the asymptotic bladder pressure by curve fitting the low pressure segment of the pressure-time curve
Figure 21:
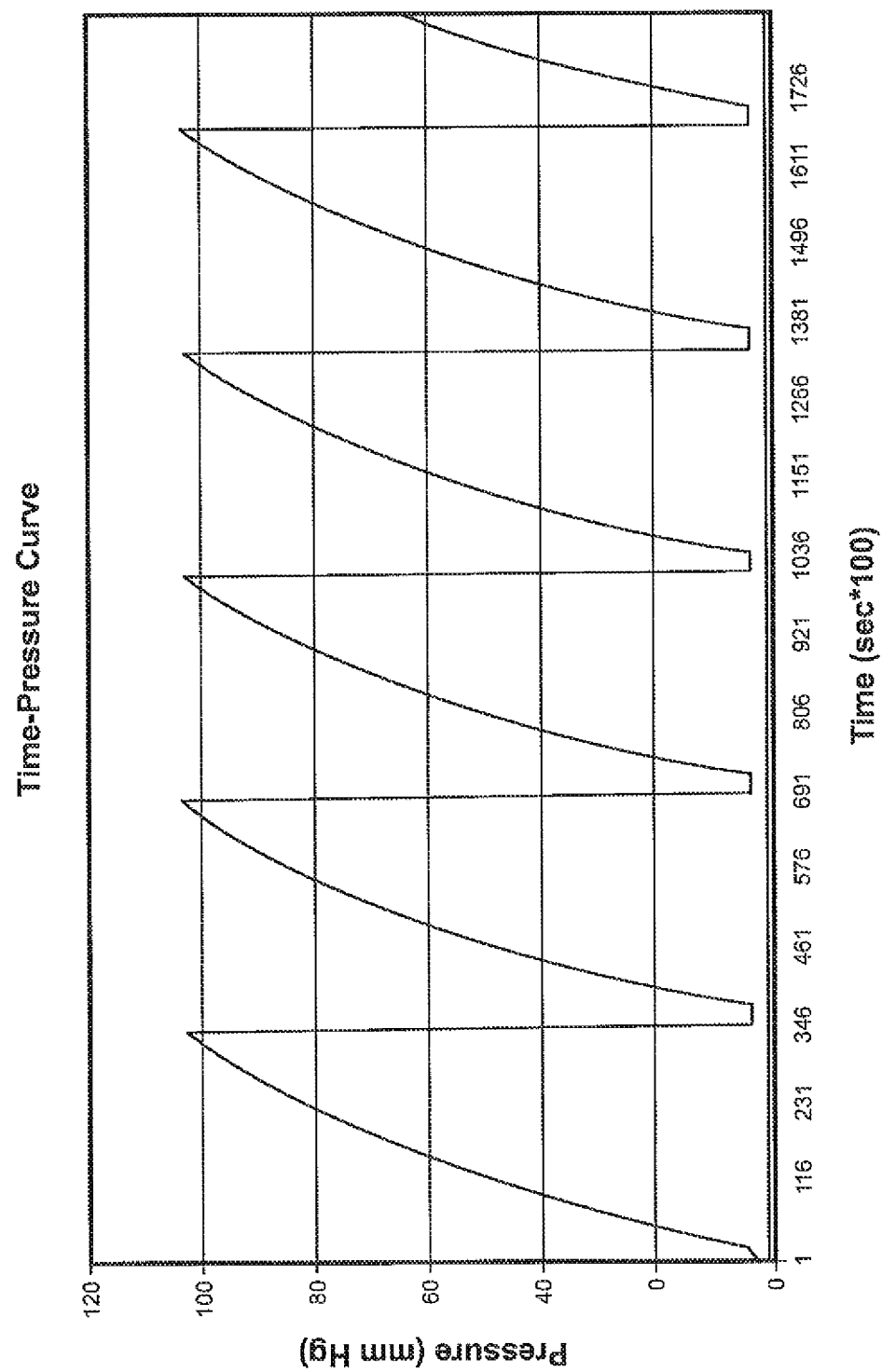
FIG. 21 presents an exemplary pressure vs. time curve; generated by hydraulic device (phantom patient) that emulates human LUT dysfunction

Systems may be configured to, for example, calculate a maximum pressure of a urine stream excreted into the receptacle, measure a maximum pressure of a urine stream excreted into the receptacle, or both. To measure a maximum (isovolumetric) bladder pressure, the system determines the pressure within the receptacle at the point that urine flow stops, at which point bladder pressure equals the back-pressure within the receptacle. Since measuring isovolumetric bladder pressure can be painful to the subject, it is advantageous to be able to calculate the maximum (asymptotic) pressure of the bladder from the lower pressure segment of the back-pressure curve To calculate a maximum pressure, a curve-fitting as shown in FIG. 20 may be applied. In one example, an asymptotic maximum pressure may be calculated by measuring the slope of the pressure vs. time curve when the pressure within the receptacle is 20 mm Hg and again when the pressure within the receptacle is 40 mm Hg, or else by continually measuring the slopes at each point on the selected portion of the time-pressure curve. By applying these slopes to arrive at an asymptotic curve fit, the user may then calculate the asymptotic maximum isovolumetric pressure that the subject's bladder can produce. Alternately, if the relationship between back-pressure within the closed air space and urine flow rate into the closed air space is linear, as in the current system, then the bladder isovolumetric pressure can be calculated by measuring the initial urine flow rate at zero back-pressure (atmospheric pressure), then measuring the back-pressure at 50% of the initial flow rate and multiplying that pressure by 2. Because the relationship between flow rate and pressure is linear, any convenient ratio can be used to extrapolate the isovolumetric bladder pressure. Put another way, because pressure vs. flow curve is linear, there is a simpler method of calculating the isovolumetric bladder pressure directly from the initial low pressure portion of the pressure-flow curve.

Curve fitting—e.g., to calculate the asymptotic isovolumetric bladder pressure—may be accomplished in a number of ways. One way to model the disclosed systems is to apply an electrical/physical model, i.e., charging a known capacitor (using urine to compress a known volume of air in a closed receptacle) with the combination of an unknown series resistor (unknown amount of urethral obstruction due to an enlarged prostate) using a battery of unknown voltage (urinary bladder of unknown strength of contraction). The solution is derived from analysis of the time-pressure curve of the back-pressure generated as the patient urinates into the closed air space under the assumption that the bladder isovolumetric (asymptotic) pressure (battery voltage) remains constant during much of micturition. Once the asymptote is calculated, all the other parameters can be calculated relative to the asymptote. The slope at any point reflects flow rate and the inverse slope represents resistance to flow (obstruction). The relative contribution of resistance to flow (obstruction due to prostate enlargement) and strength of contraction (bladder weakness) can be partialled out from these calculations. The test is non-invasive, painless and can be performed in less than one minute. A number of curve-fitting equations can describe the time-pressure curve; equations that describe the physical model are considered especially suitable.

Figure 22:
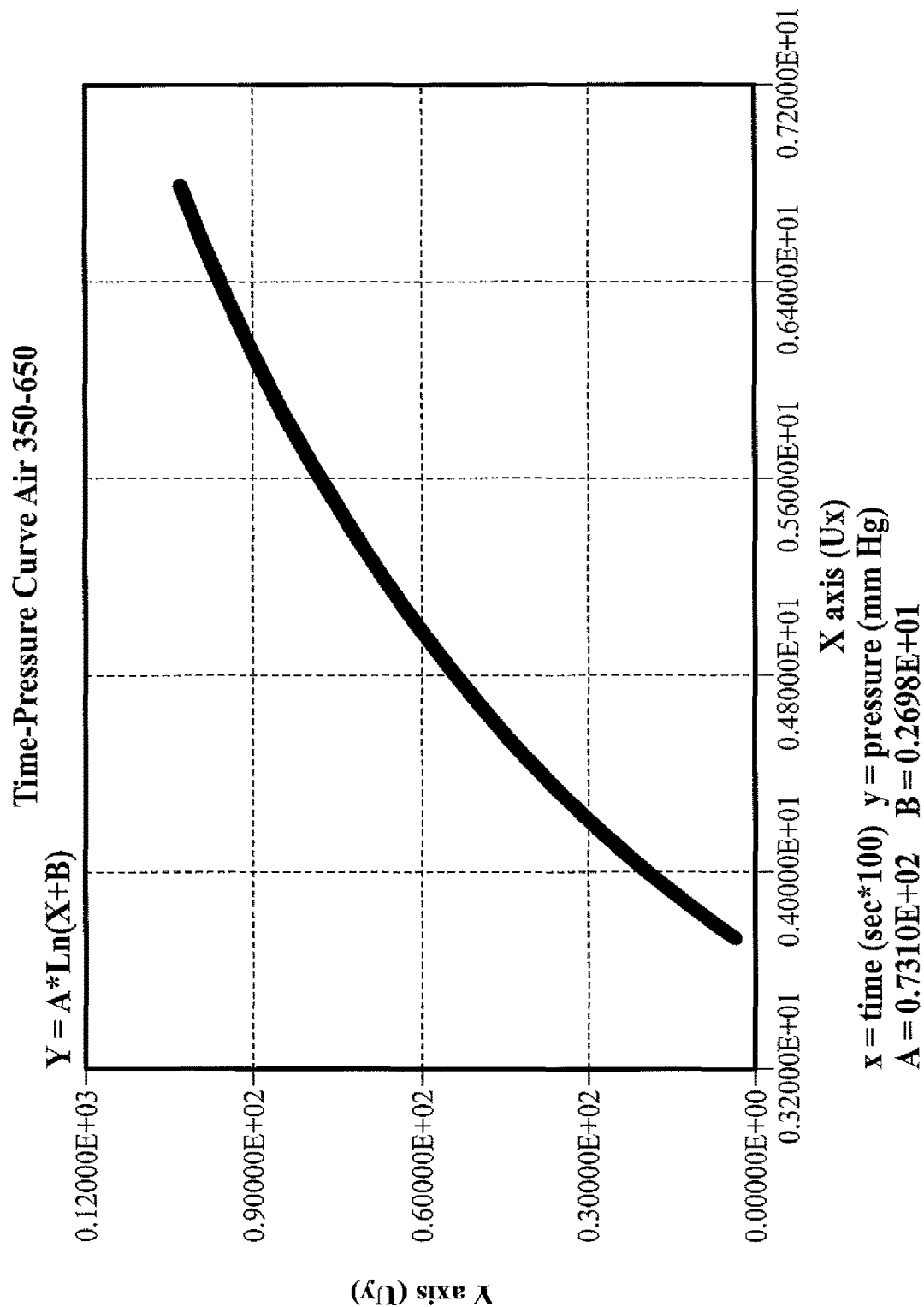
FIG. 22 presents a curve-fit used to estimate a maximum bladder pressure from an actual pressure vs. time curve; analysis of second pressure-time curve in FIG. 21
Figure 23:
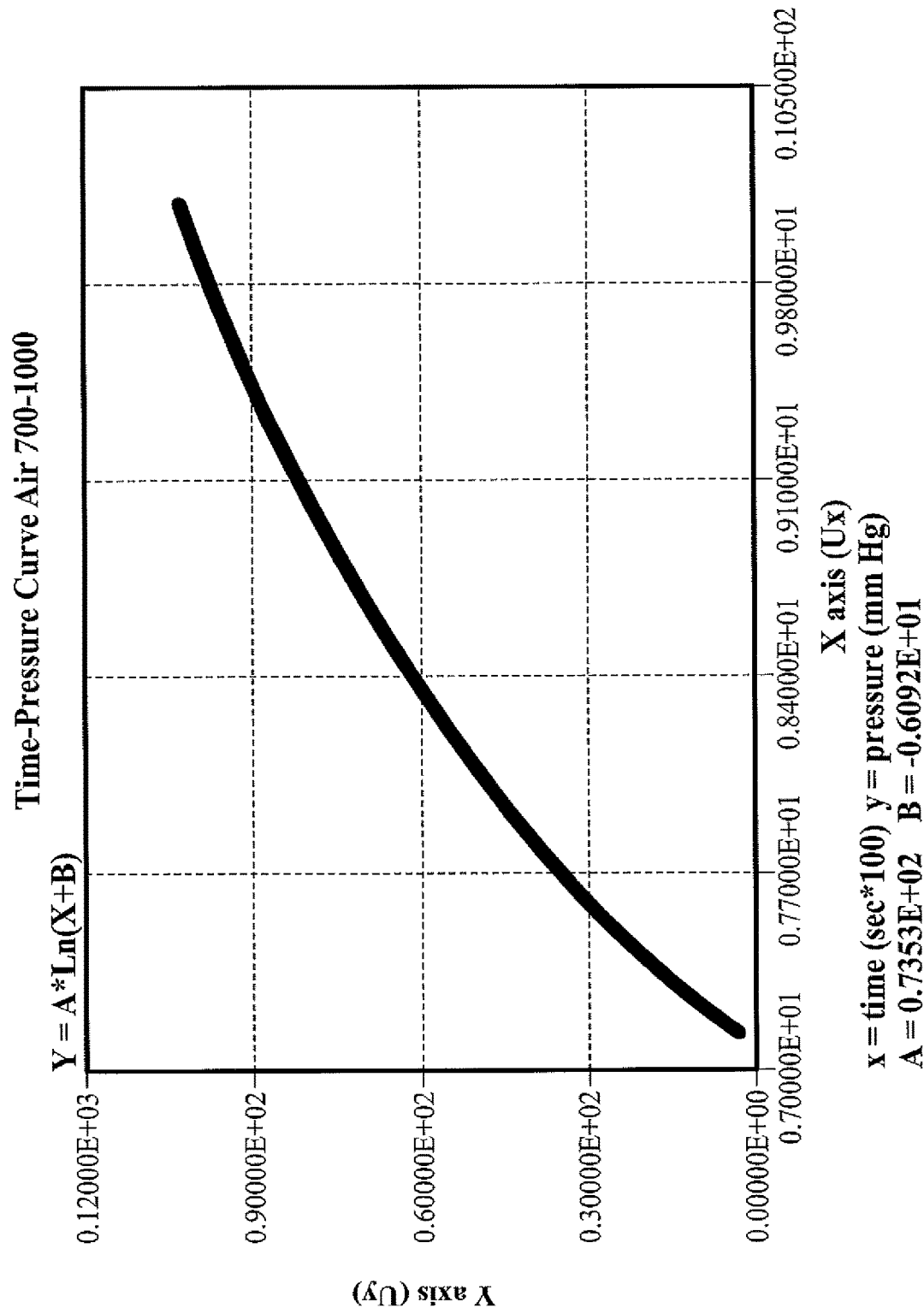
FIG. 23 presents another curve-fit used to estimate a maximum bladder pressure from an actual pressure vs. time curve; analysis of third curve in FIG. 21

One such approach applies the following model: $y=[a*\exp(-x/tau)]+c$. In this model (based on the differential equation used to describe the flow of electrons into a charging capacitor), a is the curve amplitude, x is time in seconds, tau is the time constant, and c is the asymptotic pressure. (Tau is the time needed for the curve to achieve ca. 63% of the maximum pressure.) In another model (e.g., FIG. 22 and FIG. 23), the following model is used: $Y=A*\ln(X+B)$, in which Y is pressure, X is time in seconds* 100, and A and B are coefficients particular to a given system.

Without being bound to any particular theory, because Boyle's law deals with absolute temperatures and pressures (atmospheric+gauge) the changes in atmospheric pressure may be considered in the disclosed technology. Atmospheric pressure may be measured and mathematically compensated in the calculations. As to temperature fluctuations, the potential effect can be mathematically compensated for by, e.g., using a thermistor inserted through the wall of the closed air space, or a RFID incorporated within the closed air space.

Because the airspace inside a device may be at a constant temperature, then the compression of the air by another fluid is an adiabatic process. Therefore, it is governed by the Boyle's Law, $P \times V = constant$, where pressure and volume are inversely related. Bladder pressure as a function of time, may be expressed in the following model:

$$pressure(time) = amplitude * e^{(time-tau)} + pressure_{asymptotic}$$

In one aspect, the disclosed technology may apply a multivariate linear regression model to fit low-pressure data to the generalized exponential model. This linear regression model may be expressed as follows $y = b_0 * x_0 + b_1 * x_1$. Using a General Least Squares (GLS) Fit function (GenLSFit from the National Instruments Advanced Analysis Toolkit) solved with the Singular Value Decomposition (SVD) algorithm, one may determine the two coefficients bo and bi, where bo is the amplitude and bi is the asymptotic bladder pressure. This function may produce a fit with the smallest Mean Squared Error (MSE). In the linear regression model, $x_0$ is $e^{(-time/tau)}$ and $x_1$ is a constant 1. Since tau, the time constant, is given for the linear regression model, an iterative least squares fit determines the value of tau (to a specified precision) by minimizing the MSE. After this process is complete, then the application has successfully best fit a pressure curve to the exponential model. Given raw input of multiple successive pressure curves, one may first filter discrete curves from the raw data. Each curve is fit independently, and then they are all averaged together. Flow rate and flow obstruction are derived from the extrapolated pressure data. Flow rate is determined by the change in pressure vs. time, which is exactly the derivative of the exponential model. Flow obstruction is determined by taking the inverse of the flow rate.

Again without being bound to any particular theory, another consideration in a pressure vs. time curve of micturition (urination) into a closed air space is due to LUT (lower urinary tract) compliance. LUT compliance may be measured by temporarily increasing a known volume of the closed air space (e.g., initially 100 ml of air) by another known volume (e.g., adding another 100 ml of air) during micturition. The result is several time-pressure curves at 100 ml and several at 200 ml of air. Deviation from the expected time-constant ratio (e.g., 2:1) reveals an amount of unknown LUT compliance. Solving the resulting capacitance charging equations (described elsewhere herein) may be used to derive a LUT compliance correction factor. Although not necessary, an accuracy (e.g., pressure) of +/−10% is useful for a parametric clinical measure. For example 100 mm Hg (range 90-110 mm Hg=normal bladder) versus 50 mm Hg (range 45-55 mm Hg=weak bladder) is clinically informative. For practical purposes there is no difference between 90 and 110 mm Hg isovolumetric bladder pressure. The measure of LUT compliance may also have clinical significance. The air venting UED can directly generate a measure of LUT compliance because it serially decreases the compliance of the closed air space with each iteration of the pressure-time curve as urine collects in the space and displaces air from the receptacle.

As to the amount of the time-pressure curve to use to extrapolate asymptotic pressure (isovolumetric bladder pressure) and flow resistance (bladder outlet obstruction), volunteers can often tolerate 80-100 mm Hg. There is no discomfort until back-pressure exceeds 60 mm Hg. A variety of methods, e.g., Lab Fit™, can perform non-linear regression for curve fitting the time-pressure curves. Even with all the sources of error-variance (atm. pressure, temperature, LUT compliance, etc.) a number of 2 parameter exponential equations were highly predictive ($r2>0.999$). For example, a suitable fit was made by $Y=A*Ln(X+B)$. A user may filter or edit out the high frequency artifacts (caused by "water hammer" when valve or solenoid opens and closes) especially at the very beginning of each time-pressure curve. Other curve-fitting models are also suitable, as $Y=A*Ln(X+B)$ is not the exclusive way in which to perform curve fitting.

As described elsewhere herein, an electrical model is useful, i.e., the time-voltage curve (time-pressure) or time-current (time-flow) curve of charging a capacitor of known capacitance (representing a closed air space of given volume) through an unknown resistor (representing Bladder Outlet Obstruction due to enlarged prostate) from an unknown DC voltage source (representing isovolumetric bladder pressure) with an unknown capacitor (representing LUT compliance) in parallel. The asymptotic voltage can be extrapolated and the resistance calculated by solving the specific exponential equation that describes the time-voltage curve. Without being bound on any particular theory, the expected behavior of the hydraulic system emulates the above electrical model, and curve fitting supports this hypothesis.

Figure 14:
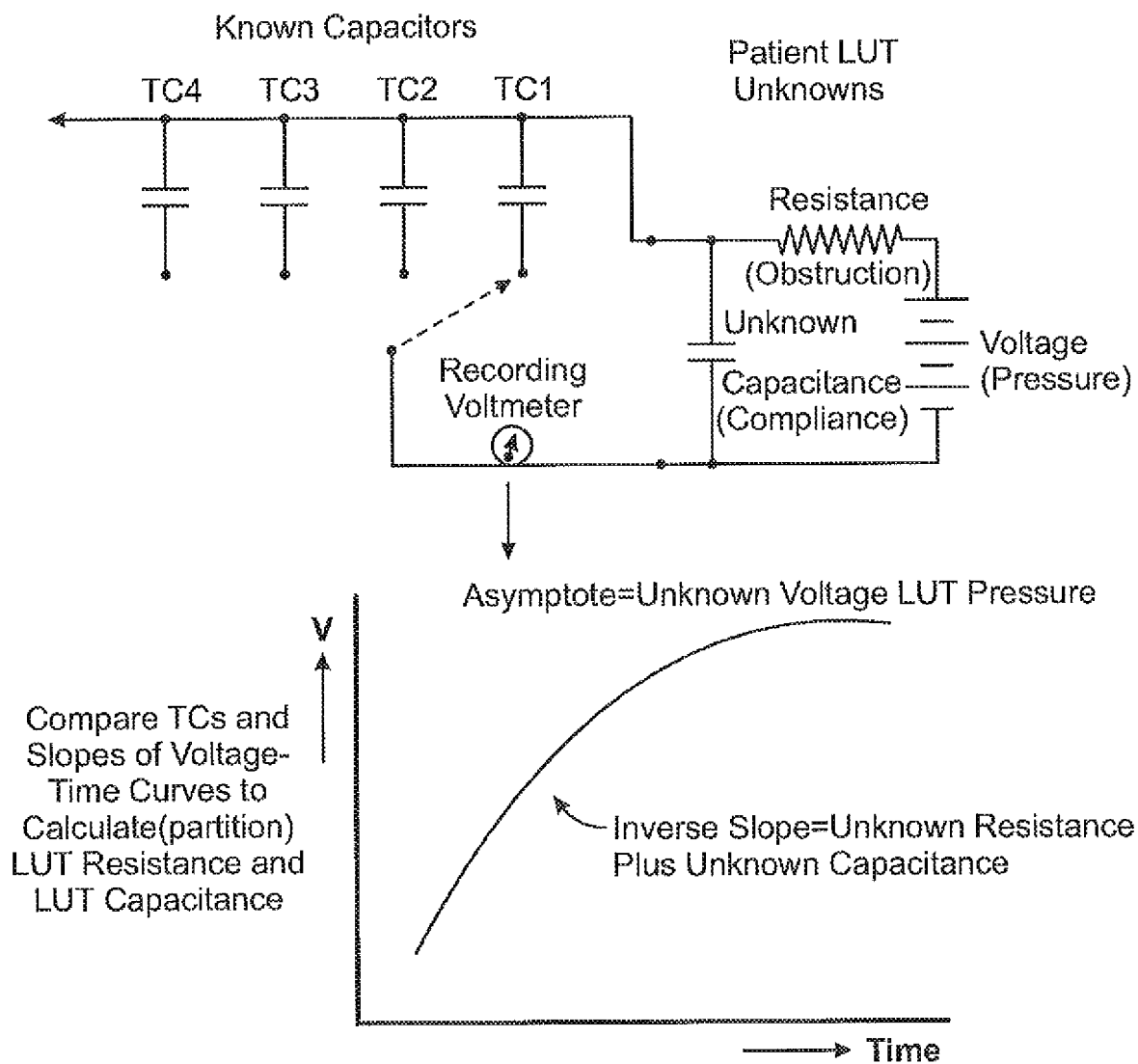
FIG. 14 depicts a capacitance-based model of the lower urinary tract (LUT), which is one method to measure compliance of LUT.

An exemplary model of a system according to the present disclosure is shown in FIG. 14. That figure presents a system analogized to an electrical capacitance model, which analogy may be used to calculate asymptotic values and other quantities.

More specifically, the pressure in a urine receptacle (i.e., pressure effected by excretion of urine into the receptacle) may be analogized to the voltage applied to a capacitance circuit. The voltage (pressure) is connected to some resistance, which may be considered an obstruction or other resistance to urine flow. A known capacitor (or capacitors) may also be connected to the voltage/pressure. Unknowns in the system include the maximum voltage (bladder pressure) as well as an unknown capacitance (compliance/resistance of the LUT). By gathering pressure vs. time data at known compliances, the user can measure a compliance/resistance of the system by calculating the slope of the pressure vs. time curve, and can also estimate the asymptotic maximum pressure exerted by the bladder.

Figure 18:
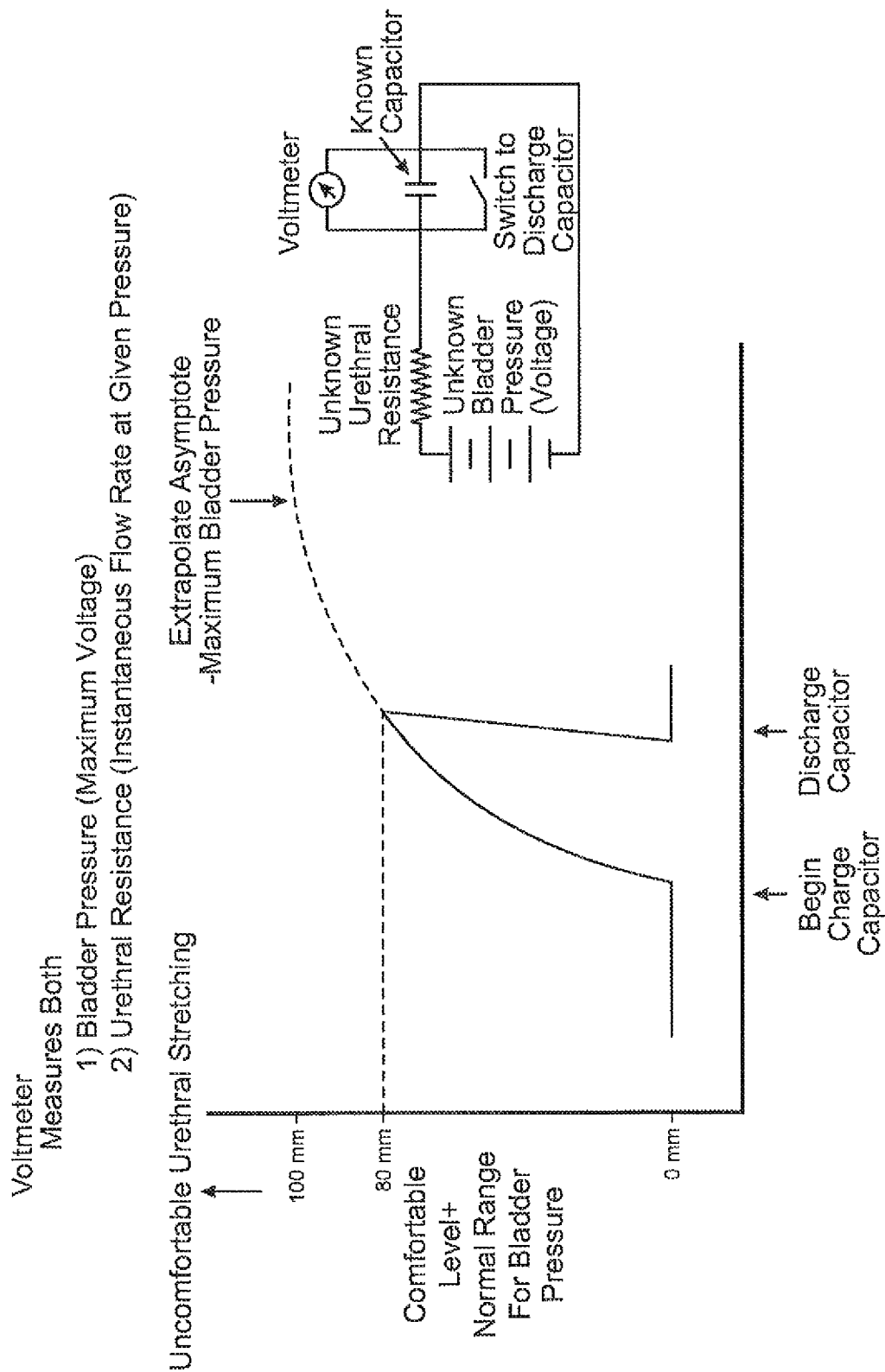
FIG. 18 depicts a capacitance-based model of the urethrocystometer; one may use initial portion of pressure-time curve to extrapolate isovolumetric bladder pressure and to measure instantaneous urine flow rates and resistance to flow—by extrapolating isovolumetric bladder pressure from the lower pressure segment of the pressure-time curve one may avoid discomfort associated with high back-pressure.

This is further shown in FIGS. 17 and 18, which figures presents the voltage-pressure analogy, within which presents the bladder pressure (voltage) and urethral resistance (resistance) as unknowns that are calculated by curve-fitting pressure vs. time data.

A system may also be configured to calculate a volume of urine excreted into the receptacle, to measure a volume of urine excreted into the receptacle, or both. Calculation may be effected by calculating a slope of a pressure vs. time curve, which slope in turn yields a flow rate, which can then be used to calculate a volume of urine. Measurement of the volume may be effected by visually measuring the amount of urine excreted into the receptacle, by weighing the urine excreted into the receptacle (e.g., by weighing the receptacle before and after urination) and converting that weight difference into a volume. The slope of the pressure vs. time curve at any point on the curve serves as a measure of the instantaneous flow rate under the specific conditions of bladder pressure and urethral resistance to flow. The inverse slope of the pressure vs. time curve serves as an instantaneous measure of urethral resistance under various pressure and flow conditions, and the asymptotic bladder pressure (at zero flow) provides a measure of bladder function (strength, weakness). The system may be used to calculate or measure volumetric flow in other living and non-living hydraulic and mechanical systems (as for example, hydraulic models of the human LUT - "Phantom Patients").

Systems may also calculate a compliance of the lower urinary tract, to measure a compliance of the lower urinary tract, or both. Compliance may be expressed, e.g., in terms of a slope of a pressure vs. time curve that presents pressure within the receptacle as a function of time. A system may also be configured to calculate a maximum pressure of a urine stream excreted into the receptacle based on a measurement of one or more pressures within the receptacle, as described elsewhere herein. The system may be used to calculate or measure compliance in other living or non-living hydraulic or mechanical systems.

A system may also include, e.g., a device configured to record receptacle pressure as a function of time, a device configured to display receptacle pressure as a function of time, or both. Such devices may be memory components (e.g., flash memory), LED screens, liquid crystal screens, and the like.

The flow circuit of the system may—as described elsewhere—include a flow resistance device. The flow resistance device may have a variable flow resistance. Receptacles may include a heat-absorbing material, as described elsewhere herein.

A system may also be configured to measure urine pressure within the receptacle, urine stream flow rate, or both, at intervals greater or less than about 1 second, or even less than about 0.5 seconds, less than about 0.2 seconds, and even less than about 0.1 seconds.

Systems may be configured to release urine, air, or both from the receptacle in response to a pressure within the receptacle of less than about 200 mm Hg, or even less than about 50 mm Hg. This may be done, for example, to prevent the subject from experiencing discomfort from a pressure at their distal urethra. In such a case, the system may release air, urine, or both at a receptacle pressure of, e.g., 80 mm Hg or less. As explained elsewhere herein, the system—or a user—can calculate a maximum asymptotic receptacle pressure from data obtained at receptacle pressures of less than that maximum asymptotic pressure. As explained elsewhere herein, however, the system may measure an actual maximum pressure, i.e., the maximum asymptotic pressure obtained when the subject excretes (isovolumetrically) into the component and receptacle. The system may also be used to release other liquids or gases from living and non-living hydraulic and mechanical systems.

Systems may also be configured to apply a correction for diabatic effects, temperature effects, atmospheric effects, or any combination thereof on the receptacle. As shown in FIGS. 11, 12, 13, and 15, the pressure within a receptacle may experience a temporary spike in pressure followed by a diabatic decay. This may be accounted for by the system. The system may also be used to correct diabatic effects, temperature effects, atmospheric effects or any combination thereof in other living and non-living hydraulic and mechanical systems involving compressing and decompressing gasses.

In some embodiments, a device may self-calibrate. As one example, a standard urological method (such as a uroflowmeter) may be incorporated into a system NUD to automatically correct measurement errors (such as diabatic processes) introduced by the air-based pressure measuring system. A built-in uroflowmeter (capacitance, load cell, rotational, etc.) can be added to a system.

There are various methods of analyzing and correcting the back-pressure data for diabatic and other sources of error, although it is not necessary to account for or even compensate for them, First, the instantaneous slope at any point in time on the uroflowmeter volumetric flow curve (representing the actual instantaneous flow rate) provides a point-by-point correction for the instantaneous slope of the back-pressure curve (which represents the erroneous instantaneous flow rate) at that same point in time, if both are simultaneously recorded at X (e.g., 100) data points per second. The point-by-point correction provides the actual urine flow rate (corrected slope) at that given back-pressure (under the specified conditions of urine flow rate, resistance to flow and bladder isovolumetric pressure). This corrected instantaneous flow rate data also permits calculation of the corrected instantaneous resistance to flow (corrected inverse slope) and the pressure asymptote (isovolumetric bladder pressure) to be accurately calculated.

One may also extract the foregoing information directly from the uroflowmeter volumetric flow curve by plotting the instantaneous uroflow data point-by-point against the simultaneous back-pressure data. The resulting curve is the corrected flow vs. pressure data. Curve fitting the corrected flow-pressure data generates the corrected instantaneous resistance to flow and the pressure asymptote.

In some embodiments, a test involves only the low pressure segment (e.g., 0 to 60 mm Hg) of the complete (e.g., 0 to 120 mm Hg) back-pressure curve, so flow is maximum at the beginning and decreases as back-pressure builds up till the vent opens at the selected low pressure (e.g., 60 mm Hg) to dump air (or urine) from the closed air chamber, and the back-pressure curve (e.g., 0 to 60 mm Hg) is repeated over and over till the test ends. An independent measure of instantaneous urine flow rate recorded concurrent with the back-pressure curve permits each slope point on the back-pressure curve to be corrected for the actual instantaneous urine flow, also correcting the instantaneous flow resistance (amount of obstruction) and the curve asymptote (isovolumetric bladder pressure).

Alternatively, the actual total volume of urine collected during the study would be measured. This volume of urine reflects the total area subsumed by all the time-pressure curves generated during the study, minus the subsumed area attributable to diabatic pressure and other errors. The actual flow rate is calculated at the beginning and end of each time-pressure curve (of the multiple time-pressure curves during a study) and each time-pressure curve is curve-fitted to create a descriptive equation. In the case of urine-venting, the time-pressure curves would be essentially the same, as the volume of the closed air chamber would remain the same between each time-pressure curve. In this case the time-pressure curve equations are averages to increase precision of extrapolation of the complete time-pressure curve from the initial low pressure segment. In the case of air venting there would be compliance changes in the closed air chamber between each time-pressure curve (as accumulating urine displaces the air), so each curve would have a distinct equation in which one parameter would be a measure of urethral compliance.

Also, as described elsewhere herein, a heat-absorbing material (also termed "heat sink") may be used to reduce or even eliminate these diabatic effects. The heat sink may be used to increase the heat capacity of the component (or receptacle) by at least about 0.1%, 1.0%, 5%, 10%, 50%, 100%, 200%, 500%, 1000%, 5000%, 10000%, or by even more. In this way, the heat sink absorbs heat energy generated by compression of air within the closed air space that might otherwise raise the temperature within the receptacle resulting in pressure measurement error. The heat sink may serve to moderate or even eliminate diabatic and/or other temperature effects due to compression and de-compression of a gas.

Figure 24:
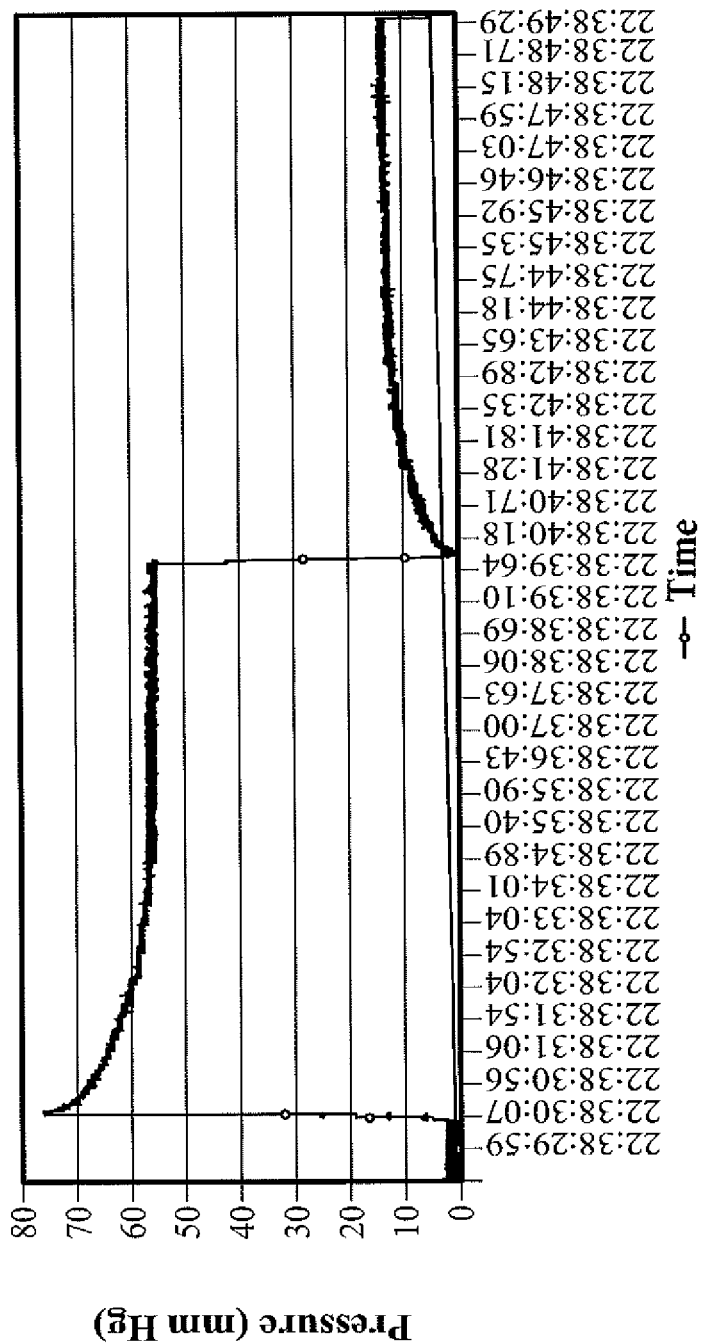
FIG. 24 presents pressure vs. time data for an exemplary receptacle that does not include a heat sink; using test device exemplified in FIG. 12; note the presence of diabatic error
Figure 25:
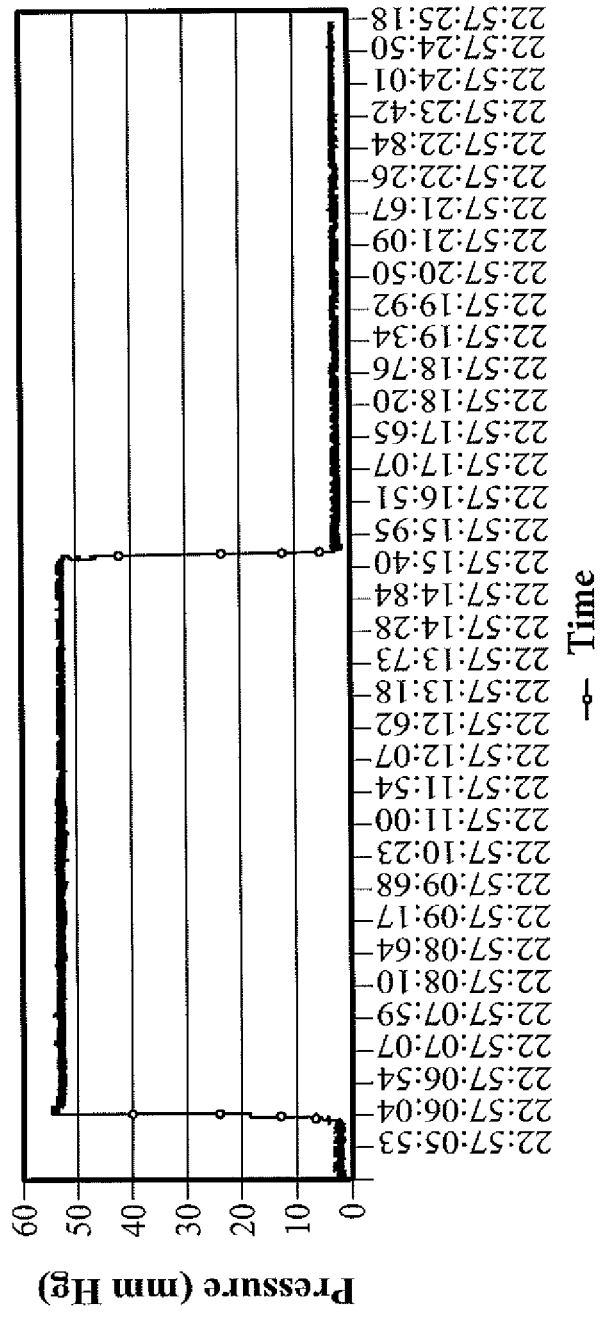
FIG. 25 presents pressure vs. time data for an exemplary receptacle that includes steel wool as a heat sink; using test device exemplified in FIG. 12; note absence of diabatic error

The effect of a heat sink is shown by exemplary FIG. 24 and FIG. 25. FIG. 24 illustrates that for an exemplary receptacle that does not include a heat sink, diabatic effects contributed to sizeable (20%+) transient changes in pressure at compression and release. FIG. 25 illustrates that when a heat sink (steel wool, bronze wool or glass wool) was present in the receptacle, these effects were greatly reduced or eliminated.

Figure 11:
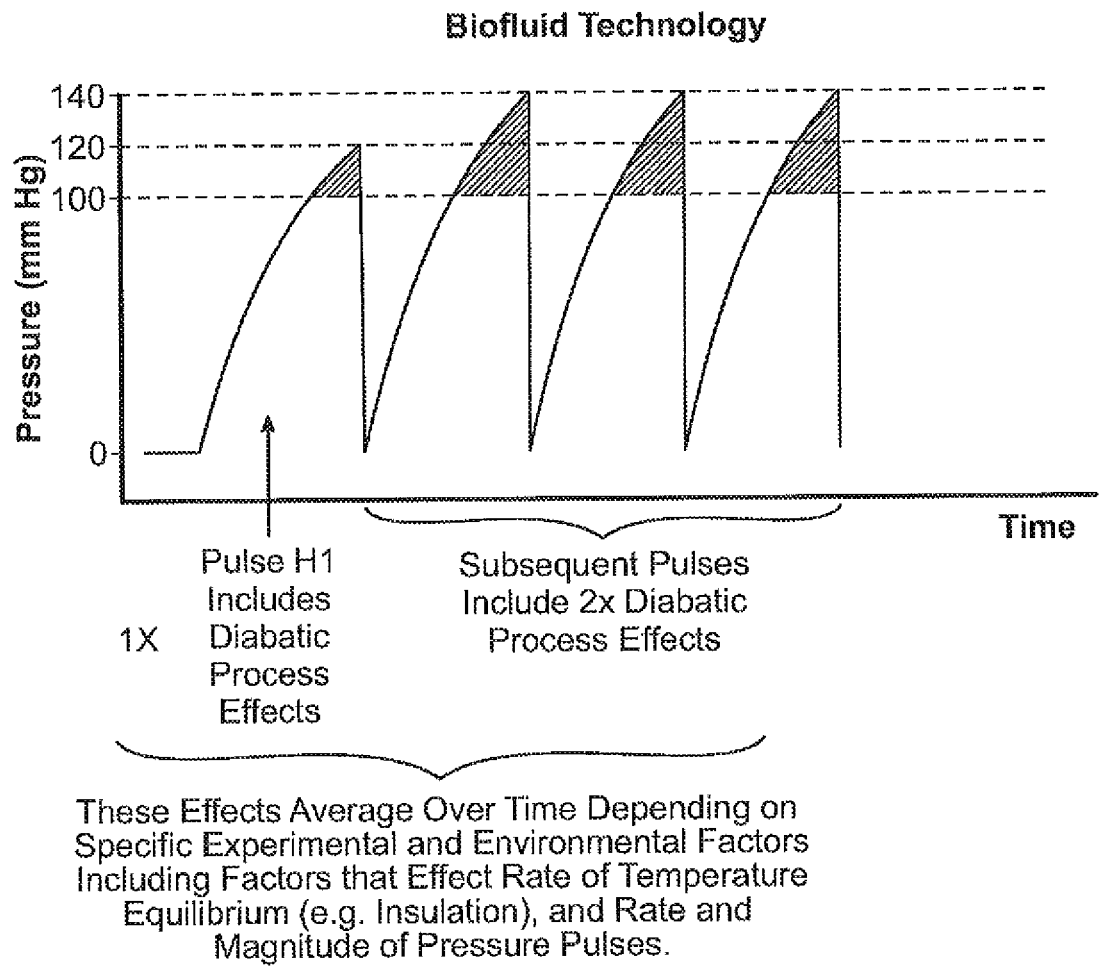
FIG. 11 depicts data from an exemplary pressure vs. time experiment.
Figure 12:
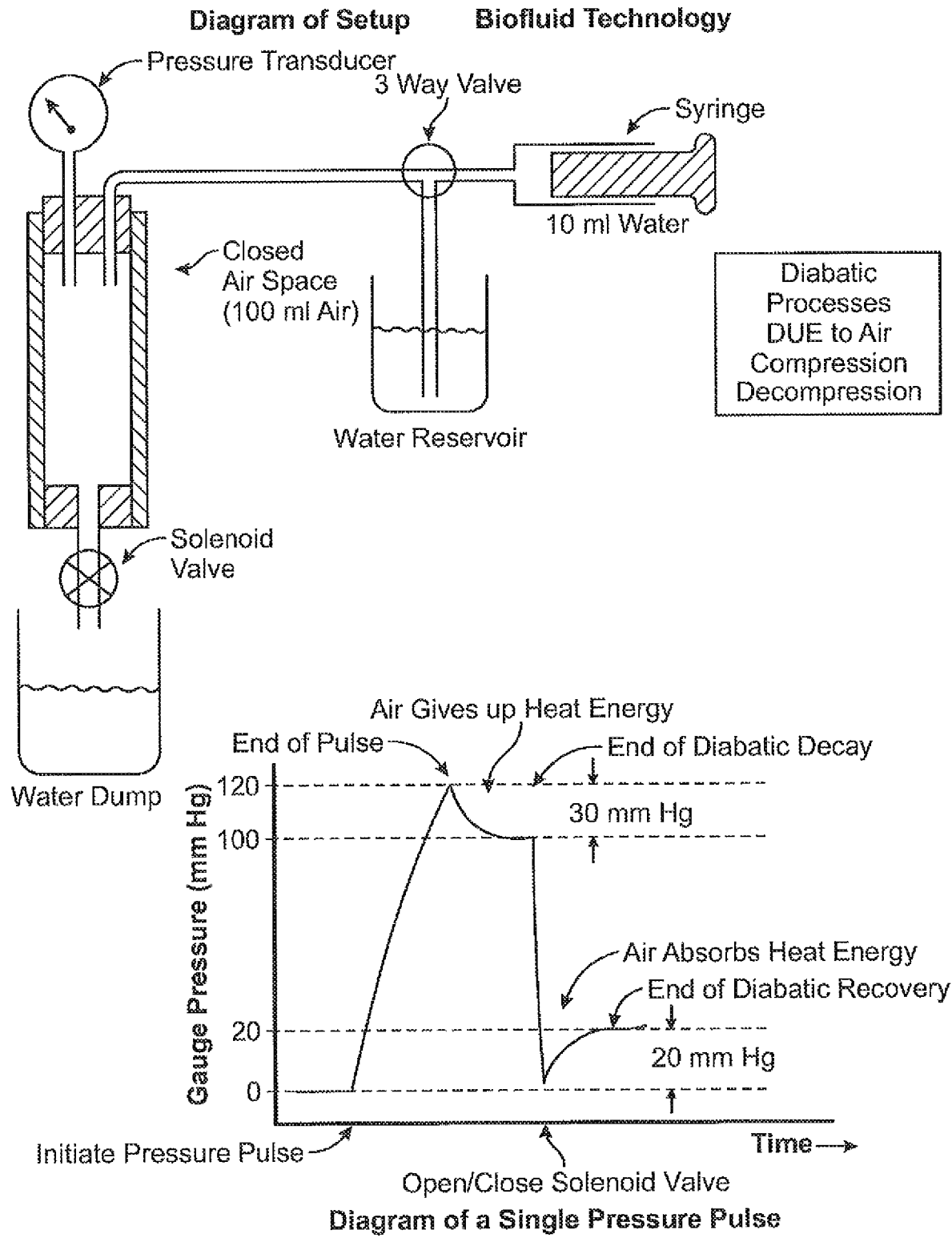
FIG. 12 depicts an alternative system for gathering pressure vs. time information, which may be relevant to methods to measure magnitude of error due to diabatic processes.
Figure 19:
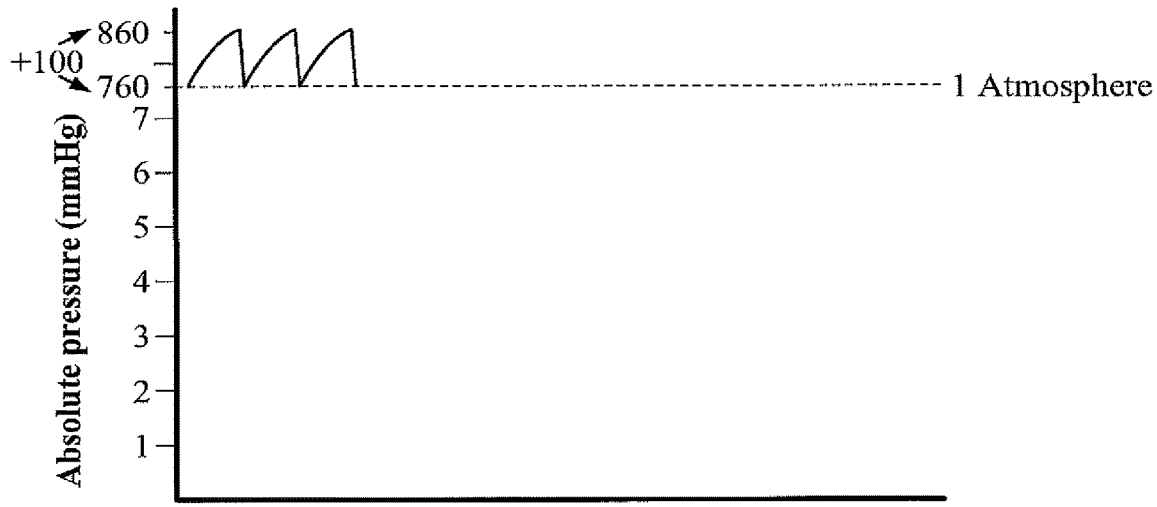
FIG. 19 depicts an exemplary calculation of urinary flow with correction for differences in atmospheric pressure.

As shown in FIG. 11, pressure vs. time curves may be influenced by diabatic effects (from the compression and de-compression of the contents of the receptacle during operation), temperature effects, atmospheric pressure effects, and the temperature of the urine excreted into the chamber; data from air-based pressure measuring system may include errors that can be controlled, compensated and corrected. FIG. 19 presents an exemplary calculation showing, using Boyle's law, a calculation of the volume of urine that must be excreted into a chamber of 100 ml volume and also a chamber of 200 ml volume to raise the pressure within the chamber 100 mm Hg above atmospheric pressure, for example, from 760 mm Hg to 860 mm Hg absolute pressure. Barometric pressure is measured and these effects accounted for and incorporated into analysis of the pressure vs. time curves. A barometer may be used to correct pressure-time curves for variations in atmospheric pressure FIG. 12 presents an exemplary embodiment of a system according to the present disclosure. A syringe, pump, or other device may be connected to a 3-way valve that connects the syringe to a water reservoir (to simulate urine) and a receptacle. A pressure sensor is configured to measure the pressure within the receptacle, and a valve (e.g., a solenoid) is configured to release the contents of the receptacle. As shown in the exemplary pressure vs. time curves at the bottom of FIG. 12, diabatic effects can result in a temporary change in temperature (and hence) pressure upon urine entry into a closed receptacle as well as another temporary change in pressure upon urine (or air) release. These effects can be accounted for by incorporating them into a curve-fitting algorithm or by adding or subtracting some amount from a collected pressure value in a pressure vs. time curve.

Figure 13:
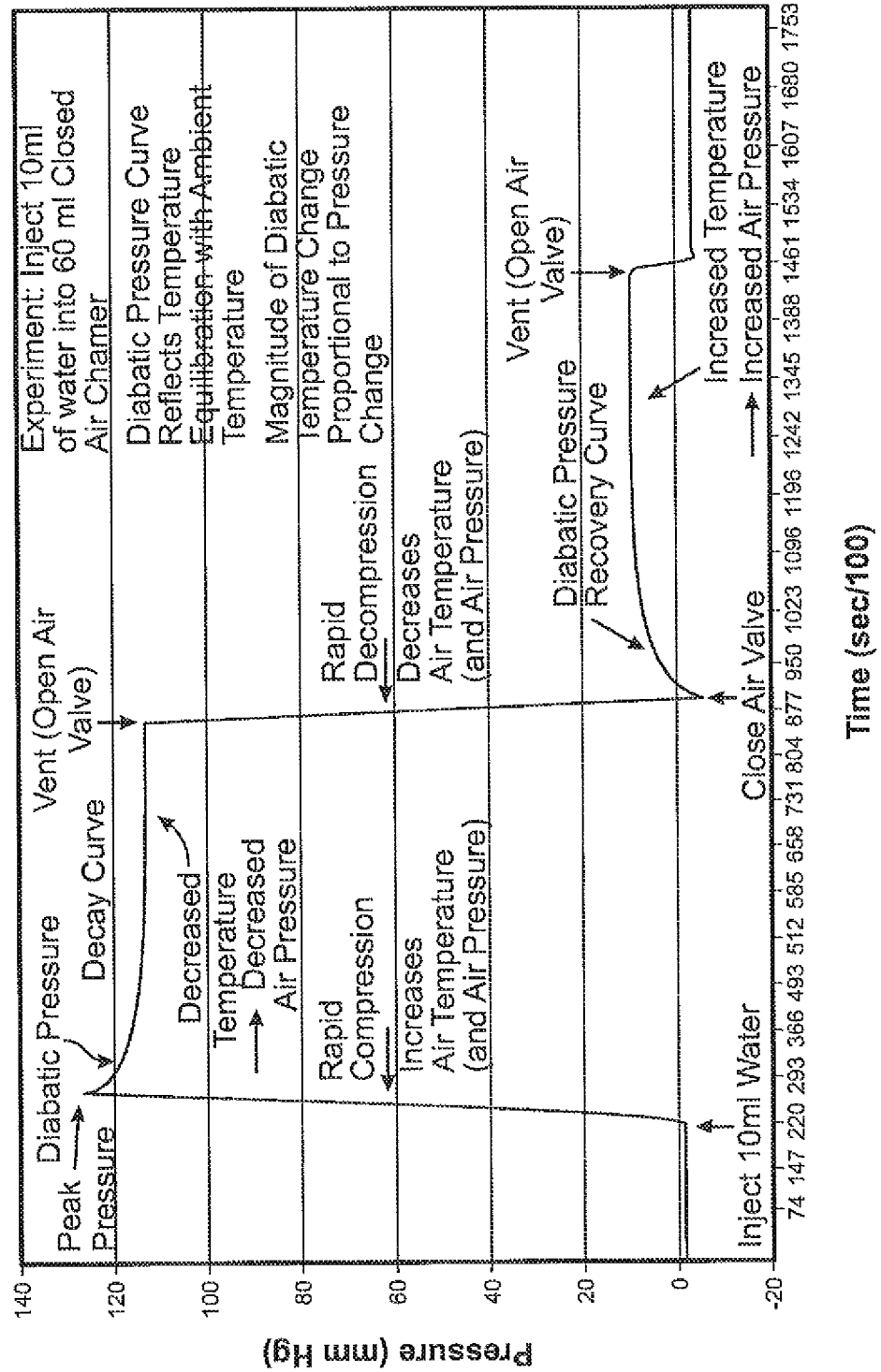
FIG. 13 depicts an exemplary pressure vs. time curve illustrating diabatic effects.

FIG. 13 provides further depiction of exemplary diabatic effects on a pressure vs. time curve. As shown in the left-hand side of the figure, diabatic effects lead to a rapid reduction of temperature (and hence pressure) following introduction of fluid in a receptacle. Following release of air, fluid, or both from the receptacle (right-hand side of figure), diabatic effects again lead to a temporary change in temperature (and hence pressure). It should be understood that accounting for and/or correcting for diabatic effects is a capability of the disclosed technology, but is not required for operation of the disclosed technology.

Figure 15:
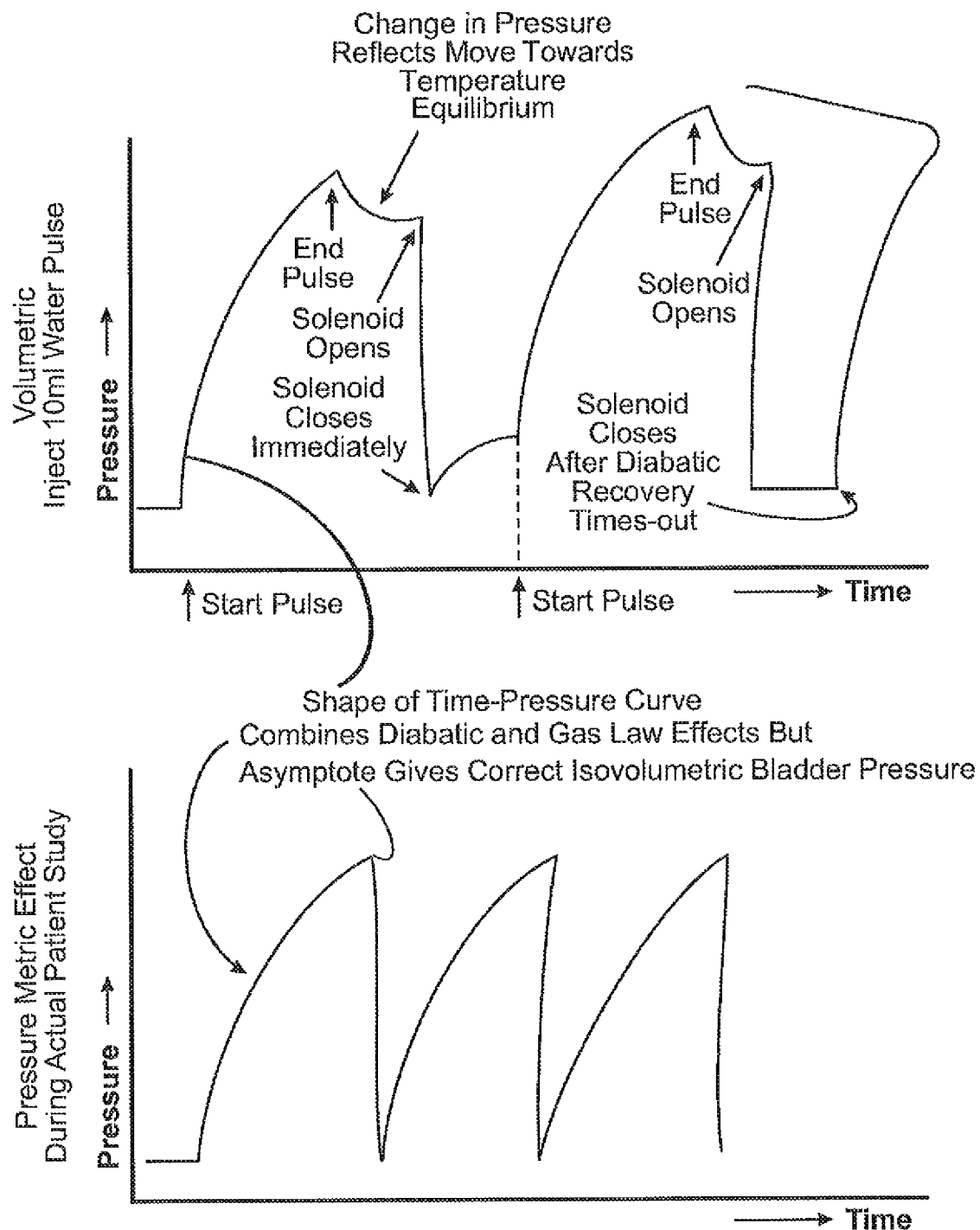
FIG. 15 depicts exemplary pressure vs. time curves— these can be in some cases corrected for diabatic error to use the initial portion of pressure-time curve to extrapolate isovolumetric bladder pressure and to measure instantaneous urine flow rates and resistance to flow.

FIG. 15 provides further presentation of diabatic effects on a pressure vs. time curve. As shown in the upper frame, urine enters a closed receptacle, causing an increase in pressure within the receptacle. Diabatic effects result in a temporary change in temperature (and hence pressure), which then resolves as temperature and pressure reach an equilibrium. A valve (here, a solenoid) then opens, releasing air, urine, or both. The pressure then falls (suitably to atmospheric pressure), the solenoid closes (suitably during continued urination), and the system then begins collecting the next pressure vs. time curve, as shown in the right-hand side of the upper frame of FIG. 15. Any of the pressure vs. time curves may be used as the basis for the disclosed methods, although a user may wish to use data from the second cycle and subsequent cycles, as those cycles may contain data that has been collected at conditions that are more equilibrated than the first cycle.

As further shown in FIG. 15, the shape of the pressure vs. time curves may, in some cases, combine diabatic and gas law effects. But the asymptotic pressure estimated from one or more pressure vs. time curves yields a suitable value for the isovolumetric bladder pressure, and one may account for, or eliminate sources of error, such as diabatic processes, changes in atmospheric pressure, changes in temperature due to introduction of urine at body temperature. Thus, as shown, diabatic error may change the shape of the curve (creating error in flow and resistance measures) but can give the correct isovolumetric pressure if back pressure is permitted to increase to asymptote, although isovolumetric bladder pressure can be uncomfortable in some cases for the distal urethra. One may eliminate diabatic error so as to permit extrapolating isovolumetric pressure from initial portion of pressure-time curve.

An exemplary system is shown in FIG. 30. That figure shows a component (that includes a receptacle) mounted or otherwise engaged with a device that coordinates or otherwise controls monitoring and/or urine or air release from the component. The system may include a display (e.g., a CRT, LED, or other display) that allows a user to visualize pressure vs. time curves or other data (e.g., asymptotic maximum bladder pressure, flow rate, flow resistance, etc.) and means to record and print out the data and analysis. The system may include a touchscreen, keyboard, mouse, pointer, or other control devices. A system may be battery-powered or plug into an electrical system. The system may be hard wired and/or use secure non-wired means of communication.

As shown, a system may be portable. The system may be on wheels for ease of movement. A system may also be manually-portable; as one example, the system may be sized so that it may be carried in a bag, suitcase, or other carrying case. In this way, the system may be portable so it can be transferred between examination rooms or even transferred between facilities.

Methods

The present disclosure also provides methods. The methods suitably include applying sufficient vacuum to a vacuum chamber so as to effect passage of a subject's anatomy into the vacuum chamber through a gap between an opening in the vacuum chamber and an opening of a urethral engagement conduit, the vacuum being applied so as to effect leak-tight fluid communication between the subject's urethra and a receptacle; and measuring, as a function of time during urine excretion, the pressure within the receptacle.

The methods may include calculating or measuring a maximum pressure of the urine stream. Measurement may be effected by, e.g., measuring the maximum pressure within the receptacle during urination. Maximum bladder pressure may be calculated, for example by, as described elsewhere herein, curve-fitting a pressure vs. time curve of urination so as to calculate an asymptotic maximum pressure. If the pressure vs. flow curve is linear, then initial urine flow rate may be measured at atmospheric pressure ("0" gage pressure) and then the pressure measured again at 50% of the initial flow rate. Doubling this pressure will give the bladder isovolumetric pressure.

The methods may include releasing urine from the receptacle during excretion, releasing air from the receptacle during excretion, or both. The methods suitably include measuring the pressure within the receptacle during urine excretion while the receptacle is closed to the environment exterior to the receptacle. In this way, the user may measure the bladder isovolumetric pressure within the receptacle during urination.

The methods may include measuring the pressure within the receptacle during urine excretion, followed by releasing urine, air, or both from the receptacle, followed by measuring the pressure within the receptacle during further urine excretion. Urine, air, or both may be released when the pressure within the receptacle reaches a specific value, e.g., 200 mm Hg, 150 mm Hg, 100 mm Hg, 50 mm Hg, or less.

The disclosed methods may also include measuring the temperature within the receptacle. The methods may also include changing the temperature within the receptacle. This may be done during urination, but may also be done before urination so as to place the component, receptacle, or both at or at about body temperature.

The methods also include calculating a flow resistance of the subject's urethra, measuring a flow resistance of the subject's urethra, or both. The methods also include calculating or measuring a compliance of the subject's bladder, the subject's urethra, or both. As explained elsewhere herein, the compliance may be expressed in terms of a slope of a pressure vs. time curve collected during urination.

The methods may also include measuring the pressure within the receptacle when a flow resistance device (such as those described elsewhere herein) is present. Such a device may add additional flow resistance beyond the inherent flow resistance of the component and receptacle. The flow resistance device may have an adjustable resistance. The methods may, in some embodiments, include correcting for diabatic effects, temperature effects, pressure effects, atmospheric effects, or any combination thereof on the receptacle.

A user may further prescribe a bladder treatment to a subject that exhibits LUTS and a maximum isovolumetric bladder pressure that is below a certain value (e.g., 60 mm Hg) and a flow resistance (or compliance) that is also below a certain value. A user may also prescribe a prostate treatment for a patient with LUTS if isovolumetric bladder pressure is normal (e.g., above 80 mm Hg) and flow resistance is elevated.

Exemplary operation

Patients undergoing uroflometry/urodynamic evaluation with the disclosed technology are suitably instructed to come to the office with a full bladder. The test requires some amount of urine, e.g., 50 mL, 100 mL, 150 mL, 200 mL, or more. A full bladder is preferable, but is not necessary to operation of the technology.

Once in the exam room, a patient may be tested either standing or seated. Bedridden patients may also be tested. The UED is fitted to the end of the urethra (the penis, in the case of male patients), and the patient is asked to urinate and continue until his bladder is empty. After the FPMC detects the onset of urine flow, the FPMC cycles a valve (e.g., a solenoid valve) according to a preset program.

Initially the valve is closed, which in turn gives rise to urine flowing into a closed air space of known volume, increasing the air pressure in the space until a predetermined maximum pressure is generated or calculated (100 mm Hg indicates a "strong" bladder), or else an asymptote is reached at some lower pressure (an asymptote of less than 60 mm Hg suggests a "weak" bladder). At this point the valve opens and dumps the urine, and the valve is immediately closed to initiate another cycle. The FPMC repeats cycles of opening and closing the solenoid valve while concurrently measuring both the time-pressure buildup and urine flow rate until the patient's bladder is empty. The slope of the time-pressure curve (at a given back-pressure) is a measure of the instantaneous urine flow rate at that pressure. The inverse slope of the time-pressure curve (at a given back-pressure) is a measure of the urethral resistance at that pressure. In this way, the non-invasive system generates the information from uroflowmetry combined with urodynamics to provide the information about both bladder strength and urethral resistance (e.g., bladder outlet obstruction) needed to determine the cause (or causes) of LUTS.

Information collected in the conduct of the test generates clinically significant data including:

(a) Asymptotic static pressure measures which reflect bladder strength (i.e., the pressure asymptote of the pressure-time curve is the bladder isovolumetric pressure at zero flow after subtracting hydrostatic pressure head). At the asymptote, the pressure in the UED equals bladder pressure plus hydrostatic pressure, and bladder pressure comprises intra-abdominal pressure plus detrusor pressure;

(b) Dynamic pressure-time measures during cycles of pressure buildup and relief that reflect the interaction between bladder strength and urethral resistance. The inverse slope at any point of the pressure vs. time curve is a measure of resistance through the urethral obstruction at the differential pressure across the obstruction (e.g., BOO, or bladder outlet obstruction due to BPH), which is bladder pressure plus the hydrostatic pressure minus the back-pressure in the UED. The pressure drop across the obstruction at any given flow rate is a measure of resistance to flow, and the pressure drop (resistance) becomes zero at the pressure asymptote (i.e., at zero flow). Once isovolumetric bladder pressure at zero flow is known, one can calculate the actual numerical resistance of the urethral obstruction from the inverse slope of the pressure-time curve. There is no need for a nomogram that provides only a crude estimate of obstruction vs. non-obstruction (i.e., non-parametric).

Bladder pressure includes intra-abdominal and detrusor pressure. Intra-abdominal pressure is not an issue with the UED (as with other invasive and non-invasive methods) because the driving force across the urethral obstruction is the differential pressure (bladder pressure plus hydrostatic pressure minus UED pressure), which is calculated from the pressure-time curve after isovolumetric bladder pressure at zero flow is measured.

(c) Other measures that reflect the visco-elastic properties of the urethra and bladder tissues.

One aspect of the disclosed technology is that the technology functions using measurement of only a single dependent variable, pressure as a function of time. No separate uroflowmeter is needed, as flow rate is a function of the time-pressure curve (dependent on the pre-set volume of the closed air space). As a result, there is no phase difference between bladder pressure and urine flow measurements. Other existing technologies, such as the penile cuff technology, however, are out-of-phase, and use a separate uroflowmeter to measure urine flow. Because instantaneous urine flow rate and instantaneous bladder pressure are measured simultaneously by the disclosed technology, it is possible to accurately apply flow models to analyze and interpret the fluid dynamics of the lower urinary tract, and thereby identify and partial out the effects of bladder weakness from the effects of increased urethral resistance in explaining the reduced urine flow rate in LUTS.

Exemplary data

The following section describes data collected from both human subjects and so-called "phantoms" (electronically-controlled hydraulic devices combining pumps and flow resistors) that are used to model the characteristics of the lower urinary tractThese data demonstrate the diagnostic power of the disclosed technology. In each of these exemplary, non-limiting phantom cases, a solenoid valve was to automatically open at either a preset high asymptotic pump pressure (e.g., 100 mm Hg) if bladder pressure is "normal," or at some lower asymptotic pressure (e.g. 60 mm Hg) if the bladder is "weak." The pump output could be set to any specified pressure to emulate the isovolumetric pressure of either a strong or a weak bladder. A variety of linear flow resistors (e.g., capillary tubes) and non-linear resistors (e.g., needle valves) could be inserted in the flow stream to emulate different forms of urethral obstruction. In each case the phantom "urinates" into a closed air space from which the "urine" (or air) is dumped when the solenoid opens.

As shown in FIG. 1, phantom patient 1 exhibits normal bladder pressure (>80 mm Hg) and normal flow rate (>15 ml/s). The high slope value of the time-pressure curve during each cycle of "urination" indicates low resistance to flow under conditions of normal bladder pressure, i.e., no urethral obstruction.

Figure 2:
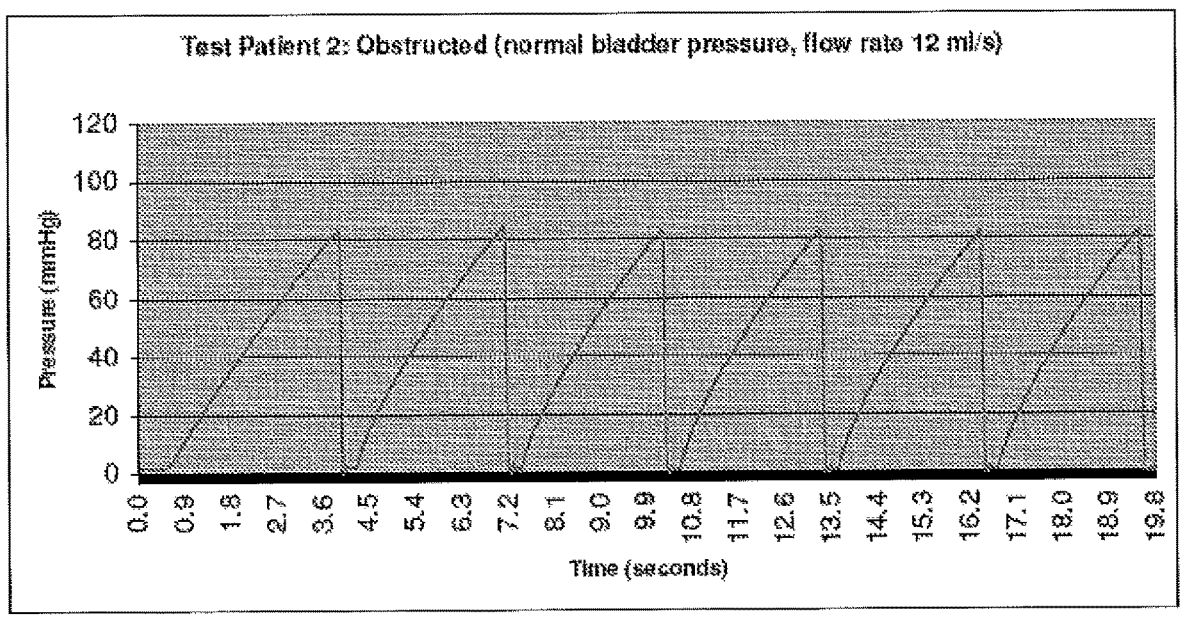
FIG. 2 provides a pressure vs. time plot for Test Patient 2.
Figure 3:
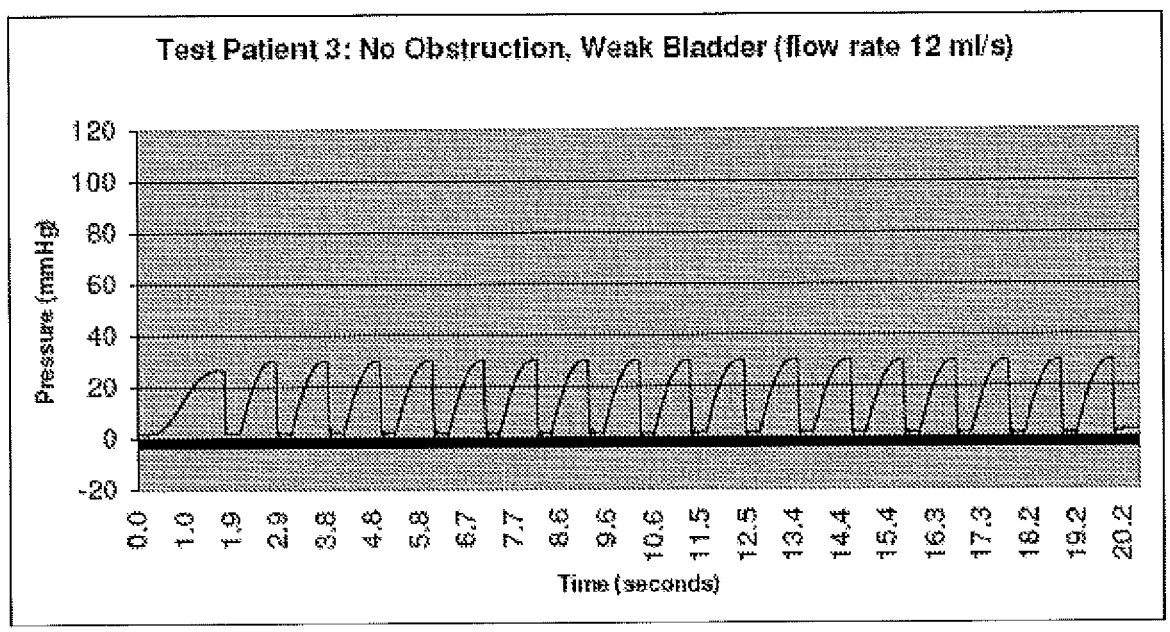
FIG. 3 provides a pressure vs. time plot for Test Patient 3.

The clinical potential of the disclosed technology is apparent when comparing phantom patient 2 (FIG. 2) and phantom patient 3 (FIG. 3). Note that both phantom patients 2 and 3 present with low flow rate (i.e., comparatively low slope to the pressure-time curve). Phantom patient 2, however, exhibits a normal bladder pressure (i.e., low flow with normal bladder pressure) as compared to phantom patient 3 (i.e., low flow with low bladder pressure). Although both phantom patients 2 and 3 exhibit the same symptom (i.e., weak stream) with the same low flow rate, each has a different cause. Phantom patient 2 suffers from bladder outlet or urethral obstruction while phantom patient 3 has bladder weakness. Distinguishing the source of decreased urine flow is the main challenge in differential diagnosis of obstruction due to BPH. For phantom patient 3, understanding the reason for the weak stream is the difference between prescribing a non-invasive medical treatment that will address the cause of the patient's weak stream and prescribing unnecessary prostate surgery that may not address the weakened bladder that is the source of the diminished urine stream. Thus, when comparing FIG. 2 with FIG. 3, one may observe that although both figures show comparatively low urine flow, these low flows are from different causes; namely that FIG. 2 illustrates low flow due to urethral obstruction, and FIG. 3 illustrates low flow due to bladder weakness.

Figure 4:
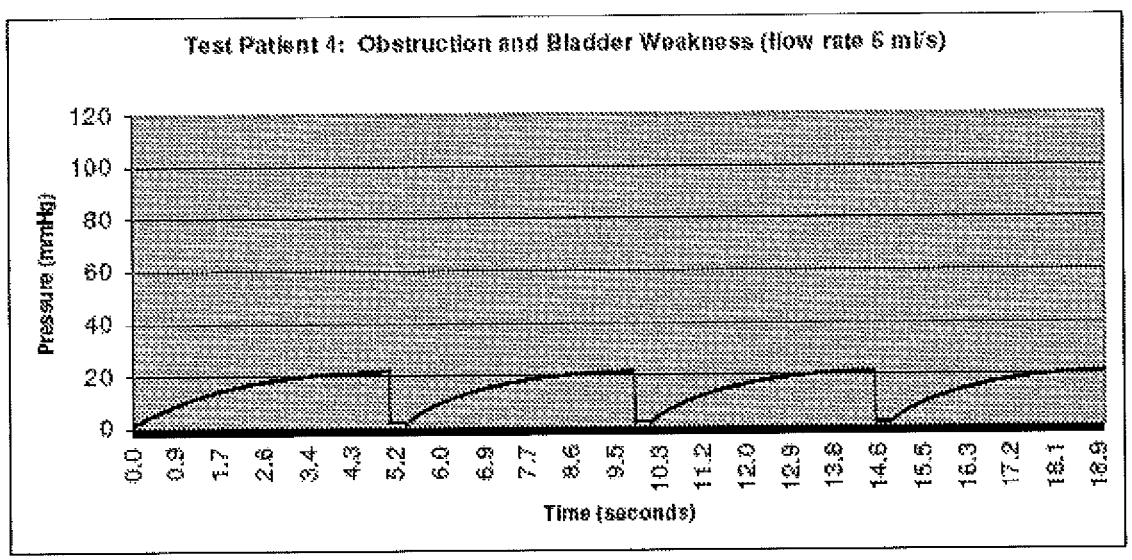
FIG. 4 provides a pressure vs. time plot for Test Patient 4.

The diagnostic power of the disclosed technology is further shown by reference to FIG. 4, which figure illustrates data from phantom patient 4, which patient presents with very low flow rate, and exhibits both low bladder pressure and a low slope value, indicative of both bladder weakness and obstruction.

Figure 5:
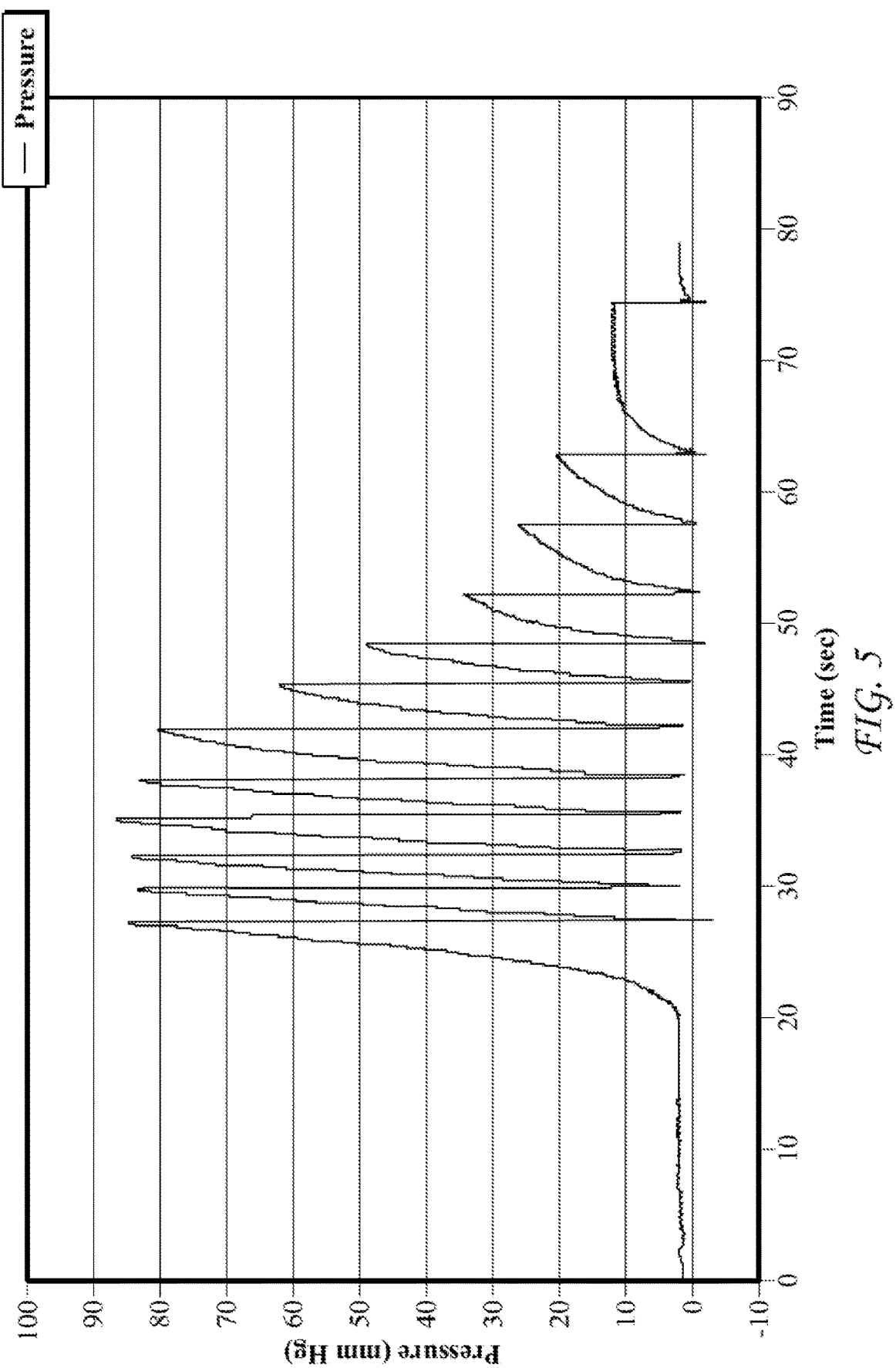
FIG. 5 provides a pressure vs. time plot for an exemplary patient.

FIG. 5 presents a representative patient record collected using the disclosed technology. As shown, this patient exhibits a bladder pressure (>80 mm Hg) that is in the normal range after urination initiated. There is, however, evidence of urethral obstruction, as the calculated peak flow rates are comparatively low (<15 ml/s). The entire test shown in FIG. 5 required only 60 seconds from initiation of urination to empty bladder. Total urine volume was 250 ml. This is a record of a patient with LUTS and an analysis of first 5 time-pressure curves shows normal isovolumetric bladder pressure with reduced flow rate from urethral obstruction due to BPH.

Figure 52:
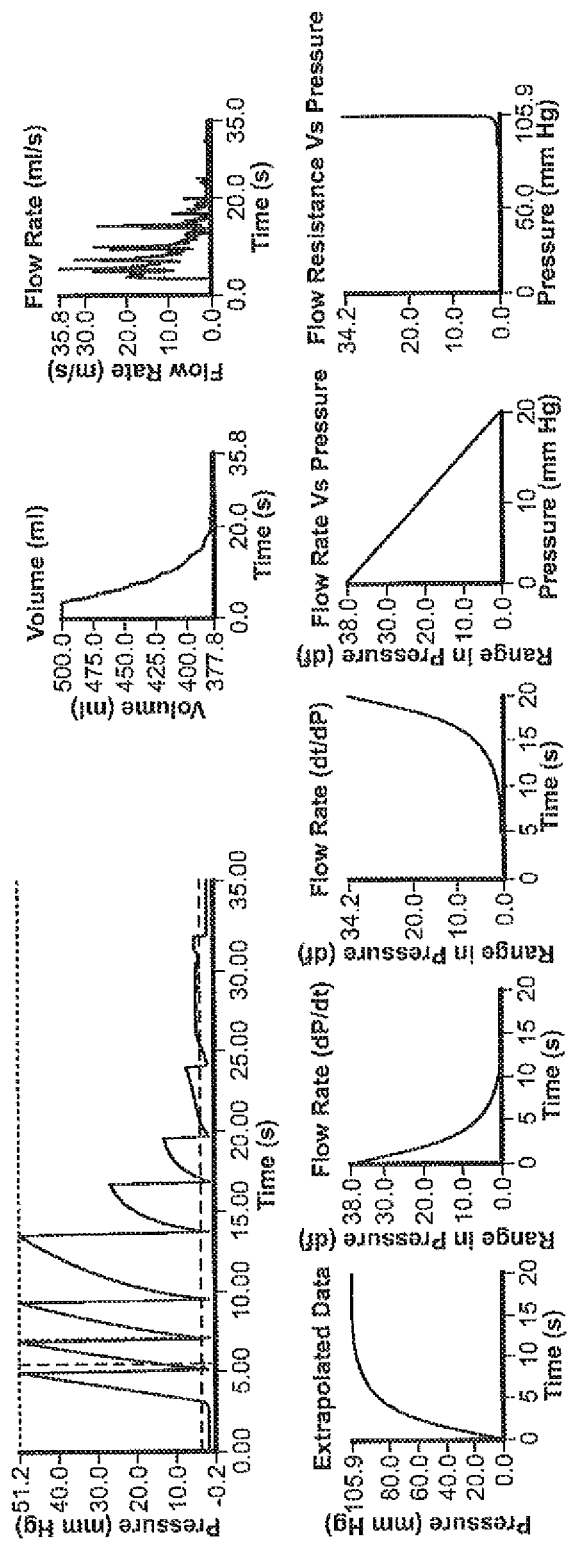
FIG. 52 provides data gathered from an actual patient using the disclosed technology.

FIG. 52 provides a GUI (Graphical User Interface) showing data gathered by an exemplary air venting system from a patient with LUTS (frequency of urination and weak stream) successfully treated with tamsulosin (an alpha blocker used to treat BOO due to BPH). The test was performed with the solenoid valve trigger set to vent back-pressure within the closed air space at 50 mm Hg to prevent pain from stretching the patient's distal urethra. One may note an increasing width (decreasing flow rate) and decreasing asymptotic pressure of the consecutive pressure-time curves as the bladder empties. Analysis (curve-fitting) of the second pressure-time curve gives a normal calculated isovolumetric bladder pressure of 106 mm Hg associated with a normal maximum urine flow rate (>15 ml/s). These numbers suggest that tamsulosin is an effective medical treatment for this patient. Patient still has frequency of urination (note total volume of urine only 120 ml) but his weak stream has been alleviated. Note that the NUD serves as a convenient objective method to evaluate response to treatment. Also, only a minimal volume of urine is required to perform this rapid and pain free procedure.

Figure 53:
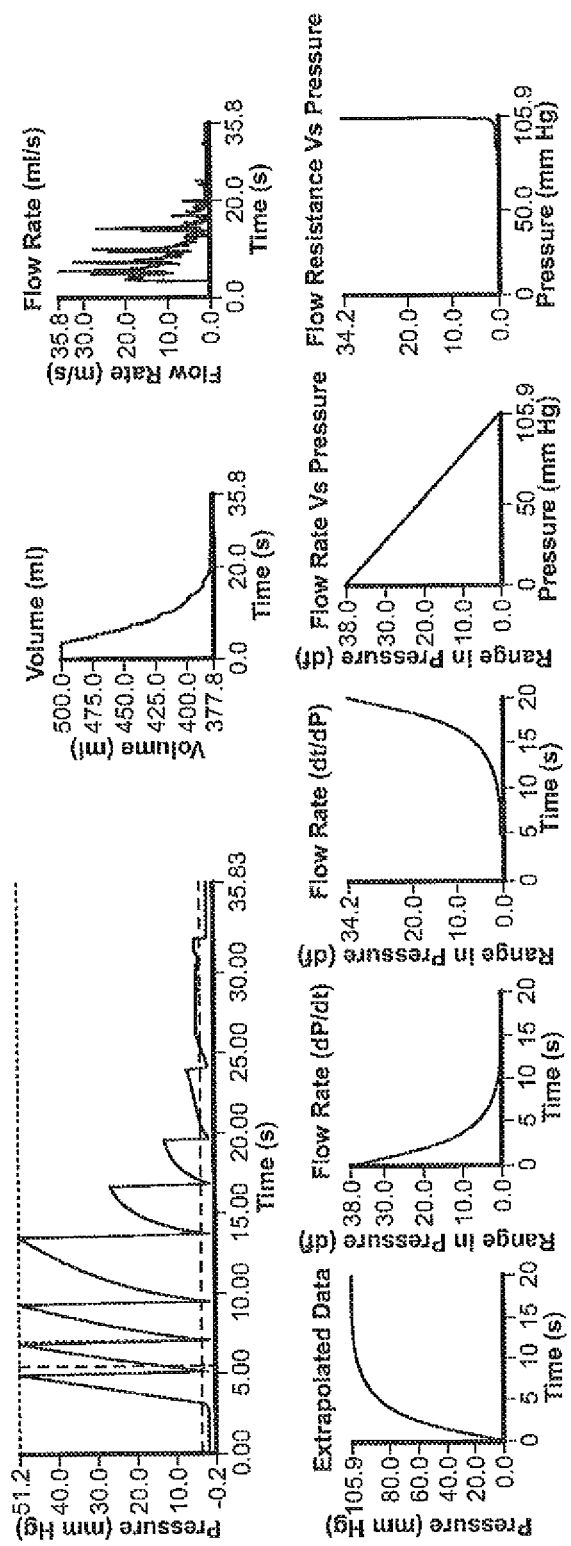
FIG. 53 provides data generated by the phantom patient using the disclosed technology.

FIG. 53 provides a GUI for a test using a phantom patient with water at room temp (72 deg. F) in lieu of urine; in this case the test was performed with an air venting UED; one may note that the water displaces an equivalent volume of air from the closed air space (urine receptacle) so that air compliance decreases with each pressure-time cycle, and the PFMC program must recalculate the remaining air volume after each air venting in order to use the gas laws to calculate isovolumetric bladder pressure, instantaneous urine flow rate, instantaneous urethral resistance, and instantaneous LUT compliance from the consecutive time-pressure (i.e., back-pressure) curves. One may compare this record to FIG. 1 that was generated by venting "urine" so the air volume of the closed air space remains constant from one pressure-time curve to the next.

This is an example of normal bladder pressure with low urine flow consistent with BPH or other source of bladder outlet or urethral obstruction. One may also note that bladder pressure and flow rate build up rapidly after urination begins, and drop off gradually as the bladder empties. Therefore calculation of peak (isovolumetric) bladder pressures, slopes of the time-pressure curves, and dynamic time-pressure and time-flow parameters are best performed when these measures become consistent (e.g., during the 2nd, 3rd, 4th and 5th pressure cycles in this sample record). Without being bound to any particular theory, in some cases, the user may elect to use data from points in time after urination begins, instead of data from the time (i.e., t=0) when urination begins. As it can take some time for the bladder to develop maximum pressure during urination (the bladder is a smooth muscle and takes time to achieve full strength), a user may elect to gather data or use data taken at some time after urine flow starts, not necessarily at initiation. A user may also elect (see FIG. 5) not to rely on data taken at the end of micturition, as such data may show a lower pressure because once the bladder has emptied, the bladder is no longer achieving its full strength. A user may elect to rely on data taken when a bladder has achieved isovolumetric contraction, which can take some time to occur. For example, the user may elect to use pressure vs. time data from 0.1 seconds, 0.5 seconds, 1.0 seconds, 5.0 seconds, or more after urination begins. Alternatively, the user may elect to utilize data gathered after the urine receptacle has been vented one or more times to the environment exterior to the receptacle.

Summary

In summary, the present disclosure provides a number of advancements. First, the disclosed non-invasive urodynamic devices (NUD) provide hardware and software. The hardware may include a urethral extender device (UED) that includes (a) the vacuum chamber and (b) a closed air space. For male patients, the UED uses the vacuum chamber to adhere to the periurethral tissue of the glans penis and thereby connect the subject's lower urinary tract (LUT) to the closed air space within the UED into which urine flows during micturition. The electronic hardware may also include a flow and pressure measurement and control (FPMC) system as described elsewhere herein. The software for the FPMC system may include programs that (a) accept data from input devices (such as pressure-time data from pressure sensors) within or connected to the closed air space of the UED, (b) process and measure the data, and (c) control output devices (e.g., solenoid valves) that relieve back-pressure created during micturition by venting the closed air space whenever a predetermined air pressure (or volume of urine) is detected in the closed air space. A FPMC may also regulate the vacuum pump and the solenoid valve used to connect (and disconnect) the glans penis to (and from) the UED.

The disclosed devices also provide improved attachment of the UED to subject's LUT. Prolonged exposure to high vacuum may result in physical discomfort plus bruising of the glans. The disclosed UED design uses only an initial vacuum to draw (for male patients) the lubricated periurethral tissue of the glans penis through an appropriately sized and shaped annular space in the proximal part of the UED, and thence into the vacuum space where the ring of periurethral glans tissue within the vacuum chamber expands to mechanically trap the glans and thereby create a strong physical attachment and airtight seal. The design of the annular ring also pulls open the urethral orifice and thereby prevents obstruction to urine flow from the meatus. The vacuum may be reduced to a lower level (less than 100 mm Hg in some embodiments) required to maintain the tissue seal within the vacuum space even with a comparatively high isovolumetric bladder pressure. When the test is over the vacuum is released and the glans tissue is free to slip out of the vacuum space.

The disclosed methods of attaching devices to tissue may be used to create a leak-proof connection between a body orifice and a test device (e.g., UED to glans), or to stabilize tissue during a procedure, modify blood flow (e.g., compress a vessel) or even to immobilize an operative site during surgery, as for example, prevent movement of the operative site during open-chest or key-hole surgery performed on the beating heart. Current methods for immobilizing the beating heart during surgery use clamping devices that can bruise the heart and compromise function (e.g., decrease cardiac output) as well as adversely affect blood flow.

The disclosed technology also addresses devices that may be reusable, disposable, or semi-disposable. The disclosed designs permit the UED to be disposable (or semi-disposable) because only air (rather than urine) is vented through a solenoid valve with each iteration of the pressure-time curve. An alternate design using disposable solenoid valve components molded into (embedded within) the UED, and non-disposable parts (e.g., solenoid coil) located outside the UED permits urine venting from a disposable UED. Air venting may be preferred in some embodiments due to mechanical simplicity and low cost. As explained elsewhere herein, more complex mathematical calculations may be used with air venting than with urine venting (where the closed air space volume remains constant for each consecutive pressure-time curve). With air venting the urine collects within the closed air space, displacing more air with each pressure-time curve iteration. The result is serial decreases in the compliance of the closed air space. An advantage of the air venting method is that analysis of the resulting series of pressure-time curves permits calculation of the compliance of the lower urinary tract (LUT) in addition to calculating bladder isovolumetric pressure, urine flow rates and urethral resistance to urine flow. Other clinically meaningful parameters may also be derived from the pressure-time curves generated from air venting during micturition into the UED. A special advantage of a disposable UED is that the device and its contents can be disposed of as medical waste without need to clean and refurbish. Alternately the urine can be drained from the UED into the toilet before disposal.

A semi-disposable UED may have a removable seal (e.g., expansion stopper) inserted at the distal end of the closed air space that permits removal of the enclosed heat sink, etc. and draining of urine from the closed air space, washing and sterilizing all reusable UED parts, and reassembling the UED. This design permits a variety of specialized heat sinks, space occupying inserts (to modify the volume of the closed air chamber for subjects who produce small volumes of urine during micturition), and sensors (e.g., RFID pressure and temperature transmitters), etc. to be cleaned and reused. A UED may be designed to accommodate non-invasive measures of LUT function performed on females, children, infants, and animals. The NUD may be used repeatedly before and after treatment to evaluate response to medical and surgical interventions for LUT disorders. Also, the use of the NUD is not limited to the doctor's office or laboratory setting. A simplified version with means to record the pressure-time data for later analysis can be placed in the home setting where a properly trained patient may perform the test on himself. As for example, before and after use of a prescribed treatment. Because of the ease of use, research to test the efficacy of newly proposed pharmacologic or surgical treatments for LUT symptoms may also be performed with the NUD.

The distal urethra (DU) does not usually experience significant back-pressure, and obstructing the DU during micturition results in painful stretching of the DU. Such pain may be demonstrated when a male pinches off urine flow while urinating. Thus, non-invasive devices used to measure isovolumetric pressure by blocking urine flow are intrinsically painful. One such devices includes the CT3000 cuff device (Mediplus Co.). To eliminate pain caused by exposing the DU to full bladder pressure, the disclosed NUD design extrapolates the isovolumetric bladder pressure from analysis of the initial low pressure segment (e.g., <60 mm Hg) of the pressure-time curve. Isovolumetric bladder pressure may be measured or estimated using the NUD without exposing the distal urethra to painfully high pressures because the design of the UED creates a linear relationship between pressure and flow. Therefore, the low pressure segment of the pressure-time curve can be used to calculate the isovolumetric bladder pressure by curve fitting the initial portion of the pressure-time curve or else extrapolating from the initial portion of the pressure-flow curve. If the relation of flow to back-pressure in the closed air chamber is linear, the initial flow rate into the closed air chamber at zero back-pressure (atmospheric pressure) can be used to accurately extrapolate the pressure at zero flow (isovolumetric bladder pressure). For example, the back-pressure measured at 50% of the initial flow is one-half of the isovolumetric bladder pressure.

Compression (or decompression) of air within the urine receptacle may raise (or lower) the air temperature resulting in diabatic error incorporated within the pressure-time curve (which provides data for calculating instantaneous flow rates and flow resistance). However, the isovolumetric bladder pressure measurement was accurate because the diabatic error rapidly resolved once the pressure within the closed air space equilibrated with the bladder pressure. However, measuring high bladder pressures using the UED were associated with pain from stretching the distal urethra. This diabatic error problem may be address by distributing a heat sink, such as metal wool, within the closed air space. The heat sink has much greater mass (and de minimus volume) compared to the air within the closed air space. As a result there is little change in air temperature (minimizing diabatic pressure measurement error) during compression and decompression of the closed air space. The pressure-time curves are now essentially free of diabatic error so they can be used to calculate all clinically relevant measures from the initial (pain-free) low back-pressure portion of the pressure-time curve.

What is claimed:
1. A system, comprising:
 a receptacle configured for sealable fluid communication with a subject's bladder;
 a sensor configured to measure a pressure within the receptacle while the receptacle is in sealed communication with the subject's bladder;
 a release device configured to release pressure from the receptacle;
 the system being configured to measure a urine flow of a subject and actuate the release device to release pressure within the receptacle when the pressure within the receptacle reaches a threshold level, the threshold level being lower than the pressure in the receptacle at which the subject's urine flow into the receptacle stops, (a) the system being configured to determine a slope of a receptacle pressure vs. time curve obtained during the subject's urination, (b) the system being configured to determine an inverse slope of a receptacle pressure vs. time curve obtained during the subject's urination, or (c) both (a) and (b).

2. The system of claim 1, wherein the system is being configured to estimate a pressure within the receptacle at which a urine flow into the receptacle stops by calculating from one or more pressure vs. time curves obtained during the subject's urination an asymptotically-derived isovolumetric bladder pressure.

3. The system of claim 2, wherein during the one or more pressure vs. time curves obtained during the subject's urination the receptacle pressure does not rise to a pressure at which a urine flow into the receptacle stops.

4. The system of claim 2, wherein during the one or more pressure vs. time curves obtained during the subject's urination the maximum receptacle pressure does not exceed about 50 mm Hg.

5. The system of claim 2, wherein during the one or more pressure vs. time curves obtained during the subject's urination the maximum receptacle pressure does not exceed about 30 mm Hg.

6. The system of claim 1, wherein the system is configured to determine, from one or more pressure vs. time curves, the relative contributions to receptacle pressure from bladder pressure and from a urethral obstruction of the subject.

7. The system of claim 1, wherein the receptacle comprises a compliant structure configured to deform in response to the presence of a fluid within the receptacle.

8. The system of claim 1, wherein the receptacle comprises a heat absorbing material that absorbs heat energy generated by compression of air within the closed air space that might otherwise raise the temperature within the receptacle.

9. The system of claim 8, wherein the heat absorbing material comprises a metal wool or a glass wool.

10. A method of non-invasively assessing urinary tract condition, comprising:

obtaining, during a subject's urination into a sealed receptacle, one or more receptacle pressure vs. time curves, with a processor, controllably operating a release device configured to release pressure from the receptacle and so as to release pressure within the receptacle when the pressure within the receptacle reaches a threshold level, the threshold level being lower than the pressure in the receptacle at which the subject's urine flow into the receptacle stops, and (a) determining a slope of a receptacle pressure vs. time curve obtained during the subj ect's urination, (b) determining an inverse slope of a receptacle pressure vs. time curve obtained during the subject's urination, or (c) both (a) and (b).

11. The method of claim 10, further comprising correlating the slope of a receptacle pressure vs. time curve obtained during the subject's urination to an asymptotically-derived isovolumetric bladder pressure of the subject.

12. The method of claim 10, further comprising correlating the inverse slope of a receptacle pressure vs. time curve obtained during the subject's urination to urethral obstruction of the subject.

13. The method of claim 10, further comprising determining the relative contributions to receptacle pressure from bladder pressure and from a urethral obstruction of the subject.

14. The method of claim 10, further comprising correcting for diabatic effects within the receptacle during the subject's urination.

15. The method of claim 10, further comprising releasing a pressure within the receptacle at least once during the subject's urination.

* * * * *